United States Patent
Blum et al.

(10) Patent No.: US 12,005,164 B2
(45) Date of Patent: Jun. 11, 2024

(54) ENHANCED AIR CLEANING COMPUTER MONITOR

(71) Applicant: Air-Clenz Systems, LLC, Atlanta, GA (US)

(72) Inventors: Ronald Blum, Atlanta, GA (US); Anita Broach, Christiansburg, VA (US); Jack Loeb, Fisher Island, FL (US); Stuart Sheldon, Atlanta, GA (US)

(73) Assignee: Air-Clenz Systems, LLC, Atlanta, GA (US)

( * ) Notice: Subject to any disclaimer, the term of this patent is extended or adjusted under 35 U.S.C. 154(b) by 0 days.

(21) Appl. No.: 17/300,936

(22) Filed: Dec. 15, 2021

(65) Prior Publication Data

US 2022/0111108 A1 Apr. 14, 2022

Related U.S. Application Data

(63) Continuation-in-part of application No. 17/404,570, filed on Aug. 17, 2021, now Pat. No. 11,712,494.
(Continued)

(51) Int. Cl.
*A61L 9/20* (2006.01)
*A61L 9/22* (2006.01)

(52) U.S. Cl.
CPC ...... *A61L 9/20* (2013.01); *A61L 9/22* (2013.01); *A61L 2209/111* (2013.01);
(Continued)

(58) Field of Classification Search
CPC ..... A61L 9/16; A61L 9/18; A61L 9/20; A61L 9/205; A61L 9/22; A61L 2209/111; A61L 2209/134; A61L 2209/14; A61L 2209/15
See application file for complete search history.

(56) References Cited

U.S. PATENT DOCUMENTS 6,503,458 B1  1/2003  Ogle
7,997,531 B2  8/2011  Bettell
(Continued)

FOREIGN PATENT DOCUMENTS

CN   104732877 A   6/2015
CN   207304877 U   5/2018
(Continued)

OTHER PUBLICATIONS

Machine translation of JP-2004113561-A (Year: 2004).*
(Continued)

*Primary Examiner* — Timothy C Cleveland
(74) *Attorney, Agent, or Firm* — Woods Rogers Vandeventer Black PLC; Nathan A. Evans

(57) ABSTRACT

An air collection and cleaning system or apparatus including a computer monitor, wherein the computer monitor in addition to displaying images, information, and/or data, comprises an exhaled air collector, wherein the computer monitor's computer screen forms an exhaled air blocking surface which is part of the exhaled air collector and wherein the exhaled air collector collects exhaled air, and the computer screen's surface deflects exhaled air towards an exhaled air suction intake, an air purification unit, or both.

17 Claims, 48 Drawing Sheets

Related U.S. Application Data which is a continuation of application No. 17/353,341, filed on Jun. 21, 2021, now abandoned, which is a continuation of application No. 17/331,239, filed on May 26, 2021, now Pat. No. 11,324,850.

(60) Provisional application No. 63/283,524, filed on Nov. 28, 2021, provisional application No. 63/272,907, filed on Oct. 28, 2021, provisional application No. 63/271,933, filed on Oct. 26, 2021, provisional application No. 63/251,855, filed on Oct. 4, 2021, provisional application No. 63/240,795, filed on Sep. 3, 2021, provisional application No. 63/222,638, filed on Jul. 16, 2021, provisional application No. 63/216,644, filed on Jun. 30, 2021, provisional application No. 63/196,565, filed on Jun. 3, 2021, provisional application No. 63/195,608, filed on Jun. 1, 2021, provisional application No. 63/182,964, filed on May 2, 2021, provisional application No. 63/173,443, filed on Apr. 11, 2021, provisional application No. 63/158,983, filed on Mar. 10, 2021, provisional application No. 63/156,598, filed on Mar. 4, 2021, provisional application No. 63/149,581, filed on Feb. 15, 2021, provisional application No. 63/125,701, filed on Dec. 15, 2020, provisional application No. 63/063,727, filed on Aug. 10, 2020, provisional application No. 63/060,009, filed on Aug. 1, 2020, provisional application No. 63/051,309, filed on Jul. 13, 2020, provisional application No. 63/050,253, filed on Jul. 10, 2020, provisional application No. 63/048,877, filed on Jul. 7, 2020, provisional application No. 63/046,430, filed on Jun. 30, 2020, provisional application No. 63/031,321, filed on May 28, 2020, provisional application No. 63/029,956, filed on May 26, 2020.

(52) U.S. Cl.
CPC ..... *A61L 2209/134* (2013.01); *A61L 2209/14* (2013.01); *A61L 2209/15* (2013.01)

(56) References Cited

U.S. PATENT DOCUMENTS

| | | |
|---|---|---|
| 8,857,911 B2 | 10/2014 | Aguirre et al. |
| 9,938,015 B2 | 4/2018 | Savian |
| 10,421,547 B2 | 9/2019 | Carlioz et al. |
| 11,097,846 B2 | 8/2021 | Madrigal et al. |
| 2004/0232283 A1 | 11/2004 | Ferry et al. |
| 2006/0097553 A1 | 5/2006 | Spurlock et al. |
| 2007/0040434 A1 | 2/2007 | Plant |
| 2007/0103776 A1 | 5/2007 | Cok |
| 2007/0164157 A1 | 7/2007 | Park |
| 2009/0050740 A1 | 2/2009 | Saint-Jalmes et al. |
| 2009/0302158 A1 | 12/2009 | Darbyshire et al. |
| 2010/0243754 A1 | 9/2010 | Harris |
| 2018/0079508 A1 | 3/2018 | Carlioz et al. |
| 2018/0257027 A1* | 9/2018 | Desai ................ B01D 53/326 |
| 2019/0128553 A1 | 5/2019 | Hilbig et al. |
| 2019/0210733 A1 | 7/2019 | Herault et al. |
| 2019/0367170 A1 | 12/2019 | Carlioz et al. |
| 2022/0054699 A1* | 2/2022 | Nakama ................ B64D 13/00 |
| 2022/0072185 A1* | 3/2022 | Miller ...................... A61L 9/20 |
| 2022/0185062 A1* | 6/2022 | Khaw ...................... B60S 1/64 |

FOREIGN PATENT DOCUMENTS

| | | | | |
|---|---|---|---|---|
| CN | 108319341 A | | 7/2018 | |
| EP | 1878977 A2 * | | 1/2008 | ............ F24F 1/0007 |
| JP | 2004113561 A * | | 4/2004 | ............ A61L 9/205 |
| KR | 20190052468 A | | 5/2019 | |
| WO | WO-2020137465 A1 * | | 7/2020 | ............ A61L 9/205 |

OTHER PUBLICATIONS

A. K. Melikov; Advanced air distribution: improving health and comfort while reducing energy use; Indoor Air 2016; 26: 112-124; John Wiley & Sons Ltd.; Singapore.

Arsen K. Melikov; Advanced air distribution for minimizing airborne cross-infection in aircraft cabins; HVAC&R Research (2013) 19, 926-933; Taylor & Francis.

Jianlei Niu; Experimental study on a chair-based personalized ventilation system; Science Direct; 2005; Elsevier Ltd.

Application No. PCT/US2021/034281, International Search Report and Written Opinion dated Sep. 17, 2021.

Application No. PCT/US 21/38265, International Search Report and Written Opinion dated Sep. 30, 2021.

Application No. PCT/US 21/46307, International Search Report and Written Opinion dated Dec. 9, 2021.

Application No. PCT/US21/10060, International Search Report and Written Opinion dated Jul. 5, 2022.

* cited by examiner

COMPUTER MONITOR WITH EXHALED AIR COLLECTOR & AIR PURIFICATION CHAMBER (NOT VISIBILE)

COMPUTER MONITOR WITH EXHALED AIR COLLECTOR & AIR PURIFICATION CHAMBER (NOT VISIBILE)

DESKTOP COMPUTER MONITOR WITH SCREEN

RETROFIT-ABLE EXHALED AIR PURIFICATION UNIT ASSEMBLY FOR DESKTOP COMPUTER MONITOR

MONITOR OR ELECTRONIC DISPLAY WITH EXHALED AIR COLLECTOR AND AIR PURIFICATION CHAMBER

MONITOR OR ELECTRONIC DISPLAY WITH EXHALED AIR COLLECTOR AND AIR PURIFICATION CHAMBER

GAMBLING MONITOR SCREENS

MONITOR OR ELECTRONIC DISPLAY WITH EXHALED AIR COLLECTOR AND AIR PURIFICATION CHAMBER

GAMBLING MONITOR SCREENS

AIR PURIFICATION CHAMBER IS PRESENT BUT NOT VISIBLE

ENHANCED AIR CLEANING COMPUTER MONITOR

CROSS REFERENCE TO RELATED APPLICATIONS

The present application relies on the disclosures of and claims priority to and the benefit of the filing dates of the following U.S. Patent Applications:

U.S. application Ser. No. 17/404,570, Enhanced Exhaled Air Collector and Air Purification Unit and System, filed Aug. 17, 2021;

U.S. application Ser. No. 17/353,341, Enhanced Exhaled Air Collector and Air Purification Unit and System, filed Jun. 21, 2021;

U.S. application Ser. No. 17/331,239, Exhaled Air Purification Unit and System for Indoor Multi-Person Venue or Environment, filed May 26, 2021;

U.S. Appl. No. 63/029,956, Microbe Protection Systems, filed May 26, 2020;

U.S. Appl. No. 63/031,321, Microbe Protection Modules, filed May 28, 2020;

U.S. Appl. No. 63/046,430, Air Suction Sterilization Elevator Car, filed Jun. 30, 2020;

U.S. Appl. No. 63/048,877, Vehicle Microbe Protection System, filed Jul. 7, 2020;

U.S. Appl. No. 63/050,253, Advanced Air Suction Sterilization Elevator Car, filed Jul. 10, 2020;

U.S. Appl. No. 63/051,309, Advanced Vehicle Microbe Protection System, filed Jul. 13, 2020;

U.S. Appl. No. 63/060,009, Advanced Air Suction Air Sterilization Protection System, filed Aug. 1, 2020;

U.S. Appl. No. 63/063,727, Advanced Microbe Trap and Face Mask, filed Aug. 10, 2020;

U.S. Appl. No. 63/125,701, Advanced Air Purification System for Multi-Person Environment, filed Dec. 15, 2020;

U.S. Appl. No. 63/149,581, Multi-person Venue Air Purification System, filed Feb. 15, 2021;

U.S. Appl. No. 63/156,598, Air Handling Purification System, filed Mar. 4, 2021;

U.S. Appl. No. 63/158,983, Air Handling Purification System, filed Mar. 10, 2021;

U.S. Appl. No. 63/173,443, Recessed Personal Air Purifier for Backside of Seat Back, filed Apr. 11, 2021;

U.S. Appl. No. 63/182,964, Personal Air Purification Unit and System, filed May 2, 2021;

U.S. Appl. No. 63/195,608, Exhaled Air Collector and Air Purification for Desks and/or Tables, filed Jun. 1, 2021;

U.S. Appl. No. 63/196,565, Enhanced Exhaled Air Collector and Air Purification for Desks and/or Tables, filed Jun. 3, 2021;

U.S. Appl. No. 63/216,644, Exhaled Air Guide for Exhaled Air Collector, filed Jun. 30, 2021; and U.S. Appl. No. 63/222,638, Additional Exhaled Air Purification Units, filed Jul. 16, 2021.

U.S. Appl. No. 63/240,795, Exhaled Air Trap, filed Sep. 3, 2021.

U.S. Appl. No. 63/251,855, Computer Screen Comprising Exhaled Air Collector and Connected Air Purification Chamber, filed Oct. 4, 2021.

U.S. Appl. No. 63/271,933, Air Cleaning Computer Monitor, filed Oct. 26, 2021.

U.S. Appl. No. 63/272,907, Air Cleaning Computer Monitor, filed Oct. 28, 2021.

U.S. Appl. No. 63/283,524, Enhanced Air Cleaning Computer Monitor, filed Nov. 28, 2021.

The disclosures of those applications are hereby incorporated by reference herein in their entireties.

BACKGROUND OF THE INVENTION

Field of the Invention

The present invention is directed to an exhaled air purification unit and/or system providing an ability to capture, isolate, transport, and/or destroy airborne pathogens and contaminants and/or pollutants faster and/or more efficiently than currently available heating, ventilation, and air conditioning ("HVAC") systems, HVAC purification systems, and/or HVAC air handling systems, permit. By way of example only, airborne pathogens can float for over 15 minutes within a building traveling great distances before they are captured by the HVAC return. This is especially true for offices, auditoriums, theaters, and schools. It is estimated that about 70% of the day at school is spent sitting at a desk or table. As with offices, workplace, auditoriums, theaters, and school classrooms, many times the closest HVAC air return is across or far across the room from where the individual is seated. Thus, the exhaled air of multiple individuals must travel in the air across multiple rows of seats, desks, and/or tables before it is captured within the HVAC air return. It has been shown that increased ventilation resulting in reduced pollution, pathogens and lower $CO_2$ in the air can improve job and/or academic performance, productivity, and attendance. It is also known that individuals read comfortably at a distance within the near and intermediate viewing distance range with the appropriate optical prescription, if required. Thus, most computer monitor screens are located within the range of 16-36 inches from one's face, with many within the range of 18 to 22 inches.

Currently, upgraded HEPA filters are being added to many offices, schools, and universities' air handling systems and in many cases traditional air purifiers have been added to school classrooms and offices. While this will help somewhat in reducing pathogen spread, it will not adequately or sufficiently satisfy the need. Simply upgrading the HVAC system will not significantly reduce the potential of pathogen airborne contagious spread within a building or vehicle environment. There is a pressing need to capture, isolate and clean exhaled air of an individual much closer to the individual. By doing this, a cone of exhaled air from an individual is reduced (in cases, significantly reduced) in cubic area and diameter and it is possible to capture and/or isolate part of most of it, according to the current invention.

Description of the Related Art

Aerosol spray which transports viruses, including coronavirus ("COVID"), occurs from a human exhaled breath, talking, shouting, coughing, and sneezing. Under normal circumstances it is known that exhaled air forms a cone shape as it comes from the mouth and nose of an individual. Generally, at its origination at the nose and mouth it is approximately 55 mm in diameter. From there it usually (but not always) expands outward at 22 degrees-33 degrees and has a center trajectory of 10 degrees downward. The louder the noise the human makes with his or her voice, lungs, throat, or mouth, generally the farther the viral or bacterial aerosol is moved in the air. Recent studies show that an aerosol comprising viral float can remain airborne for up to 15 minutes in a closed confined environment. Research studies have showed that singing, yelling, coughing, and sneezing can spread COVID aerosol up to 3+ meters. By way of example only, COVID 19, COVID variants, coronavirus, measles, mumps, SARS, smallpox, common colds, influenza, and tuberculosis can be spread by way of being airborne. Closed confined multi-seated indoor environments are vulnerable to coronaviral spread. It has been proven that increased ventilation resulting in reduced pollution, pathogens and lower CO2 levels in the air can improve job and/or academic performance, productivity, and attendance. There is a need for capturing, isolating, and cleaning the exhaled air of individuals far more quickly and efficiently than what is done today with existing technology. One of the best-known and most efficient ways of eliminating CO2 is by way of plant photosynthesis.

$6CO_2$ (carbon dioxide)+$6H_2O$ (water) uses light to convert to $C6H_{12}O_6$ (sugar)+$6O_2$ (oxygen)

Plant cells perform the reactions of photosynthesis in as little as 30 seconds. Leaves tested processed 44.14 parts per million ("ppm") of carbon dioxide gas in each minute of photosynthesis for every gram of leaf surface. By example, if 44 ppm CO2 are used in photosynthesis, then the same amount of O2 is produced. Light, CO2 and water are needed for photosynthesis. Exhaled air is saturated with water. Exhaled air contains a maximum amount of moisture and therefore typically has a relative humidity of around 100%.

SUMMARY OF THE INVENTION

An embodiment of the present invention is that of an exhaled air collection system or apparatus including a computer monitor, wherein the computer monitor in addition to displaying images, comprises an exhaled air collector, wherein the computer monitor's computer screen forms an exhaled air blocking surface which is part of the exhaled air collector and wherein the exhaled air collector collects exhaled air, and the computer screen's surface deflects exhaled air towards an exhaled air suction intake. A computer monitor can comprise a flat or curved computer or television screen. A monitor can be a display screen. A display screen can be an electronic display screen. In aspects, a computer monitor represents the total display surface that comprises a computer screen and the outer peripheral covering thereof. In aspects, a computer monitor can also mean a computer screen and a computer screen can mean a computer monitor. In cases, one exhaled air suction intake (or a multiple air suction intakes) is/are located at or beneath a bottom or bottom portion of the computer monitor or computer screen. In other cases, one exhaled air suction intake or multiple intakes can be located around all or a portion of the periphery of the computer screen or computer monitor. When the air suction intake or intakes are located around a portion or all the periphery of computer monitor or computer screen, the air suction intake or intakes can be in the form of holes, apertures, or other openings. In still other cases, an exhaled air suction intake or intakes is/are located above the computer screen or computer monitor.

In aspects, an exhaled air suction intake can be covered by one or more of a screen, a mesh, a grid, a filter, CO2 reducer such as by way of example only, a living plant. In cases, the exhaled air suction intake is located at, around, or within an exhaled air catch basin. The exhaled air catch basin can be located at or below the bottom of the computer screen or computer monitor. The exhaled air catch basin can be located around all or a portion the periphery of the computer screen or computer monitor. In embodiments, the exhaled air catch basin can comprise a CO2 reducer such as, by way of example only, a living plant. In other embodiments, the exhaled air catch basin can be devoid of a living plant. The exhaled air catch basin can comprise one or more exhaled air suction intakes. The exhaled air catch basin is a design alternative and is optional. The one or more exhaled air suction intakes can be connected directly or indirectly to an exhaled air purification chamber. The indirect connection can be by way of example only, a conduit or an air suction conduit. The direct connection could be having the air purification chamber directly next to or adjacent to the exhaled air suction intake or exhaled air suction takes. The exhaled air purification chamber can comprise any mechanism known to destroy or remove pathogens from the air, such as, by way of example only, filter, HEPA filter, anti-microbial agent, microbicidal agent, microbicidal material, microbicidal light (such as by way of example only UVC light), microbicidal heat, or microbicidal ionization.

The exhaled air catch basin can comprise a fan or fans. The exhaled air catch basin can comprise a florescent light. The exhaled air catch basin can comprise a plant grow light. The bottom of the computer screen can comprise a florescent light. The bottom of the computer screen or any side thereof can comprise a plant grow light. The bottom of the computer monitor or any side thereof can comprise a florescent light. The bottom of the computer monitor or any side thereof can comprise a plant grow light. The exhaled air catch basin—can comprise a watering source. The exhaled air catch basin can comprise plant root nourishing material. The exhaled air catch basin can comprise one or more exhaled air suction intakes. The exhaled air collector and/or the computer monitor can comprise a CO2 monitor or sensor.

In one embodiment, a top surface or portion at, around, or above the computer screen or computer monitor can comprise a fan or fans. When multiple fans are utilized the top surface or portion at, around, or above a top edge of the computer screen can comprise or have attached a strip of multiple fans. In this embodiment the fan or fans can blow air downward across and/or in front of the computer screen or computer monitor. The downward air flow can assist in moving exhaled air flow of an individual using the computer monitor towards or into an exhaled air suction intake or exhaled air catch basin. In other embodiments there is no fan or fans above or attached to the computer monitor that form an air curtain pushing exhaled air downward. In these cases, the embodiments rely upon the trajectory and shape of the cone of exhaled air, gravity, and distance from the computer monitor's screen from which the user is sitting or standing.

In preferred embodiments, whether fans are present to blow the exhaled air downward or not, the trajectory and shape of the cone of exhaled air, gravity, and distance from the computer monitor's screen from which the user is sitting or standing (and especially the mouth and nose of the user) is used by the present invention to influence the percentage of capture and collection of exhaled air of the user by the system or apparatus, including the computer monitor's exhaled air collector. In addition, the height of the user's head and/or body relative to the middle of the computer monitor screen, as well as the angle of the computer monitor with respect to the horizontal top of the table on which it rests, is used by the current invention to influence an amount of the exhaled air that will be deflected above or below the computer monitor. In embodiments the amount of CFM of air that is sucked in or the CARR of air that is removed from the air purification chamber influences the effectiveness of the amount of exhaled air that is captured and cleaned. In preferred embodiments, when the computer monitor screen's lower front is angled closer to the user than its top, the air suction intake at the bottom of the computer monitor will capture the largest percentage of the exhaled air of the user.

In cases, the exhaled air suction intake can be located at a location at the bottom of or under the computer screen or computer monitor. In other cases, the exhaled air suction intake can be located under the computer screen and within the lower portion of the computer monitor. In still other cases, the exhaled air suction intake can be located within an exhaled air catch basin located at the bottom of or under the computer screen or computer monitor. And in still other cases, the exhaled air suction intake can be located within an exhaled air catch basin located at the bottom of or under the computer screen and within a lower section of the computer monitor.

There can be one or multiple air suction intakes. In embodiments, the air suction intake circumvents the computer screen and/or computer monitor. (See, e.g., FIG. 29, FIG. 30.) In cases where the computer monitor includes an exhaled air collector integrated with or within its housing (meaning the exhaled air collector is built into or around the computer monitor), the exhaled air suction intake can be around the outer edge of the screen or one or more portions of the outer edge of the screen. (See, e.g., FIG. 4., FIG. 30.) In cases where the exhaled air collector is later attached to a computer monitor (e.g., retrofitted), or where the exhaled air collector is integrated onto the outside of the computer monitor, the exhaled air suction intake can be located around the outer edge of the computer monitor or one or more portions of the outer edge of the computer monitor, outer edge of display screen or one or more portions of the display screen. (See, e.g., FIG. 4, FIG. 30.)

A fan or multiple fans can be located within the exhaled air catch basin. A fan or multiple fans can be located within or adjacent to the exhaled air suction intake. A fan or fans can be located within the air purification chamber. An exhaled air suction intake can connect directly or indirectly to an exhaled air purification chamber. The air suction of the air purification chamber can pull the exhaled air (and room air) into the exhaled air purification chamber where it is cleaned and then, in cases, released back into the room.

In another embodiment, a top surface or portion at or above the computer screen of a computer monitor can comprise a fan or fans. When multiple fans are utilized the top surface or portion at or above the top edge of the computer screen, the exhaled air collector can comprise or have attached a strip of multiple fans. The fan, fans, or fan strip can generate an air curtain of air flow. In this embodiment, the fan, fans, or fan strip can blow air downward across and/or in front of the computer screen or computer monitor. (See, e.g., FIG. 21, FIG. 24.) The downward air flow according to the present invention can assist in moving exhaled air flow of an individual using the computer monitor downward towards or into an exhaled air suction intake or intakes and/or exhaled air catch basin. In cases, the exhaled air suction intake or intakes can be located at a location under the computer screen or computer monitor. In other cases, the exhaled air suction intake or intakes can be located under the computer screen and within the lower portion of the computer monitor. In other cases, an air purification chamber can be located at or below the computer screen or the bottom of the computer monitor. In other cases, an air purification chamber can be located at or below the computer screen or within a lower portion of the computer monitor. The air purification chamber can comprise air suction, thus pulling the exhaled air (and room air) downward into the air purification chamber. The air purification chamber can be located under the computer screen or computer monitor and/or it can make up a portion of the exhaled air collector. The air purification chamber can be located at a bottom of the computer monitor or computer screen. In aspects, the point/place where the downward air flow and/or exhaled air of the user of the computer monitor enters the air purification chamber becomes that of the exhaled air suction intake. Thus, in this embodiment, downward air flow from one or more fans (e.g., blowing downward and/or suctioning downward) moves exhaled air and/or room air towards an exhaled air purification chamber that is located at or under the lower edge of the computer screen, or at or around the bottom of the computer monitor or computer screen. The air purification chamber can be built into the computer monitor. A filter or filters, by way of example only, HEPA filter(s), can be located on the inside of the back surface of the back. An exhaust fan or fans can be located on the inside of the back surface of the back or on the outside of the back surface of the back. (See, e.g., FIG. 5, FIG. 11, FIG. 12, FIG. 13, FIG. 31, FIG. 32, FIG. 33, FIG. 34, FIG. 35.) The filter or filters are located forward (closer to the front of the monitor or screen) to that of the fan or fans, in aspects. The fan or fans pull non-cleaned air through the filter(s) before it is released back into the venue. The upper fan, fans, or fan strip can be built into the computer monitor. A lower fan, fans, or fan strip, if utilized and present, can be built into the computer monitor. The exhaled air purification chamber can be independent of the computer monitor. The exhaled air purification chamber can be independent but attached to the computer monitor. The air suction of the exhaled air purification chamber can pull the exhaled air (and room air) into the exhaled air purification chamber where it is cleaned and then, in cases, released back into the room.

In still another embodiment, a top surface or portion at or above the computer screen of a computer monitor (including at or near the top of the computer screen) can comprise a fan or fans. When multiple fans are utilized the top surface or portion at or above the top edge of the computer screen can comprise or have attached a strip of multiple fans. In this embodiment, the fan, fans, or strip of fans can blow air downward across and/or in front of the computer screen or computer monitor. The downward air flow can assist in moving exhaled air flow of an individual using the computer monitor towards or into an exhaled air suction intake that is at the entry of, or within, an exhaled air catch basin. A fan or multiple fans can be located at the entry of, or within, the exhaled air catch basin. A fan or multiple fans can be located within or adjacent to the exhaled air suction intake. An exhaled air suction intake can connect directly or indirectly to an exhaled air purification chamber. An air suction intake can pull in exhaled air and room air into the intake. The air suction of the air purification chamber can pull the exhaled air and room air into the exhaled air purification chamber where it is cleaned and then released, in cases, back into the room. In embodiments, the exhaled air catch basin can comprise a $CO_2$ reducer, such as by way of example only, a living plant or plant. In other embodiments, the exhaled air catch basin is devoid of a $CO_2$ reducer.

When an exhaled air catch basin is present, one or more living plants can be located within the exhaled air catch basin. In other cases, one or more living plants can be in front of an exhaled air suction intake. In still other cases, a $CO_2$ reducer, such as by way of example only, one or more living plants, can form a grid, grate, or cover over the exhaled air suction intake. In still other cases, a $CO_2$ reducer, such as by way of example only, one or more living plants, can form a lining of a prefilter for the exhaled air collector. When a plant or plants is/are utilized, the plant or plants can be positioned before the air flow strikes or meets a filter or a main filter (such as, by way of example only, a HEPA filter) of the air purification chamber. The living plant or plants can be, by way of example only, one or more of moss, ivy, spinach, pothos, or cactus. There are particular green leafed plants that photosynthesize faster or more efficiently than other plants. The living plant or plants can remove by photosynthesis a portion of the CO2 in the exhaled air breath of a user of the computer monitor and a portion of the CO2 that is located within the room air of the room in which the computer monitor is located. Thus, in embodiments, the exhaled air collector combined with the exhaled air purification chamber (in aspects, called together an "exhaled air purification unit" or "air purification unit") can clean the room air and/or exhaled air of pathogens, contaminants, or particulates, or reduce CO2, and combinations thereof. In summary, downward air flow combined with exhaled air flows through and/or over one or more live plants and into an exhaled air suction intake. From there, it can flow directly or indirectly into an air purification chamber, or indirectly into an air conduit and into an air purification chamber before being further cleaned and released back into the room. In other embodiments, external fans on the exhaled air collector are not present and the user's exhaled air flow velocity and trajectory combined with the exhaled air suction intake pulls deflected and non-deflected exhaled air through the CO2 reducer (if present) into the exhaled air suction intake. (Deflected, directed, or redirected, in aspects, can mean exhaled air that strikes the computer monitor's screen and is deflected towards the exhaled air suction intake.)

In another embodiment, one or more CO2 reducers such as, by way of example only, one or more of CO2 absorbing materials, CO2 being absorbed and reclaimed with Nitrogen, passing air through a stack of charged electrochemical plates, or a living plant or plants, which can be located anywhere within the air purification unit or air purifier, can be located at a position before the air flow strikes the main filter (such as, by way of example only, a HEPA filter) of the air purification chamber. Thus, in this embodiment, the exhaled air collector combined with the exhaled air purification chamber (called together an exhaled air purification unit) can clean the room air and exhaled air of pathogens and CO2. In summary, downward air flow (if present) combined with exhaled air flows through, into, and/or over a CO2 reducer before striking the main air purification's filter. The CO2 reducer can be incorporated within one of the computer monitor, the air purification chamber, attached to the computer monitor, within an exhaled air catch basin, and/or free standing in front of an air suction intake of the exhaled air purification unit.

While each of the preceding embodiments teach a fan, fans, or strip of fans located at a top of or above the top edge of the computer screen to move air downward, in embodiments no such fan, fans, or strip of fans is present. These embodiments can, in aspects, utilize a velocity and/or trajectory of the user's exhaled air and the exhaled air blocking surface of the computer screen to deflect the exhaled air downward towards an air suction intake or that of the exhaled air purification chamber. The exhaled air suction intake can be located adjacent to or close to that of a CO2 reducer.

BRIEF DESCRIPTION OF THE DRAWINGS

The accompanying drawings illustrate certain aspects of some of the embodiments of the present invention and should not be used to limit or define the invention. Together with the written description the drawings serve to explain certain principles of the invention.

DETAILED DESCRIPTION

Figure 1:
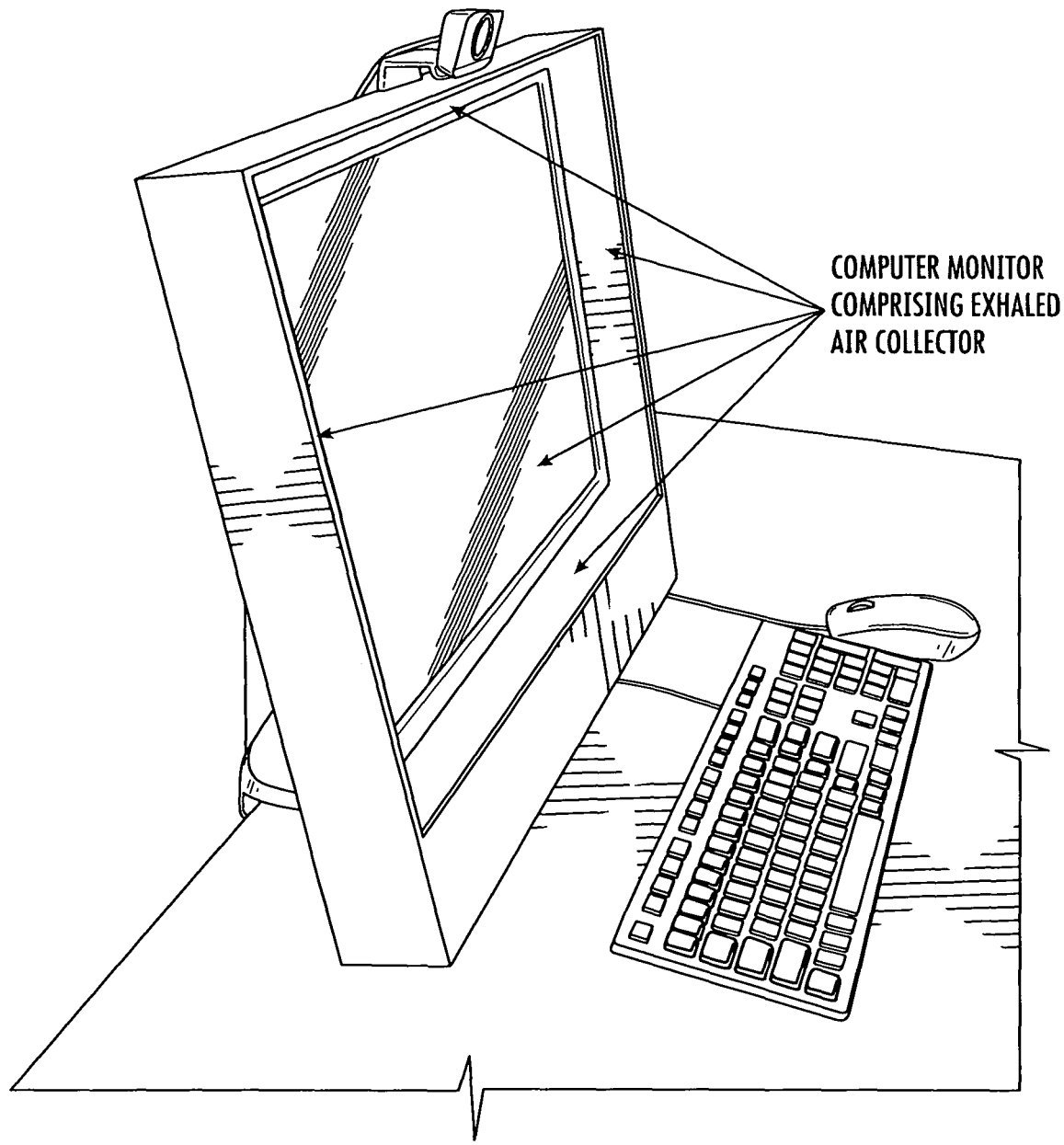
FIG. 1 is a depiction of an embodiment of the current invention, such as a computer monitor with exhaled air collector and air purification chamber (not visible in this depiction).

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Embodiments comprising various features may also consist of or consist essentially of those various features. Other embodiments of the invention will be apparent to those skilled in the art from consideration of the specification and practice of the invention. The description of the invention provided is merely exemplary in nature and, thus, variations that do not depart from the essence of the invention are intended to be within the scope of the invention.

All references cited in this specification are hereby incorporated by reference in their entireties.

Various Embodiments/Examples

The following embodiments should be read having a fan, fans, or fan strip located at the top of or above the computer screen of the computer monitor (e.g., examples #1-#11), and/or without a fan, fans, or fan strip located at the top of or above the computer screen of the computer monitor (e.g., examples #12-#22).

1) Downward air flow moves exhaled air of a user of the computer monitor>towards or into an air suction intake>directly connected to an air purification chamber;
2) Downward air flow moves exhaled air of a user of the computer monitor>towards or into an air suction intake>indirectly connected to an air purification chamber by a conduit;
3) Downward air flow moves exhaled air of a user of the computer monitor>towards or into an air suction intake of the air purification chamber;
4) Air flow moves exhaled air of a user of the computer monitor>towards or into an exhaled air catch basin>then is moved into an exhaled air suction intake>then is moved directly or indirectly into an air purification chamber;
5) Air flow moves exhaled air of a user of the computer monitor>towards or across a living plant or plants (or another type of CO2 reducer)>and then towards or into an air suction intake>then is moved directly connected to an air purification chamber;
6) Air flow moves exhaled air of a user of the computer monitor>towards or across a living plant or plants (or another type of CO2 reducer)>towards or into an air suction intake>directly connected to an air purification chamber;
7) Air flow moves exhaled air of a user of the computer monitor>towards or across a living plant or plants (or another type of CO2 reducer)>towards or into an air suction intake>indirectly connected to an air purification chamber by a conduit;
8) Air flow moves exhaled air of a user of the computer monitor>towards or across a living plant or plants (or another type of CO2 reducer)>towards or into an air suction intake of the air purification chamber;
9) Air flow moves exhaled air of a user of the computer monitor>towards or across a living plant or plants (or another type of CO2 reducer)>towards or into an air purification chamber;
10) Air flow moves exhaled air of a user of the computer monitor>towards or into an exhaled air catch basin comprising a living plant or plants (or another type of CO2 reducer)>then is moved into an exhaled air suction intake>then is moved directly or indirectly into an air purification chamber;
11) Air flow moves exhaled air of a user of the computer monitor>towards or across a living plant or plants (or another type of CO2 reducer)>and then towards or into an air suction intake>then is moved directly connected to an air purification chamber;
12) Exhaled air of a user of the computer monitor>flows towards or into an air suction intake>directly connected to an air purification chamber.
13) Exhaled air of a user of the computer monitor>flows towards or into an air suction intake>indirectly connected to an air purification chamber by a conduit;
14) Exhaled air of a user of the computer monitor>flows towards or into an air suction intake of the air purification chamber;
15) Exhaled air of a user of the computer monitor>flows towards or into an exhaled air catch basin>then is moved into an exhaled air suction intake>then is moved directly or indirectly into an air purification chamber;
16) Exhaled air of a user of the computer monitor>flows towards or across a living plant or plants (or another type of CO2 reducer)>and then towards or into an air suction intake>then is moved directly connected to an air purification chamber;
17) Exhaled air of a user of the computer monitor>flows towards or across a living plant or plants (or another type of CO2 reducer)>and then towards or into an air purification chamber;
18) Exhaled air of a user of the computer monitor>flows towards or across a living plant or plants (or another type of CO2 reducer)>towards or into an air suction intake>directly connected to an air purification chamber;

19) Exhaled air of a user of the computer monitor>flows towards or across a living plant or (or another type of CO2 reducer) plants>towards or into an air suction intake>indirectly connected to an air purification chamber by a conduit;

20) Exhaled air of a user of the computer monitor>flows towards or across a living plant or plants (or another type of CO2 reducer)>towards or into an air suction intake of the air purification chamber;

21) Exhaled air of a user of the computer monitor>flows towards or into an exhaled air catch basin comprising a living plant or plants (or another type of CO2 reducer) >then is moved into an exhaled air suction intake>then is moved directly or indirectly into an air purification chamber;

22) Exhaled air of a user of the computer monitor>flows towards or across a living plant or plants (or another type of CO2 reducer)>and then towards or into an air suction intake>then is moved directly connected to an air purification chamber.

While the invention contemplates different combinations of the above embodiments, in a preferred embodiment, when CO2 is removed from the air flow, this occurs prior to the air flow striking or entering the filtering portion of the air purification chamber, such as by way of example only, a HEPA filter. In aspects, the location of the CO2 reducer being placed prior to a filtering portion of the air purification chamber is so that the filtering portion of the air purification chamber can remove any particulates that may be created or generated by the CO2 reducer before the air is released back into the room or venue.

Figure 7:
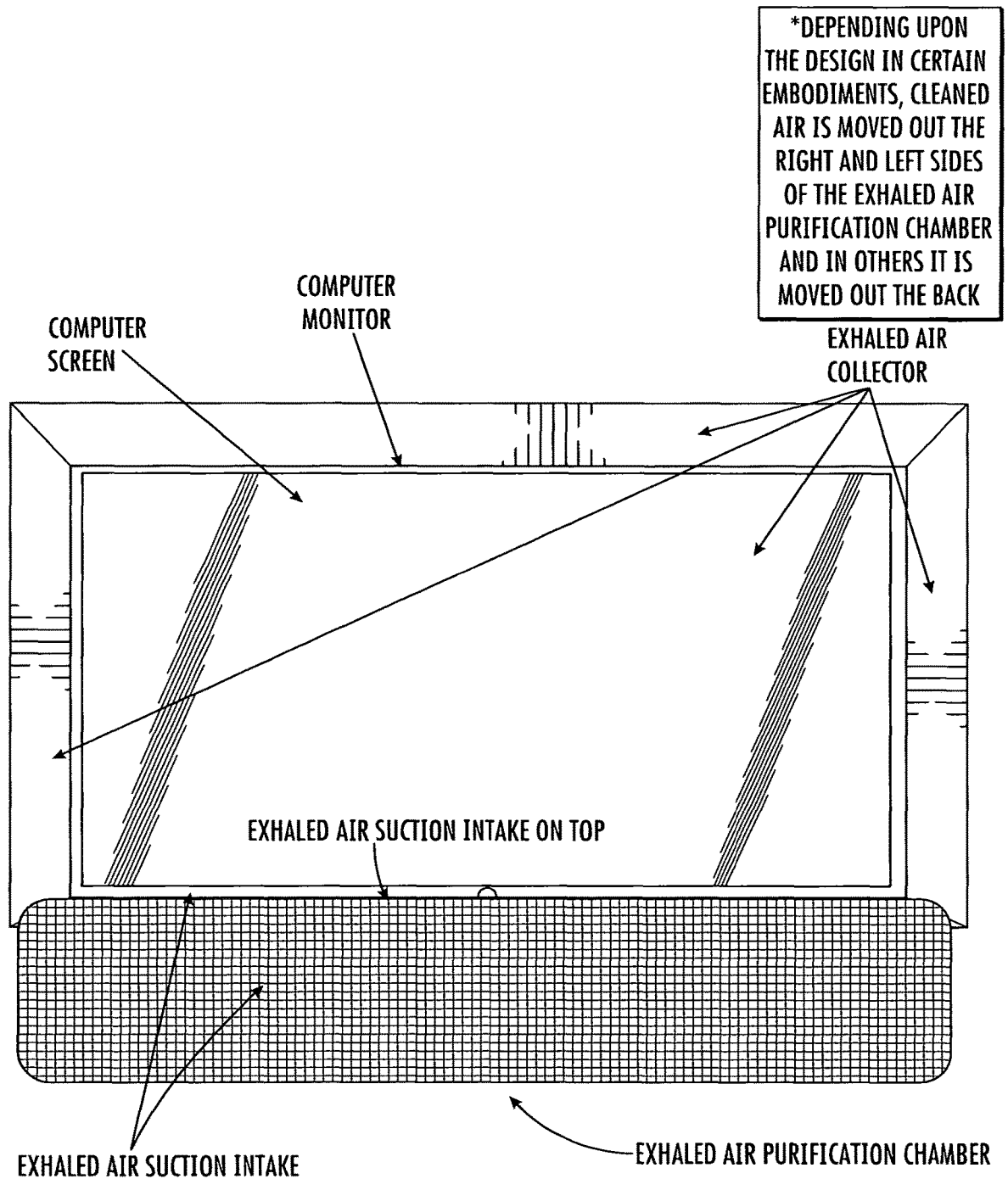
FIG. 7 is a depiction of an embodiment of the current invention, showing a monitor with an attached exhaled air purification unit.
Figure 8:
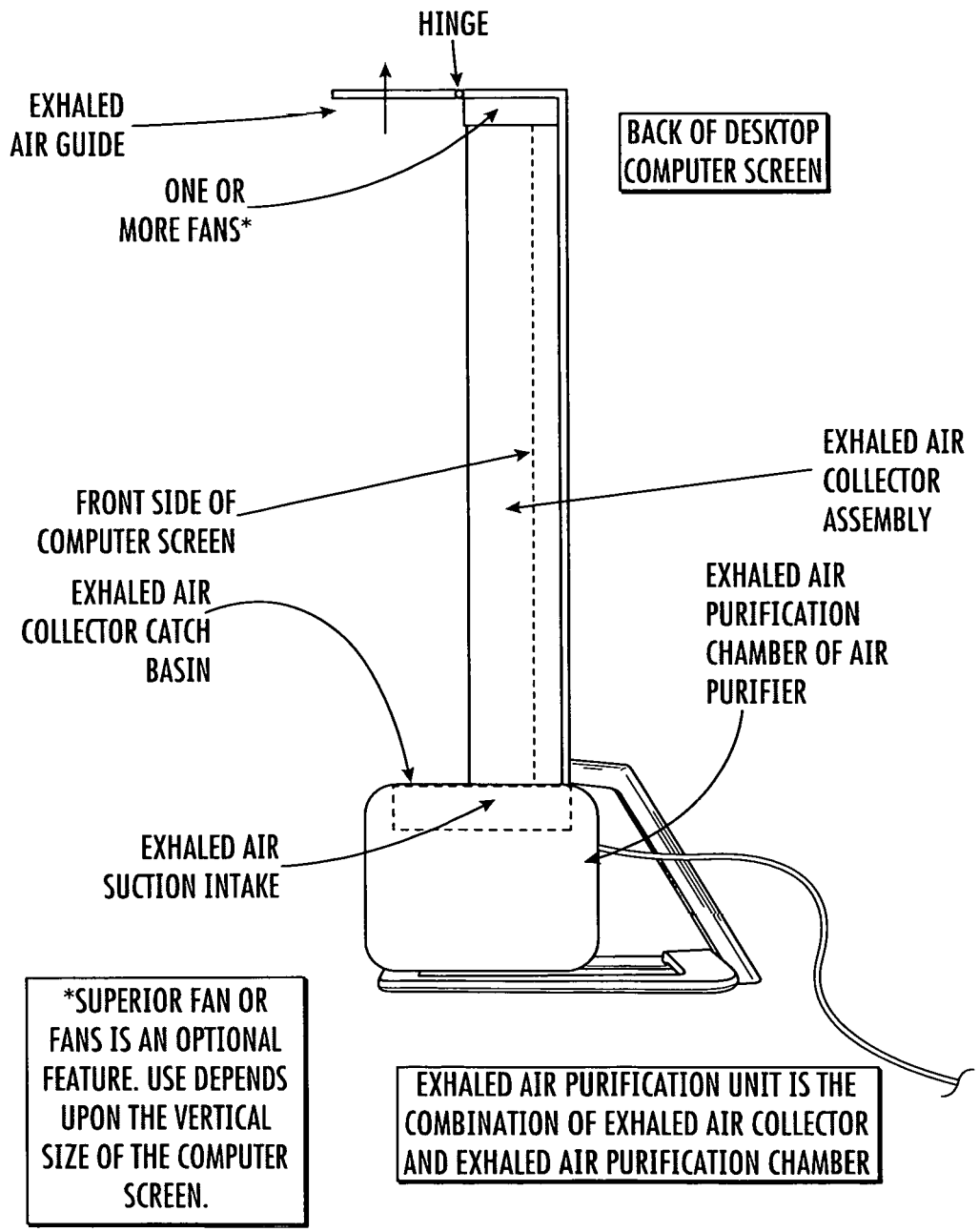
FIG. 8 is a depiction of an embodiment of the current invention, showing a monitor with an integrated exhaled air purification unit.
Figure 10:
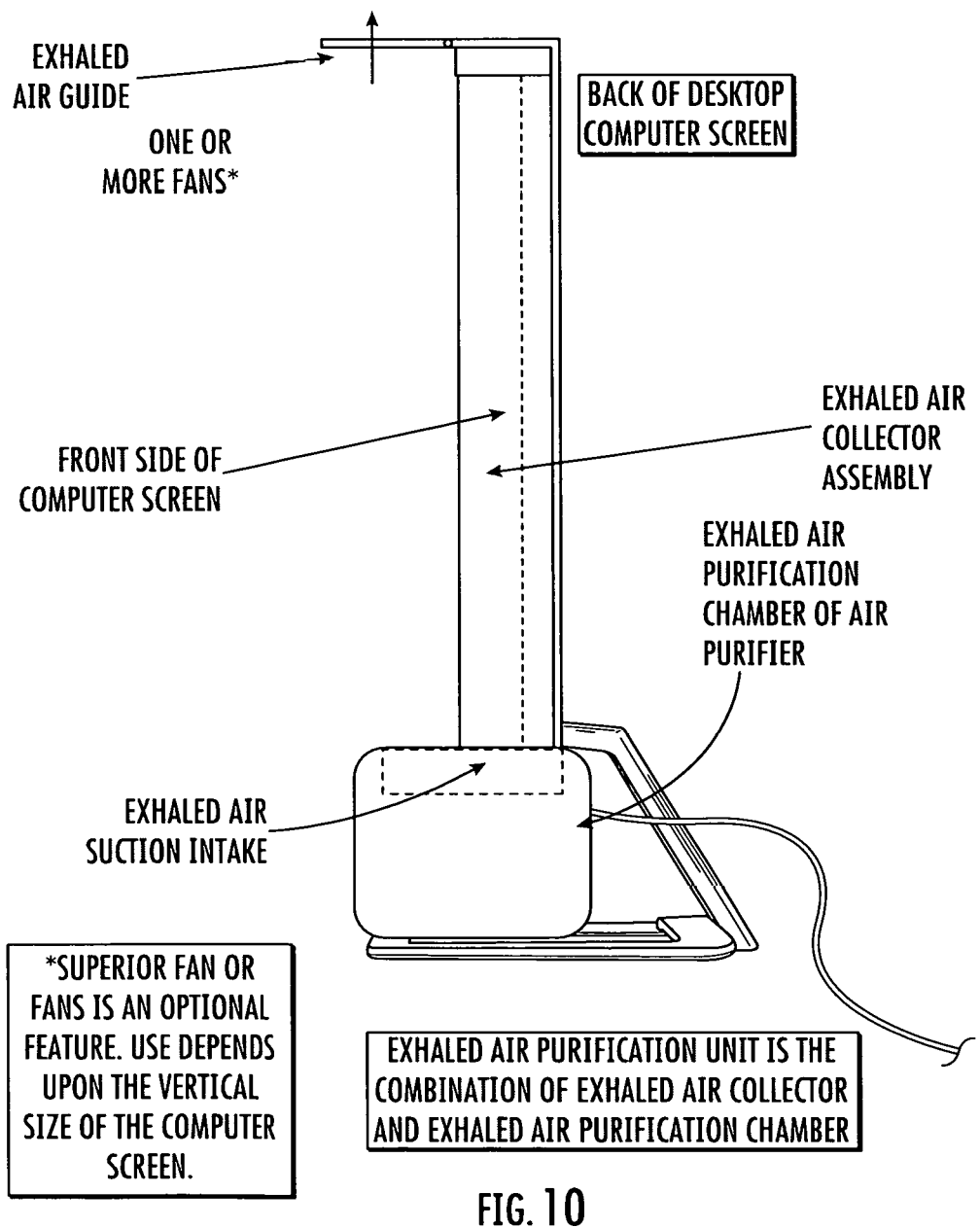
FIG. 10 is a depiction of an embodiment of the current invention, showing a monitor with a retrofitted/attached exhaled air purification unit. In aspects, the superior fan or fans are an optional feature; use of the fan or fans depends on, for example, the vertical size/dimension(s) of the computer screen.
Figure 11:
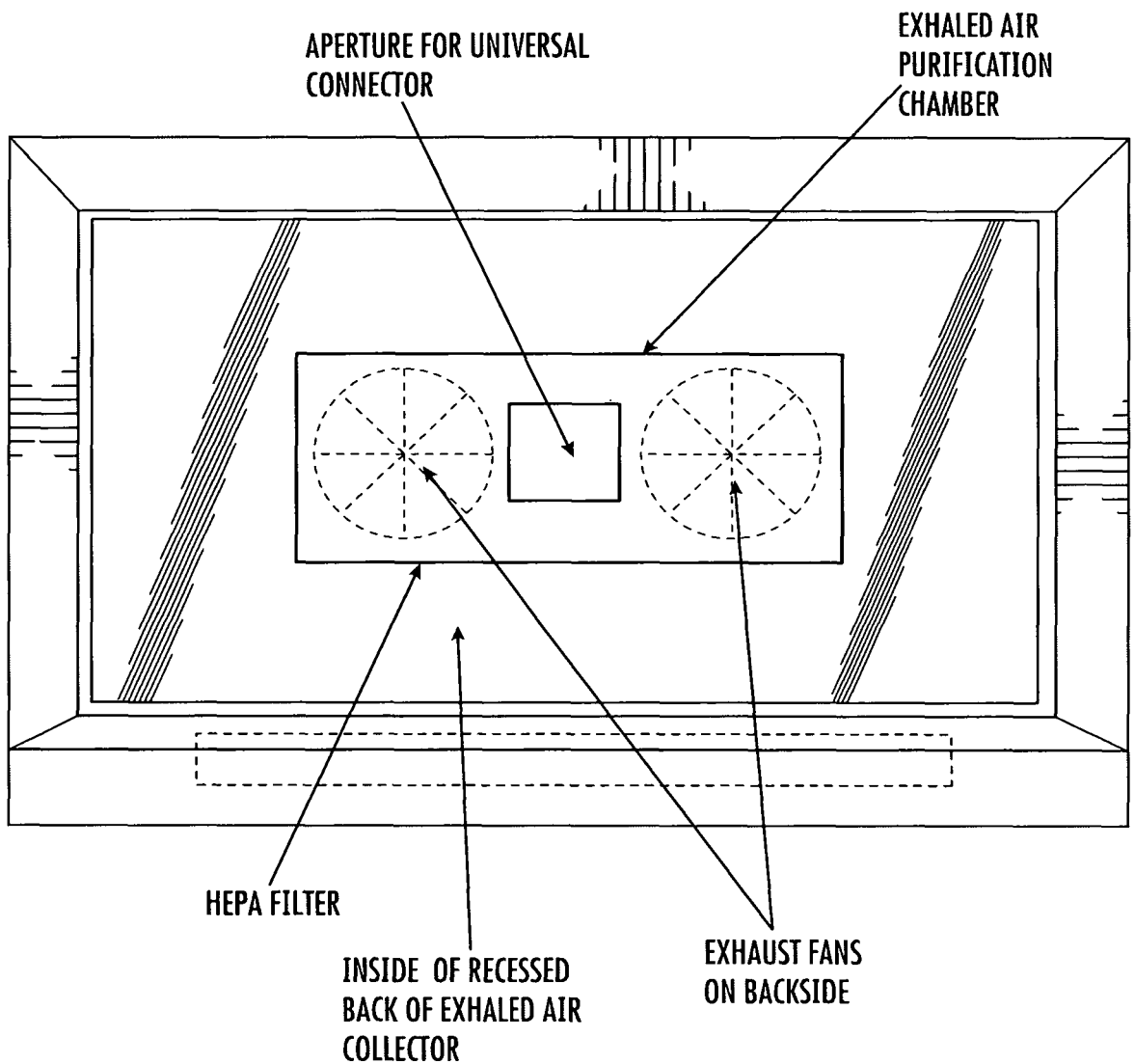
FIG. 11 is a depiction of an embodiment of the current invention, showing a monitor with a retrofit-able exhaled air purification unit assembly for a monitor.
Figure 12:
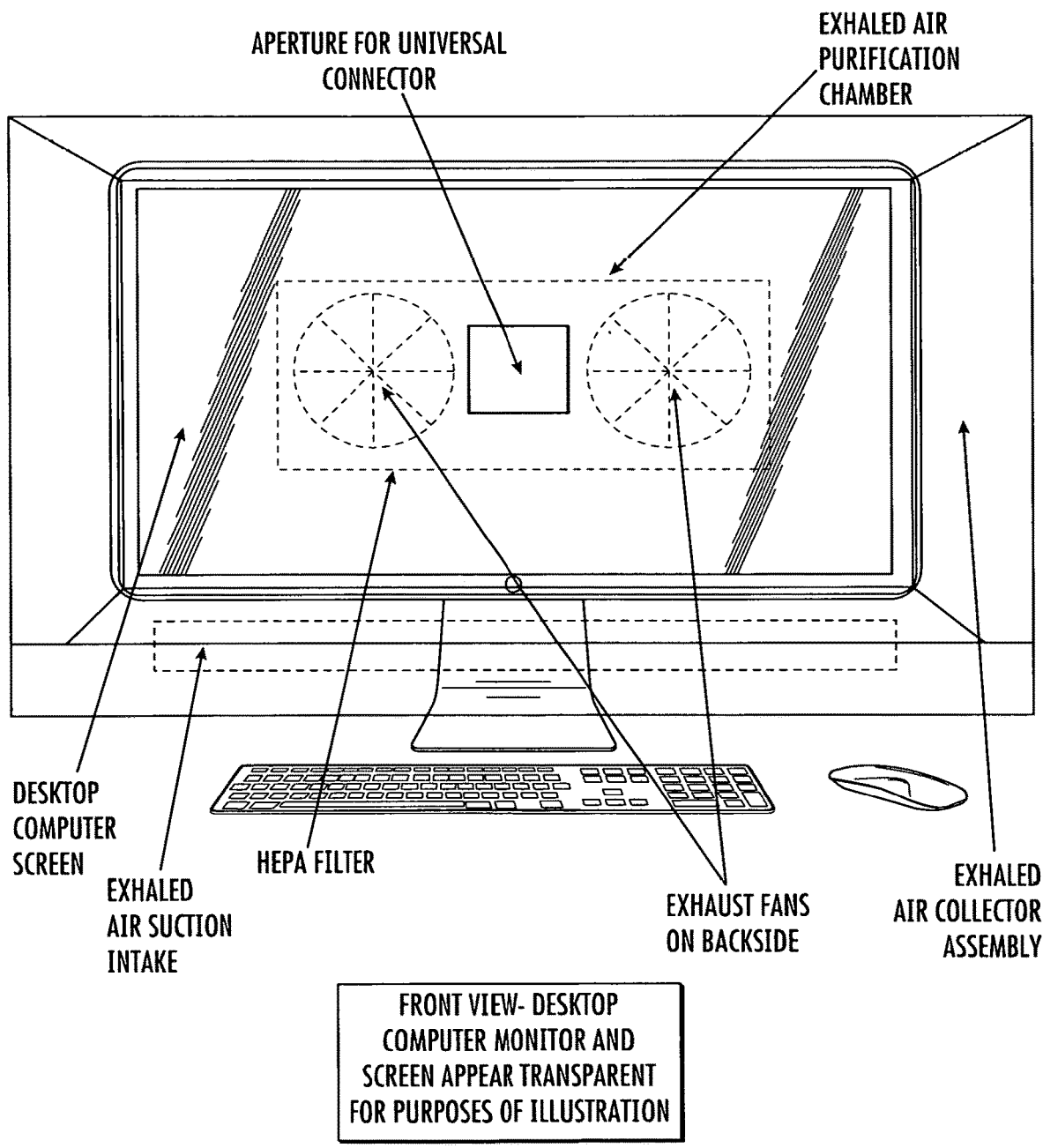
FIG. 12 is a front-view depiction of an embodiment of the current invention, showing a monitor with an attachable exhaled air collector attached.
Figure 13:
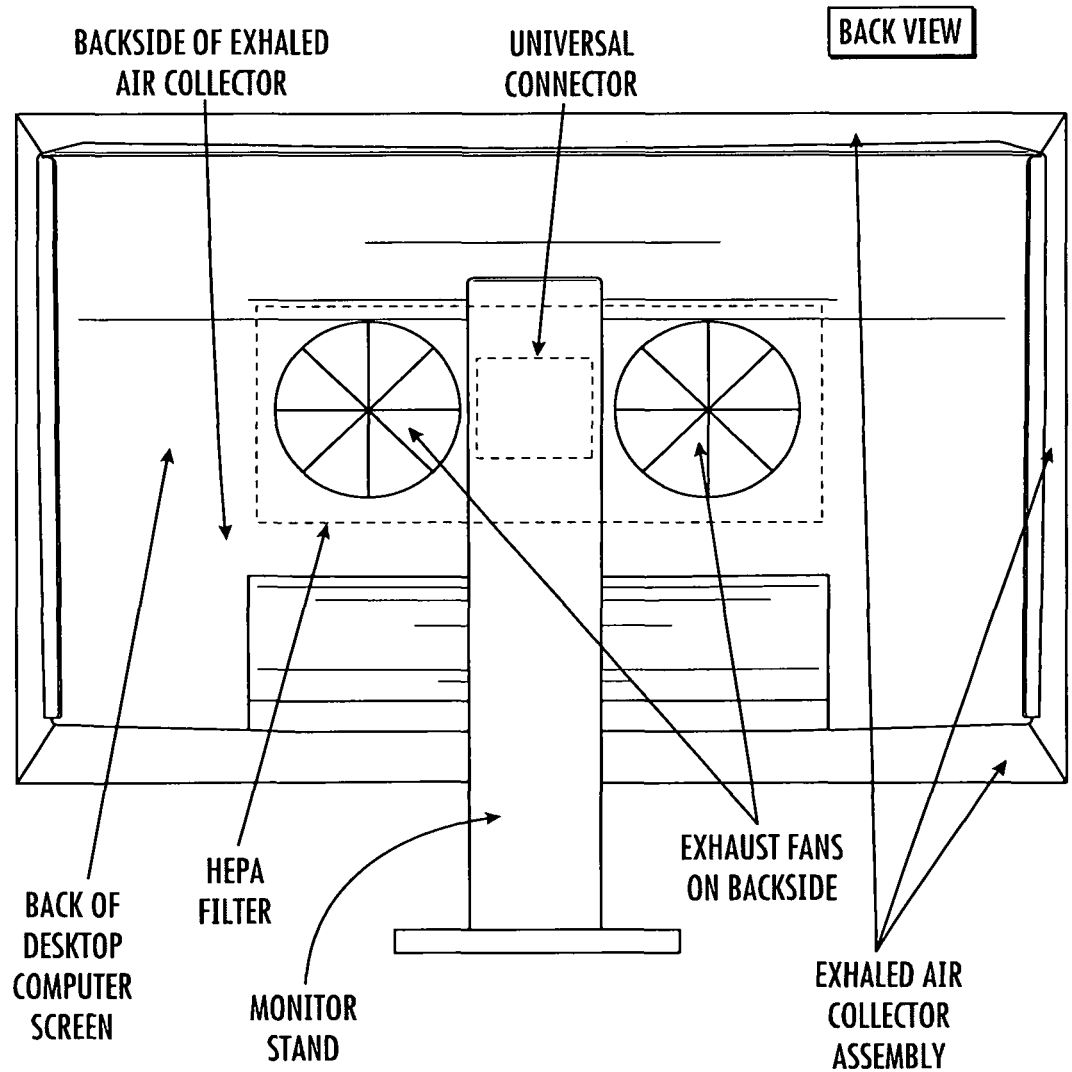
FIG. 13 is a back-view depiction of an embodiment of the current invention, showing a monitor with an attachable exhaled air collector attached.
Figure 14:
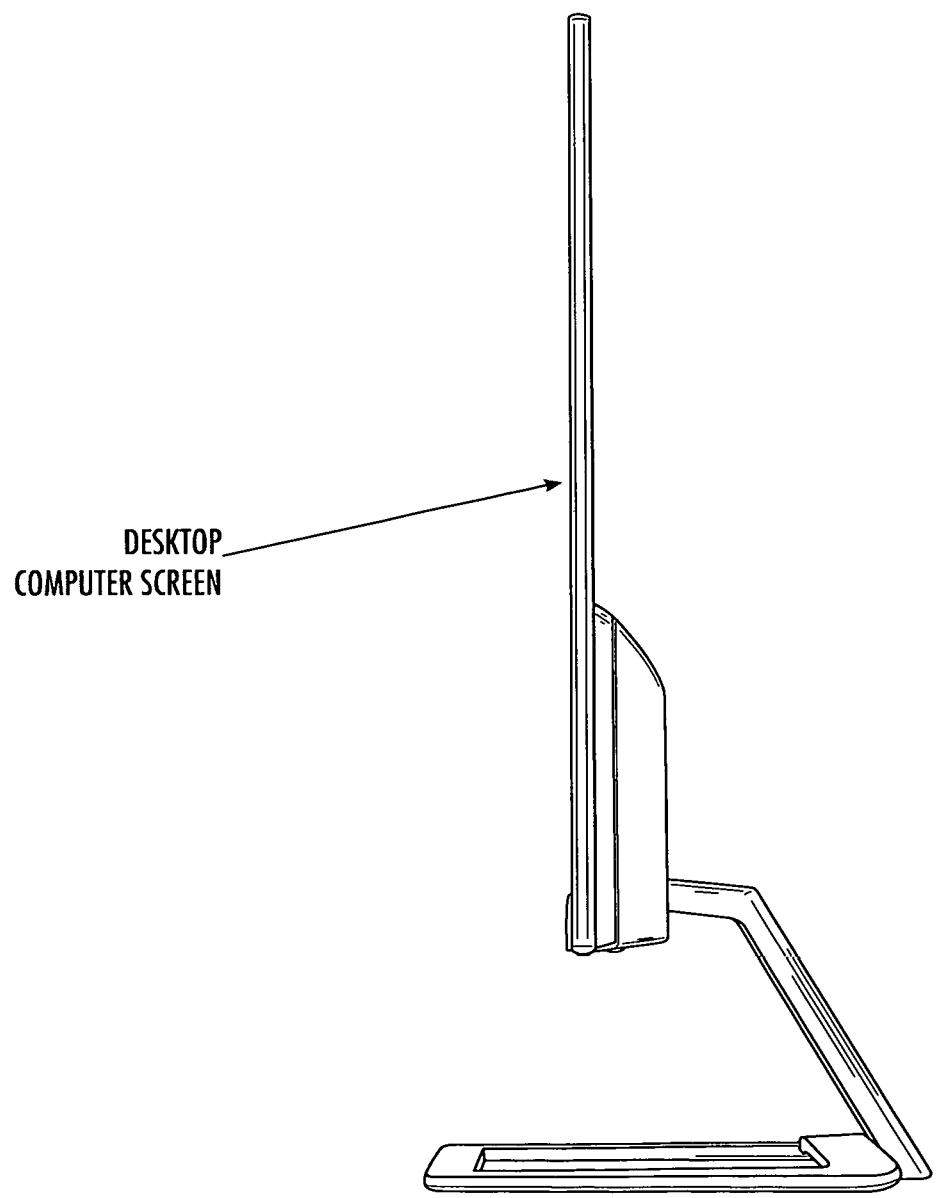
FIG. 14 shows a desktop computer monitor having a computer monitor display screen/electronic display screen.
Figure 26:
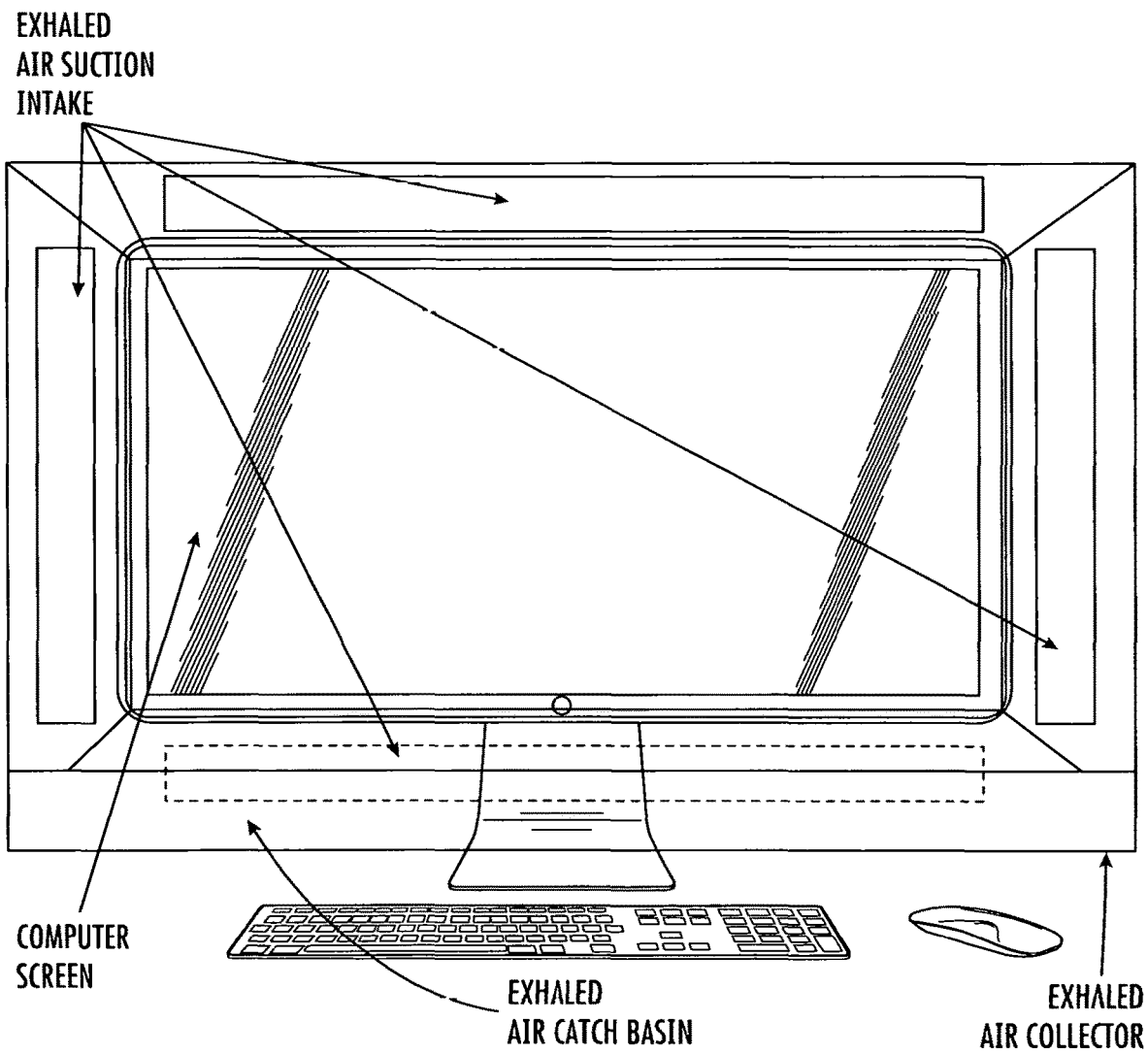
FIG. 26 is a depiction of an embodiment of the current invention, showing a monitor with an attachable exhaled air collector as attached to a monitor.

Exhaled air>CO2 reducer>Filter (by way of example only, HEPA filter)>Cleaned air In embodiments, the exhaled air collector can be attachable to the computer screen or computer monitor. In embodiments, the exhaled air collector can be attachable and detachable to the computer screen or computer monitor, such as releasably attachable for example. When attachable to the computer screen or computer monitor, the exhaled air collector can be an exhaled air collector assembly. When attachable to the computer screen or computer monitor, the exhaled air collector can be an exhaled air collector assembly kit. In other embodiments, the exhaled air collector can be designed into the computer screen or computer monitor. And in still other embodiments, the exhaled air collector can be integrated with or designed into the computer screen or computer monitor. (See, e.g., FIG. 6, FIG. 8, FIG. 19, FIG. 20, FIG. 21, FIG. 22, FIG. 23, FIG. 25.) In embodiments, the exhaled air collector can be designed into or integrated with a computer monitor or display screen stand. (See, e.g., FIG. 31, FIG. 32, FIG. 33, FIG. 34.) In embodiments, the exhaled air collector can be attached to a computer monitor or display screen stand. In embodiments, the exhaled air collector can be releasably attachable to a computer monitor or display screen stand. (See, e.g., FIG. 7, FIG. 10, FIG. 26.)

The computer screen or computer monitor can be or comprise one of a desktop computer screen, a laptop computer screen, a tablet computer screen, a cellphone screen, a mobile phone screen, and/or an exercise screen used with physical workout equipment. The computer screen or computer monitor can display digital images, words, and/or numbers generated by a wired or wireless connected computer, while at the same time capture exhaled air of the user of the computer and/or monitor/screen. In embodiments, an exhaled air purification chamber can be attachable (such as releasably attachable) to a computer screen or computer monitor. In embodiments, an exhaled air purification unit can be attachable (such as releasably attachable) to a computer screen or computer monitor.

Figure 17:
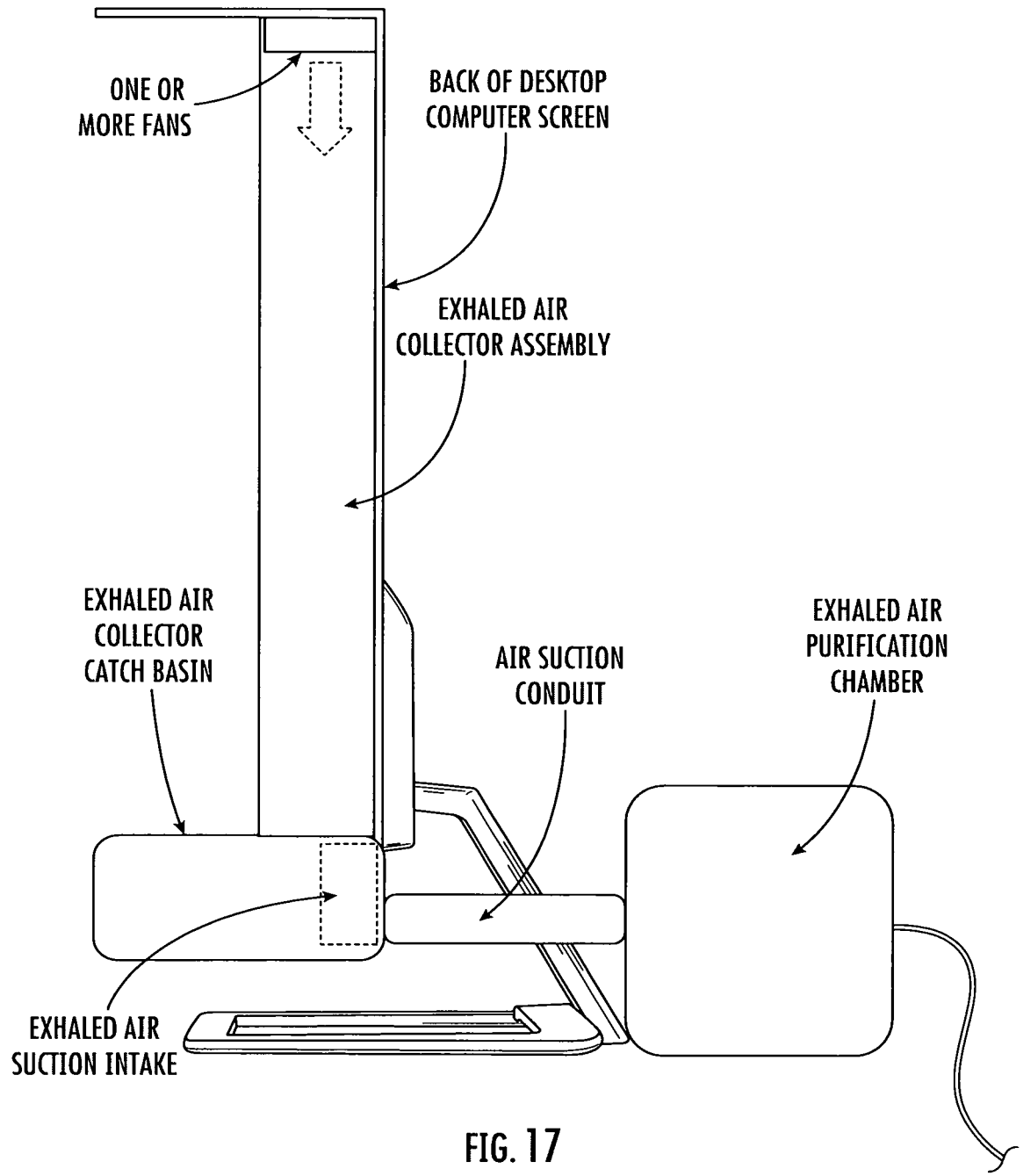
FIG. 17 is a depiction of an embodiment of the current invention, showing a monitor with a retrofitted exhaled air purification unit.
Figure 18:
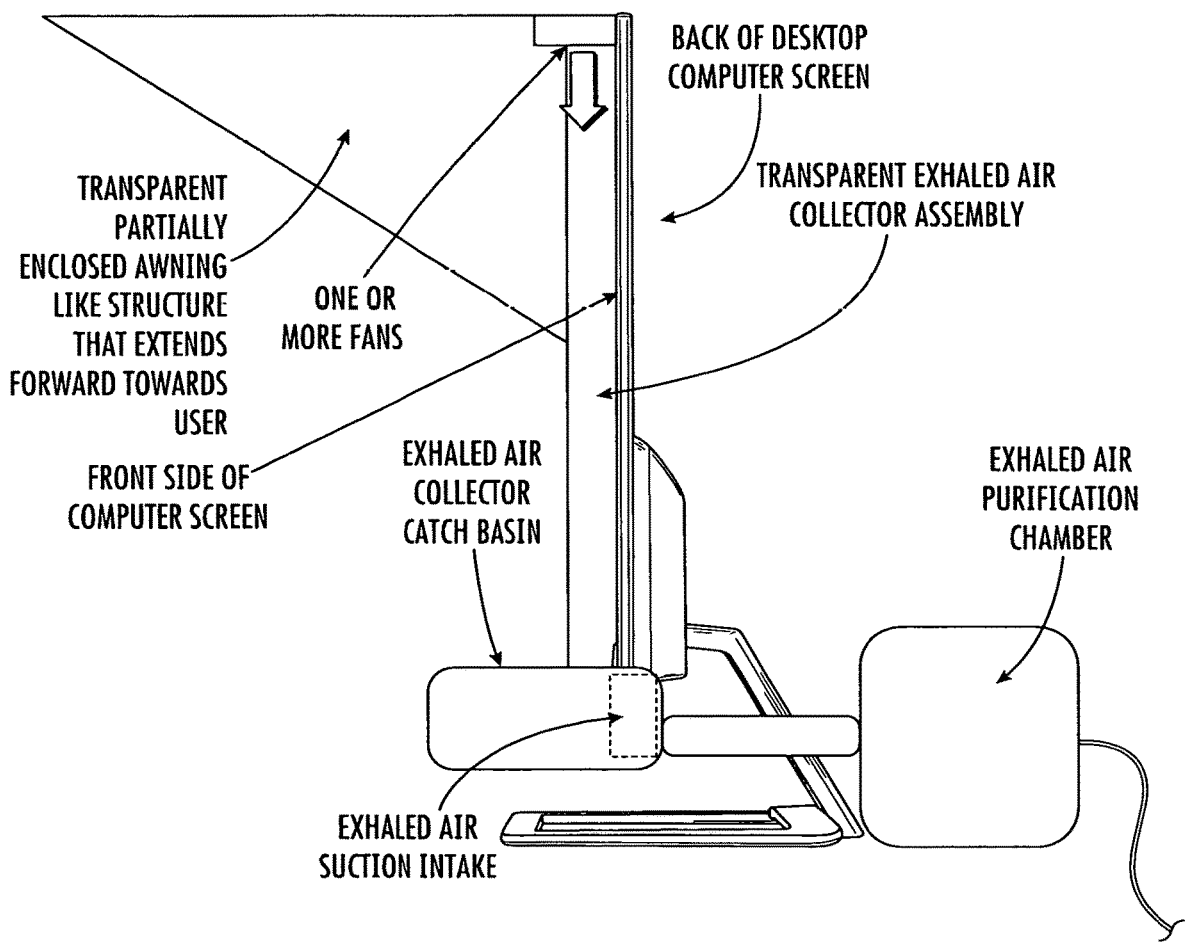
FIG. 18 is a depiction of an embodiment of the current invention, showing a monitor with a retrofitted exhaled air purification unit.
Figure 19:
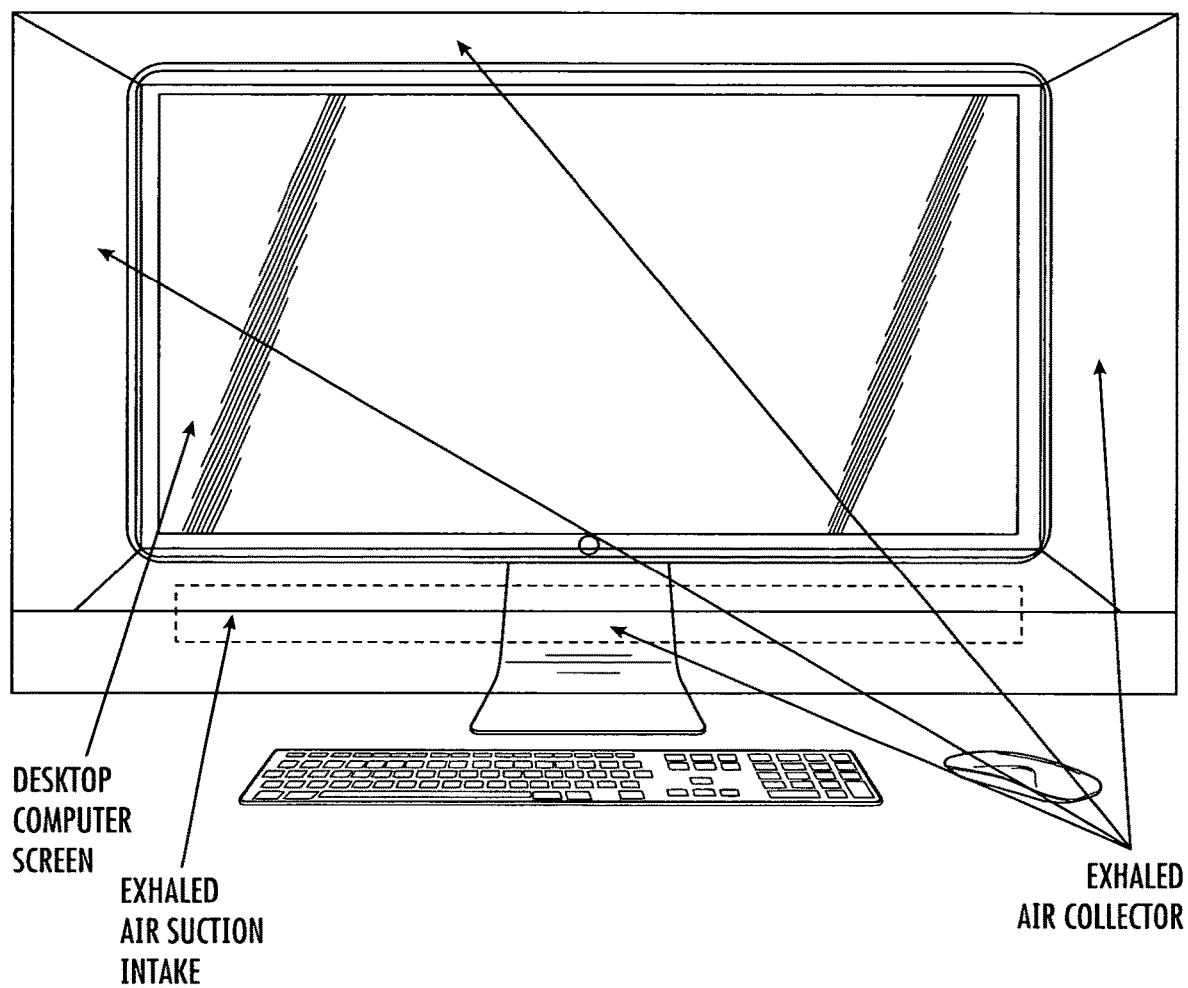
FIG. 19 is a depiction of an embodiment of the current invention, showing a monitor with an integrated exhaled air collector.
Figure 20:
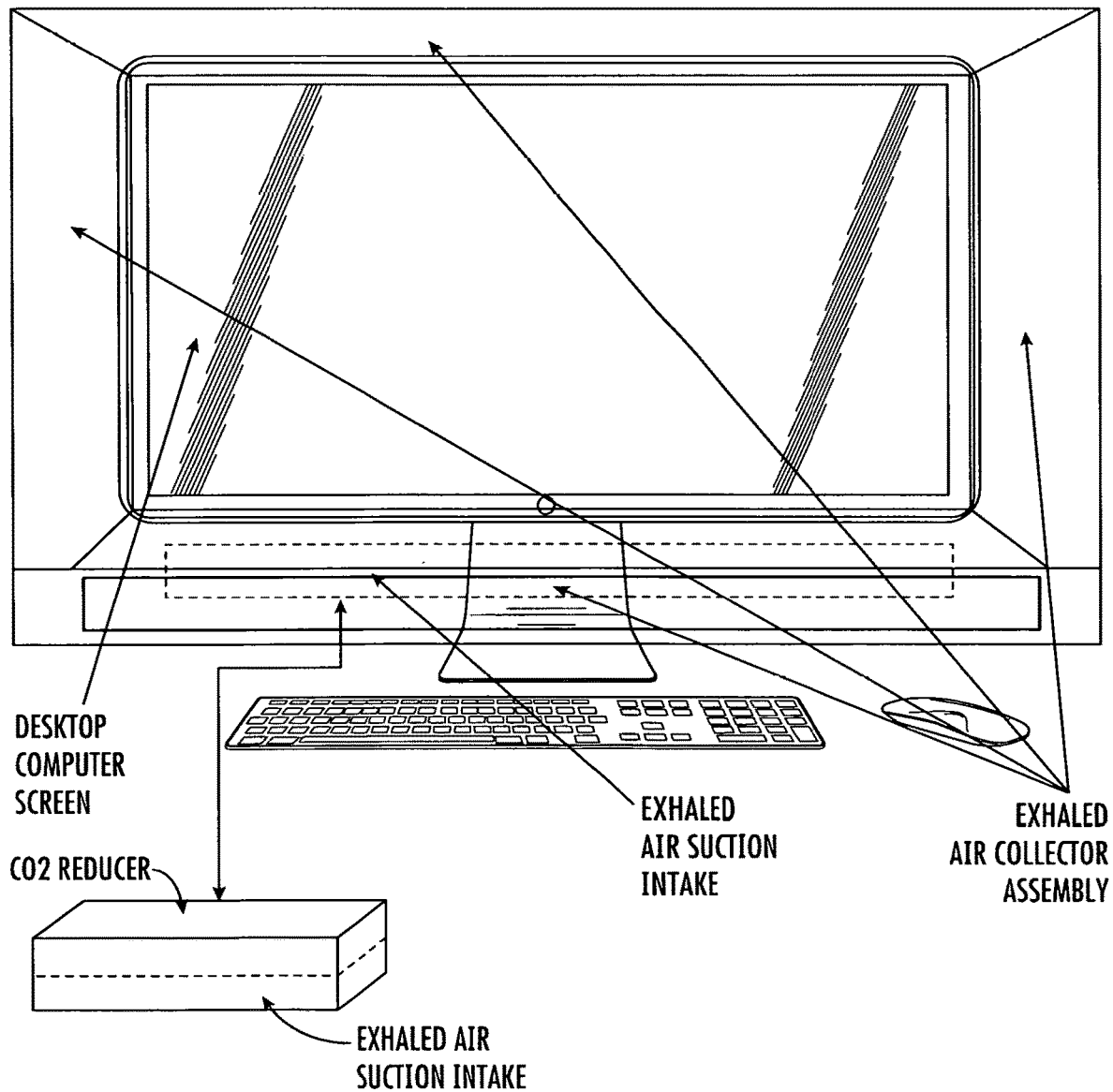
FIG. 20 is a depiction of an embodiment of the current invention, showing a monitor with an integrated exhaled air collector and carbon dioxide ("CO2") reducer.
Figure 21:
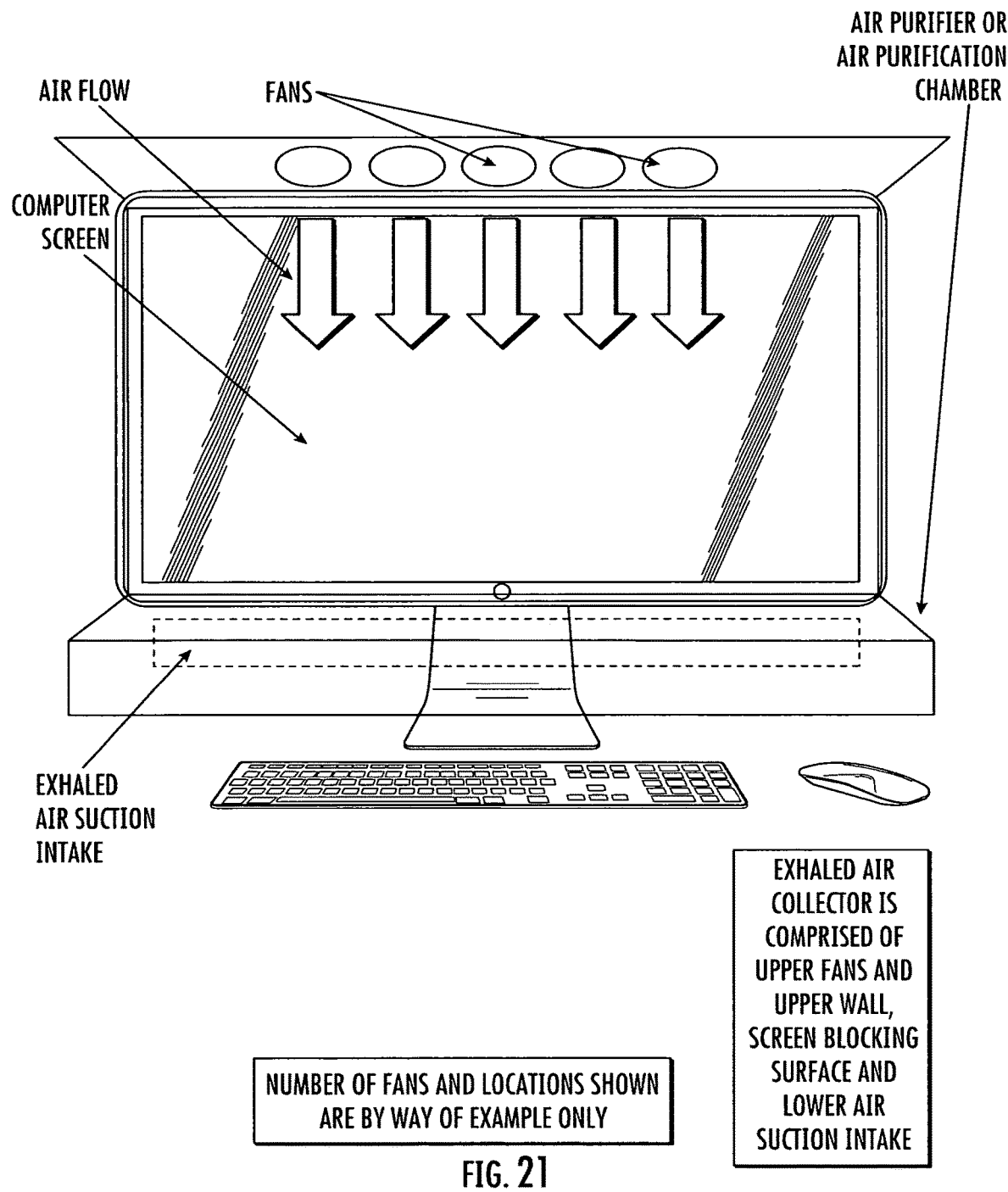
FIG. 21 is a depiction of an embodiment of the current invention, showing a monitor with an integrated exhaled air purification unit. In aspects, the exhaled air collector comprises upper fans and upper wall, screen blocking surface, and lower air suction intake.
Figure 22:
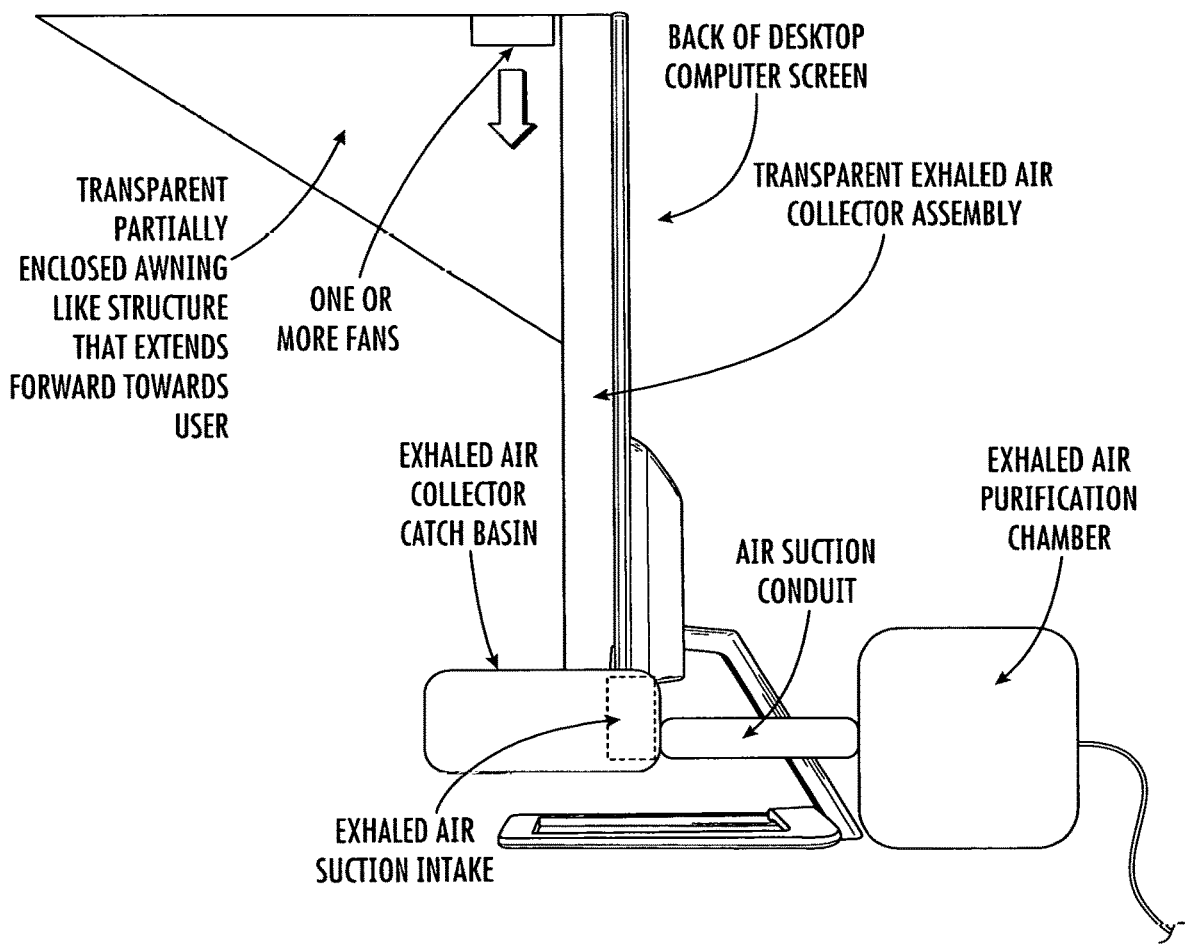
FIG. 22 is a depiction of an embodiment of the current invention, showing a monitor with an integrated exhaled air purification unit. In aspects, the system includes an awning-like structure that extends towards the user as depicted. In aspects, the awning can be transparent, semi-transparent, or opaque.
Figure 23:
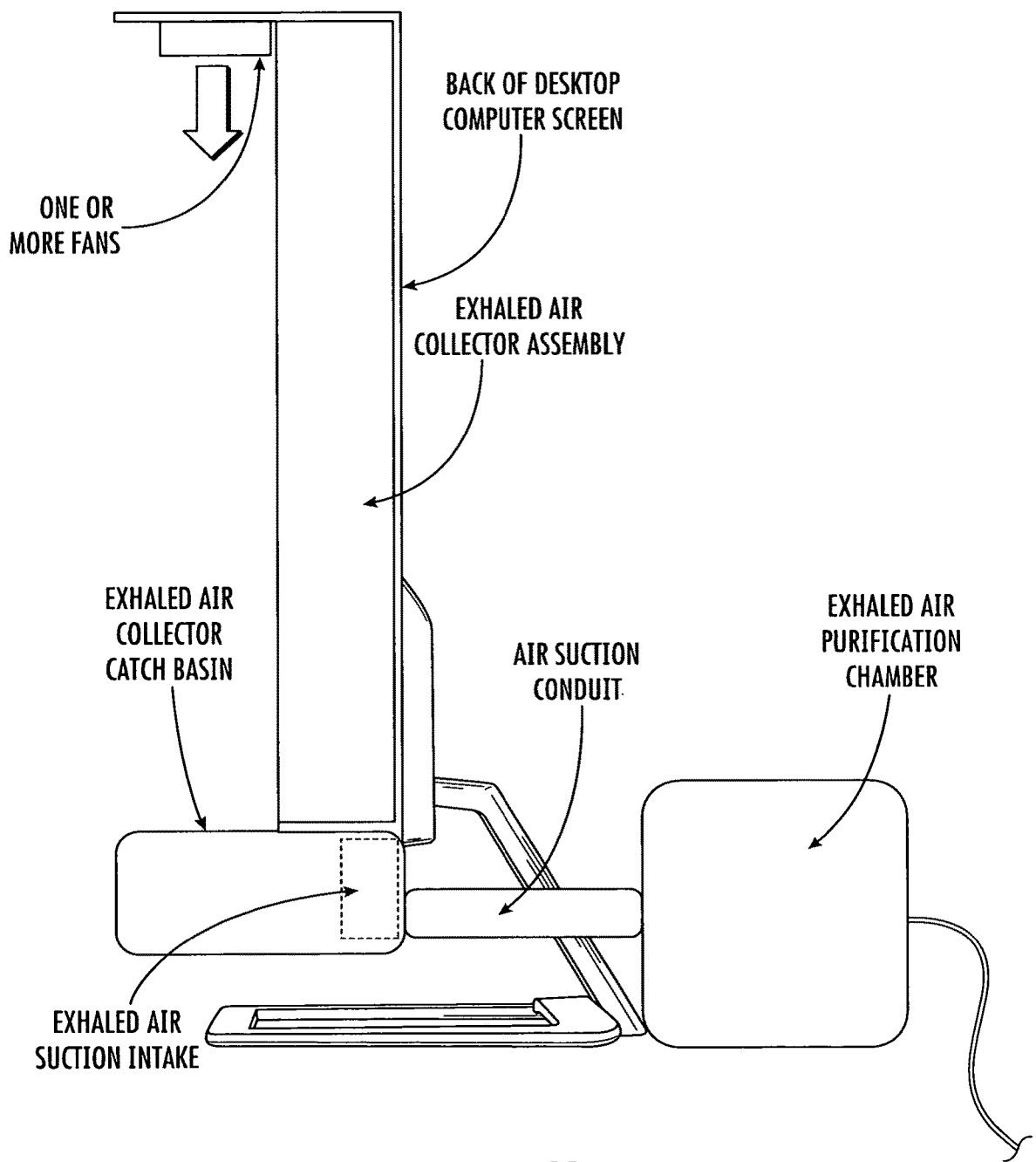
FIG. 23 is a depiction of an embodiment of the current invention, showing a monitor with an integrated exhaled air purification unit.
Figure 24:
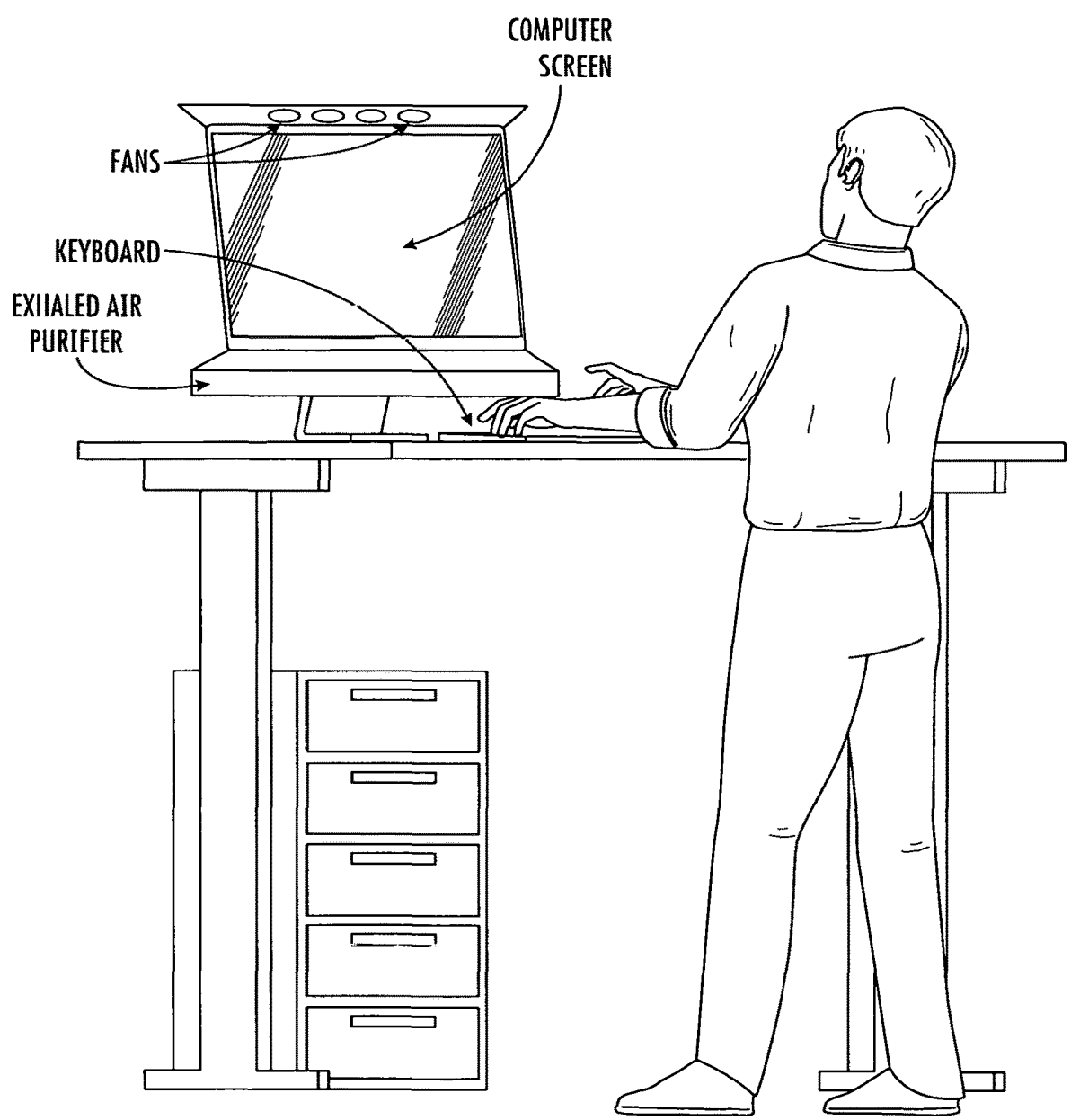
FIG. 24 is a depiction of an embodiment of the current invention, showing an implementation of the system at a stand up desk.
Figure 25:
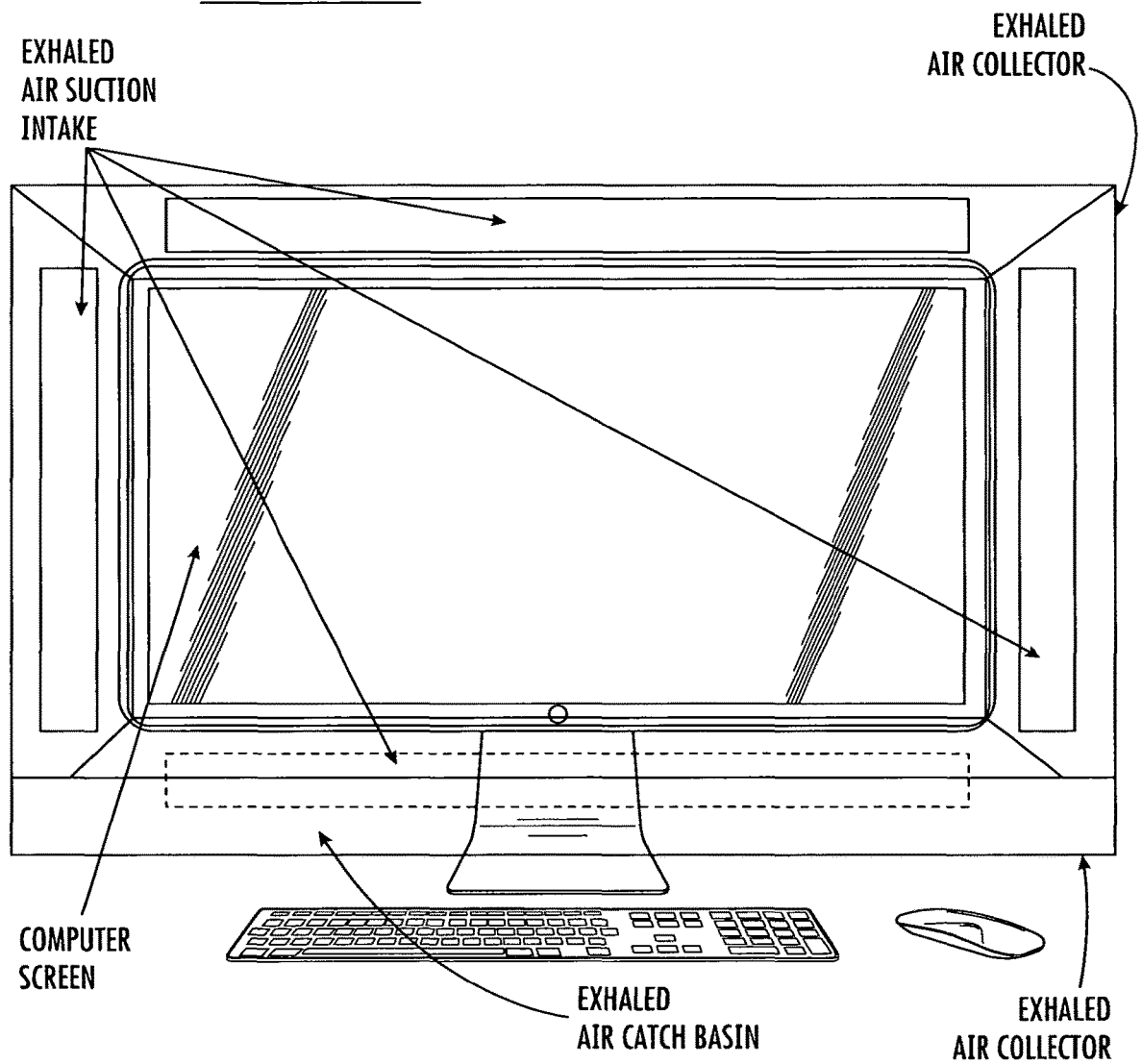
FIG. 25 is a depiction of an embodiment of the current invention, showing a monitor with an integrated exhaled air collector.

In embodiments, the computer user can be sitting or working within 36 inches of the computer screen or computer monitor. In cases, the user is sitting or working within 18-22 inches of the computer screen or computer monitor. In other cases, the user is standing at a desktop computer monitor or tabletop computer monitor and is within 30 inches of the computer screen or computer monitor. In aspects, an exhaled air collector comprises an exhaled air suction intake. The exhaled air suction intake can be located within a bottom $\frac{1}{3}$ ("third") of the exhaled air collector. In embodiments, multiple exhaled air collectors are located around a portion or all the peripheral front side of a computer monitor or computer screen. In cases, the exhaled air collector can further comprise one or more fans that are located at or above a top of the computer screen and attached to the exhaled air collector. The fan or fans can blow air downward thus helping to move exhaled air downward towards the exhaled air suction intake. (See, e.g., FIG. 9, FIG. 17, FIG. 18.) In other cases, the exhaled air collector is devoid of an external fan that is located towards the top of the exhaled air collector.

An exhaled air collector can provide a total air suction (air flow) volume and velocity that ranges between 25 cubic feet per minute ("CFM") and 1000 CFM while either attached, connected, or integrated into/with the computer screen. In cases, a balance between an air suction (CFM) and a noise level ("dB") is preferably between 20 decibels ("dB") and 75 dB.

In embodiments, an external fan, fans, or fan strip can be attached at or above the top of the computer screen or computer monitor. The fan, fans, or fan strip can generate downward air flow that moves room air and exhaled air towards an air suction intake. In some cases, the downward air can be an air curtain. In embodiments, the exhaled air collector comprises a fan or fans located, close to an air suction intake that generates air flow towards and into an air suction intake. In still other embodiments, a fan or fans located within an air purifier or exhaled air purification chamber suck or pull air through the air suction intake into or towards a filter such as by way of example only, a HEPA filter. (See, e.g., FIG. 5, FIG. 11, FIG. 12, FIG. 13, FIG. 31, FIG. 32, FIG. 33, FIG. 34, FIG. 35.) The exhaled air collector can be used as a vessel that captures exhaled air and which the air flow can pass through, and whereby the air suction air flow is generated by a fan either located in a conduit or a connected exhaled air purification chamber. In cases, for the invention disclosed herein, the total air flow for the exhaled air collector including the one or multiple air suction intakes can range between 50 CFM and 500 CFM with a clean air delivery rate ("CADR") ranging between 25 CADR and 300 CADR. In cases, the invention disclosed herein will have a targeted dB of 60 dB or less, and preferably 50 dB or less.

Figure 9:
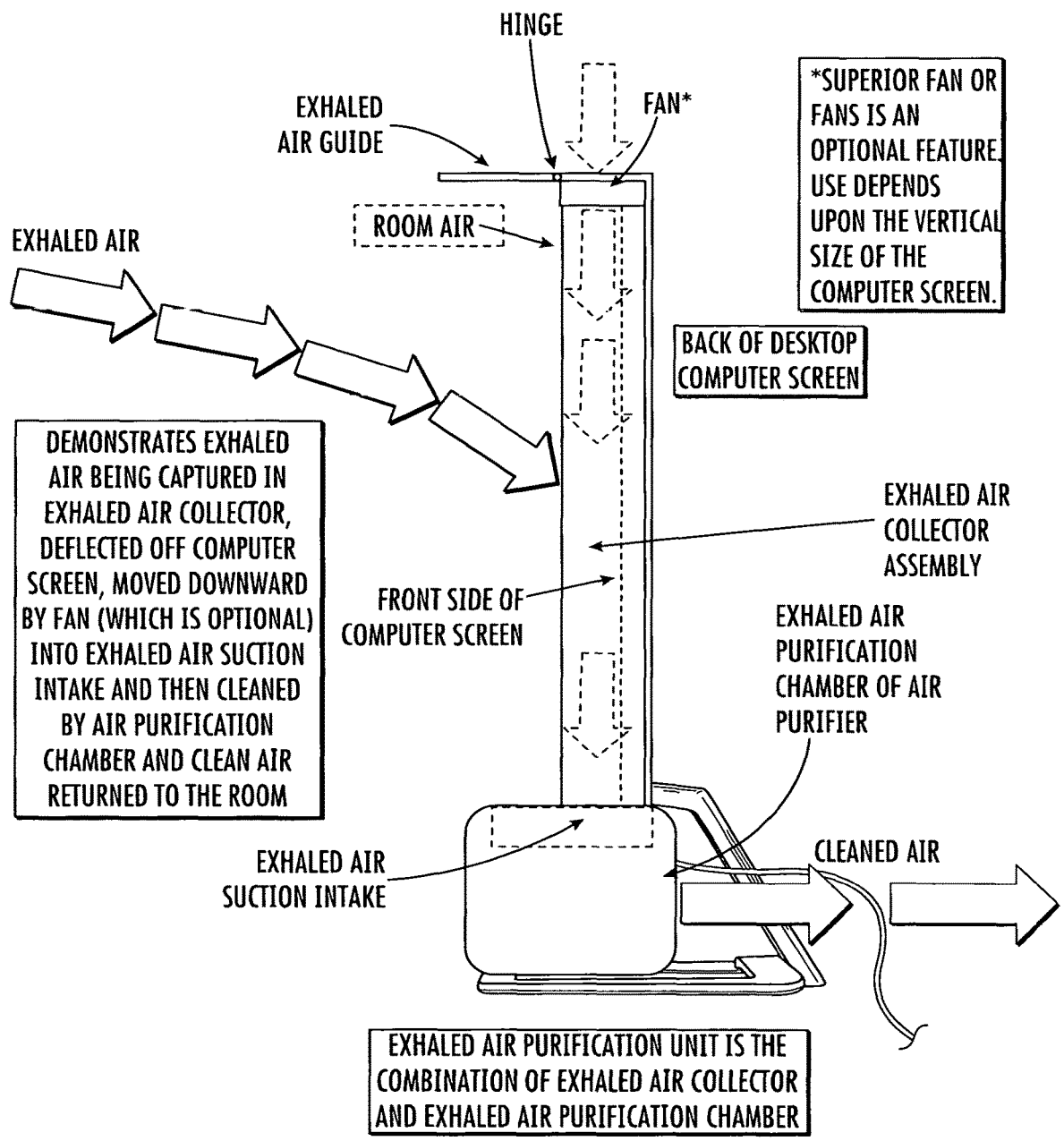
FIG. 9 is a depiction of an embodiment of the current invention, showing a monitor and demonstrating exhaled air being captured in the exhaled air collector, deflected off the computer screen, moved downward by an optional fan, and into an exhaled air suction intake, which connects directly to the air purification chamber or can be indirectly connected by a conduit. The air is then cleaned by the air purification chamber and returned to the room. In aspects, the superior fan or fans are an optional feature; use of the fan or fans depends on, for example, the vertical size/dimension(s) of the computer screen.
Figure 30:
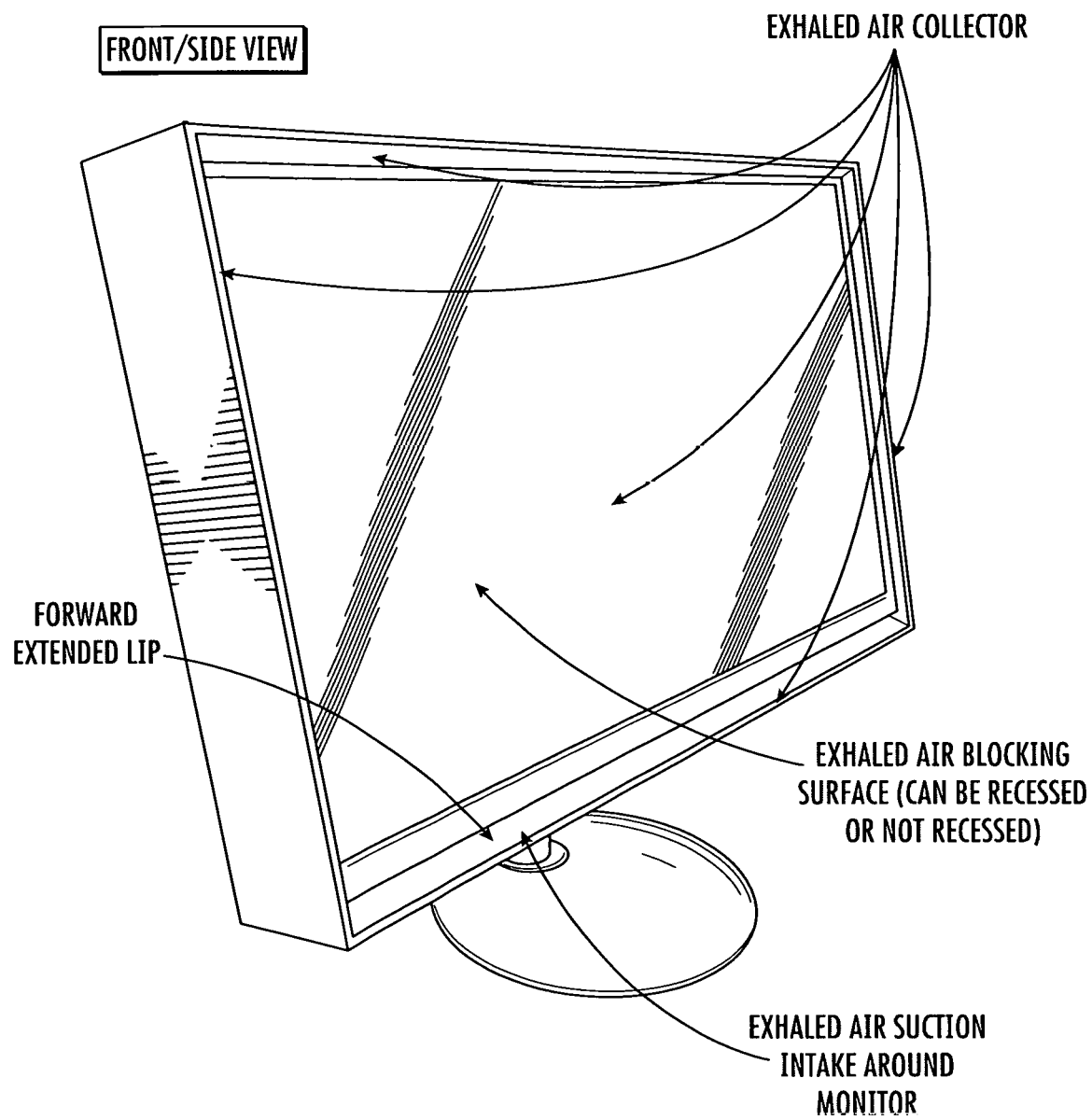
FIG. 30 is a front-side view depiction of an embodiment of the current invention, showing a monitor with an exhaled air collector, exhaled air blocking surface (optionally recessed), an exhaled air suction intake around the monitor, and a forward extended lip.
Figure 31:
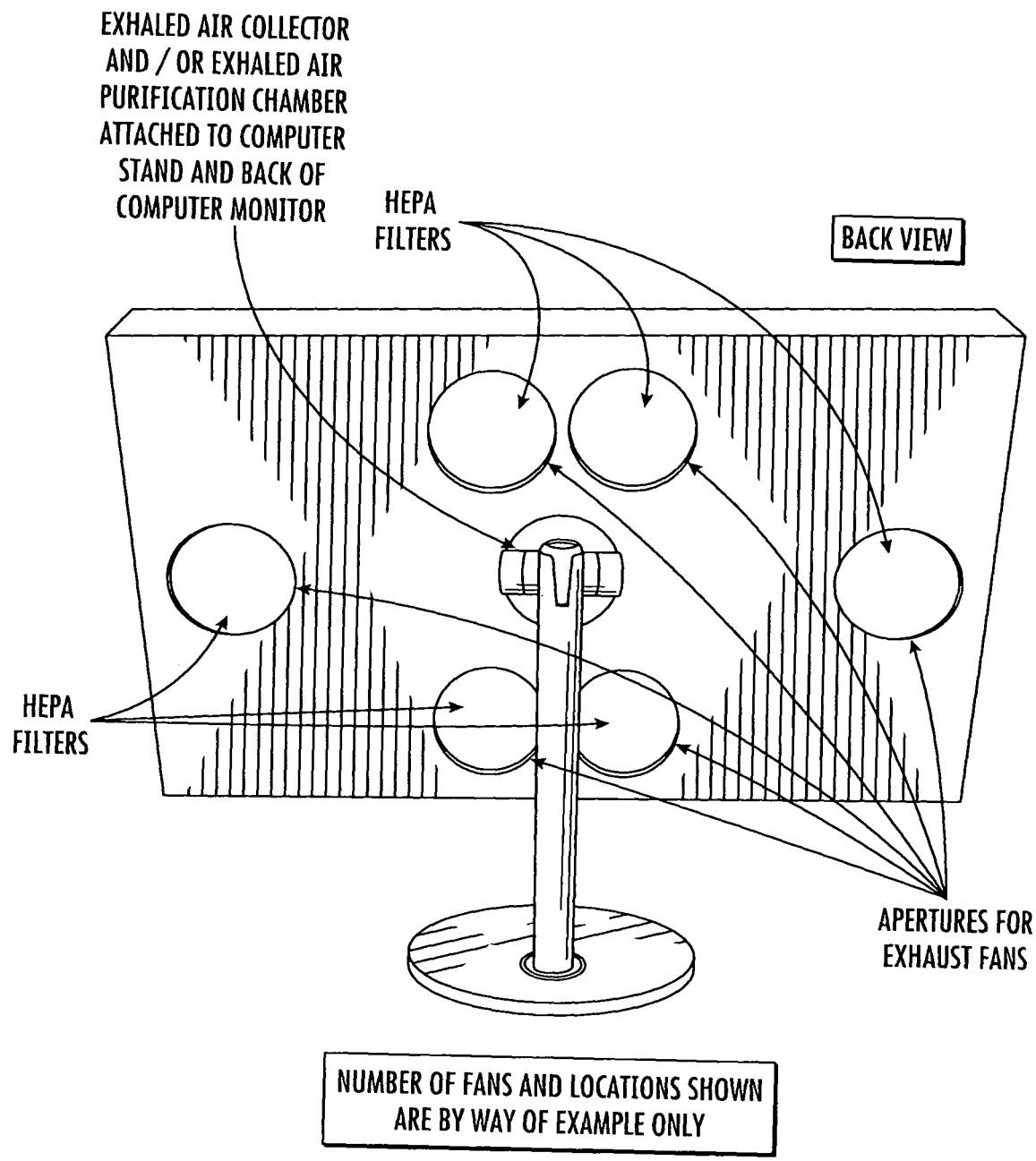
FIG. 31 is a back view depiction of an embodiment of the current invention, showing a monitor with an exhaled air collector and/or exhaled air purification chamber attached to a computer stand and back of a computer monitor.
Figure 32:
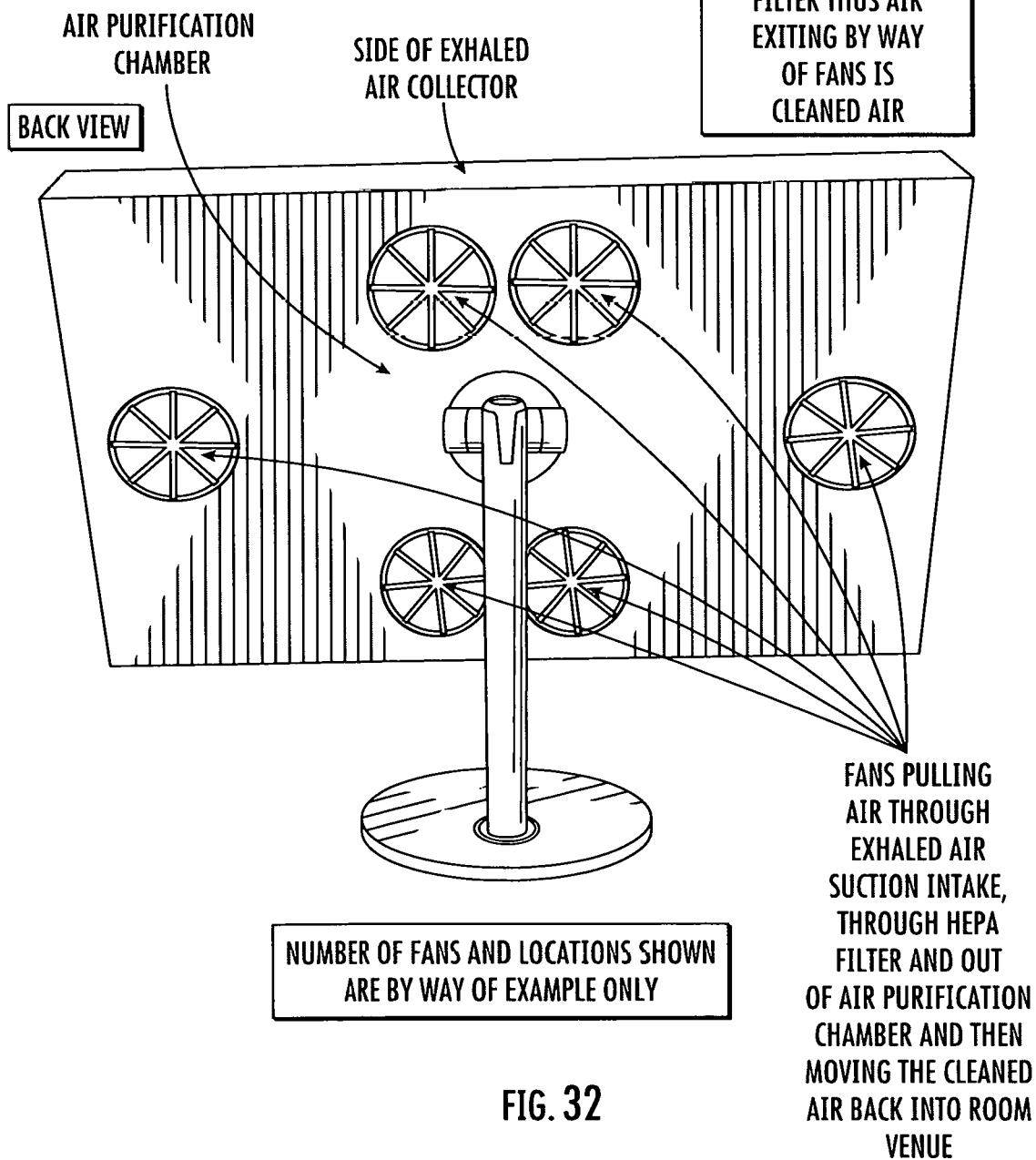
FIG. 32 is a back view depiction of an embodiment of the current invention, showing a monitor with an exhaled air purification chamber, wherein a fan or fans pull air through an exhaled air suction intake, through a filter (such as a HEPA filter), and out of the air purification chamber and thereby returning cleaned air back into the room venue.
Figure 33:
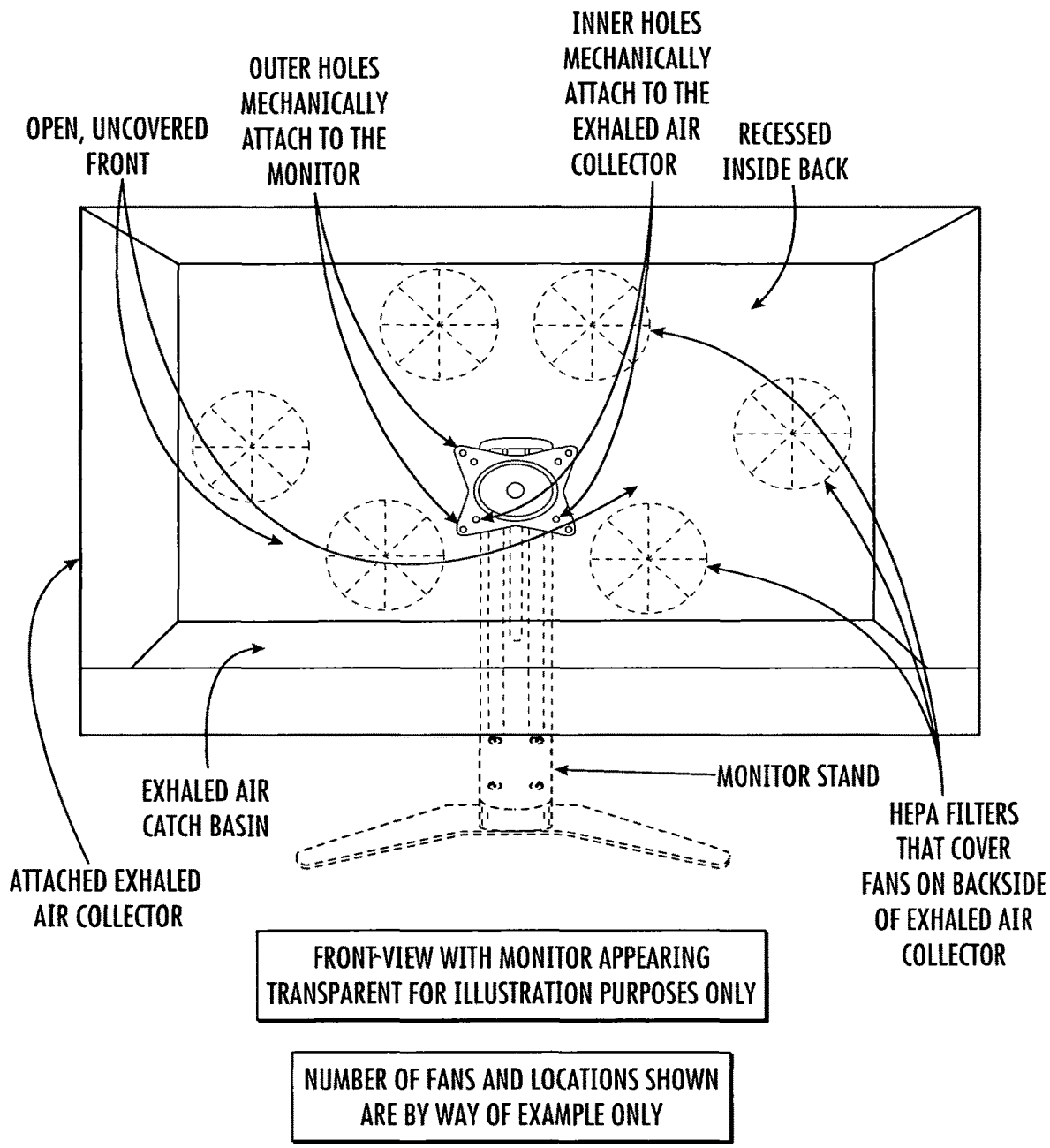
FIG. 33 is a front view depiction of an embodiment of the current invention, showing a monitor with an exhaled air collector. This embodiment shows a recessed exhaled air collector wherein air is moved to HEPA filters associated with fans on the backside of the air collector, wherein the HEPA filters clean the air and the fans pass the cleaned air back in to the room from which the air was collected/captured. This depiction shows the exhaled air collector having an exhaled air catch basin.
Figure 34:
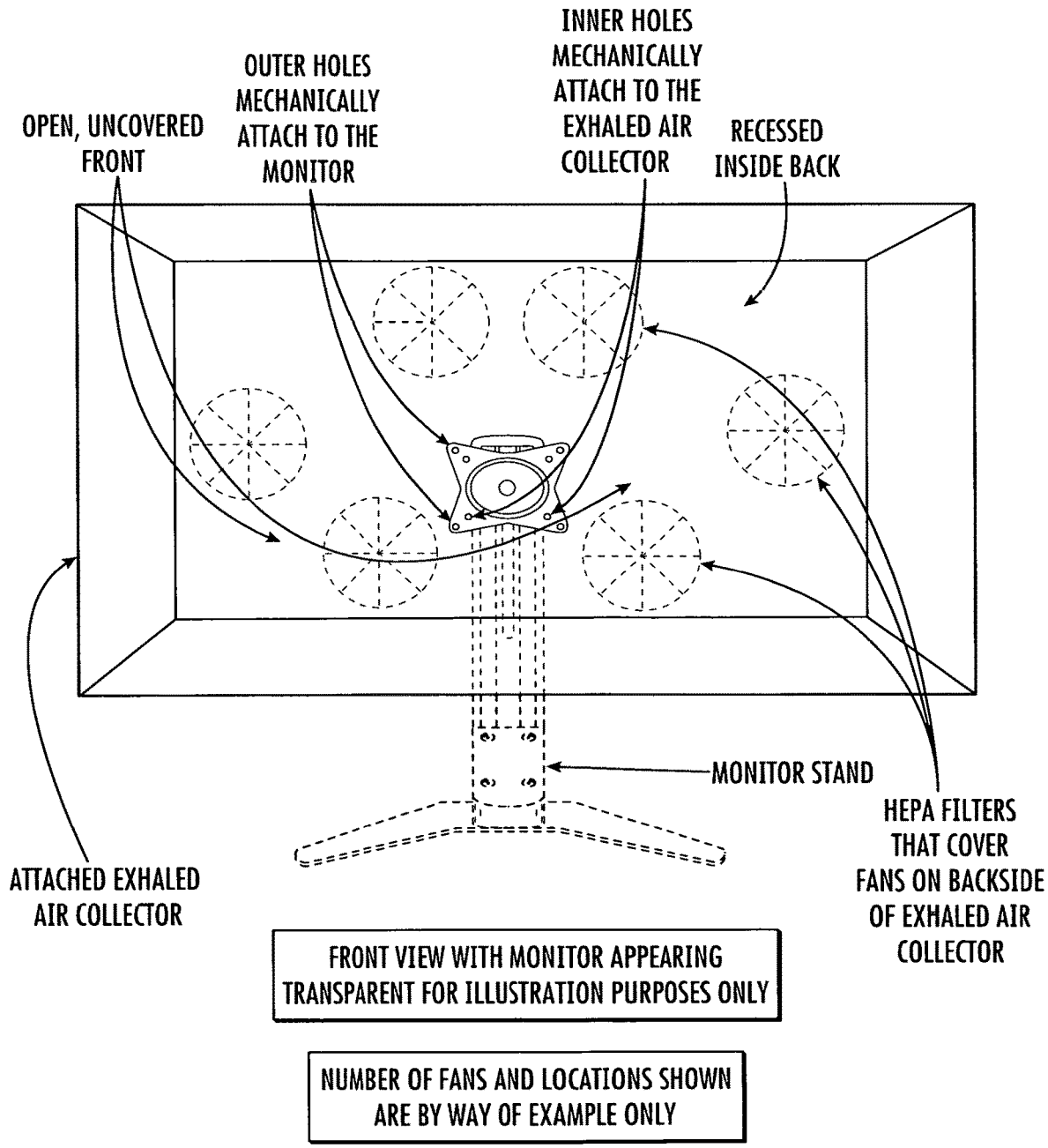
FIG. 34 is a front view depiction of an embodiment of the current invention, showing a monitor with an exhaled air collector. This embodiment shows a recessed exhaled air collector wherein air is moved to HEPA filters associated with fans on the backside of the air collector, wherein the HEPA filters clean the air and the fans pass the cleaned air back in to the room from which the air was collected/captured. This depiction shows the exhaled air collector without an exhaled air catch basin.
Figure 35:
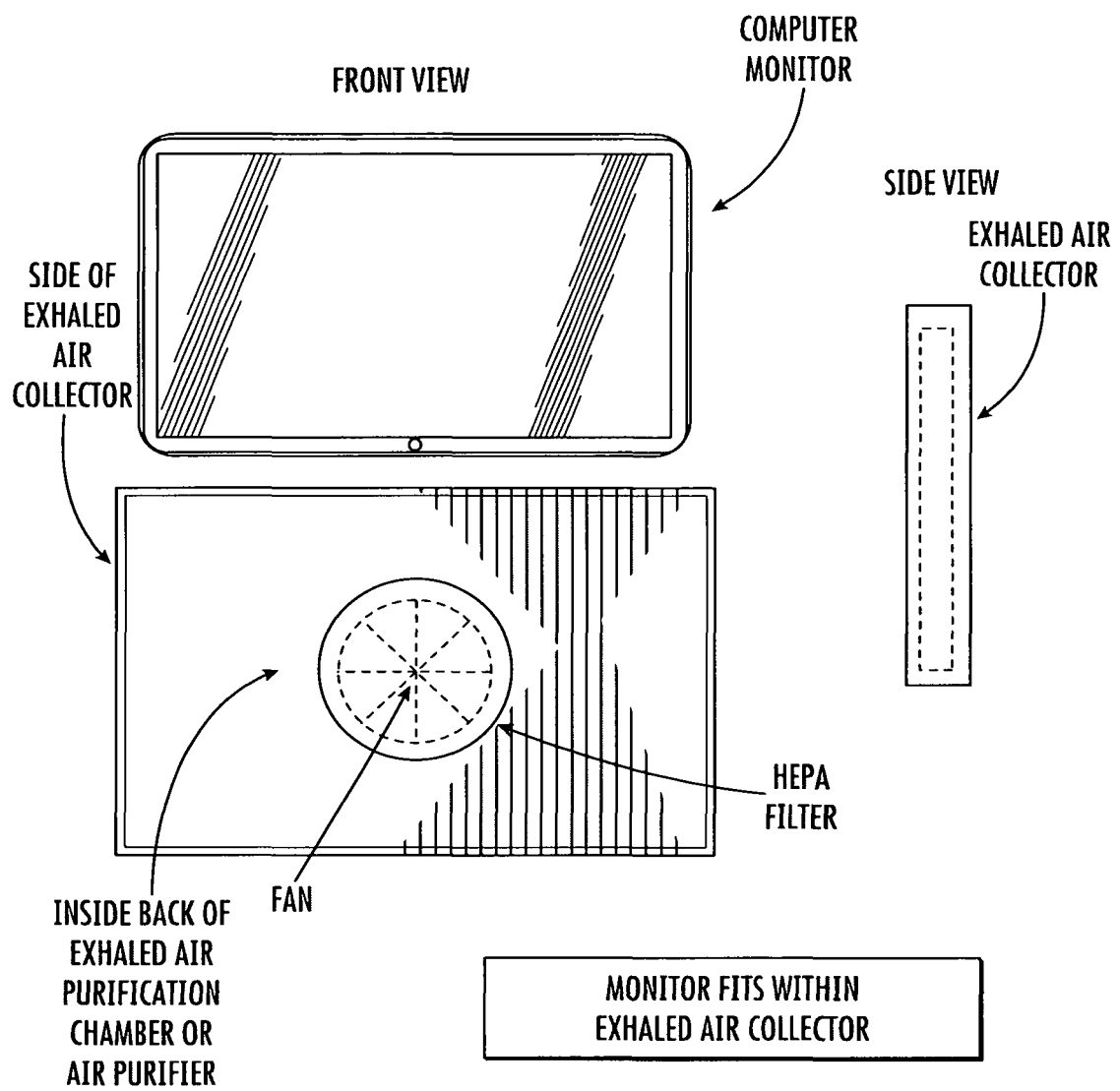
FIG. 35 is a front and side view depiction of an embodiment of the current invention, showing a monitor that is meant to fit within an exhaled air collector. The monitor and exhaled air collector are front facing, and the monitor fits within the exhaled air collector. One or more HEPA filters and associated fans can be located on a backside of the air purification unit to clean the air.

In embodiments, the air suction air flow pulls exhaled air of the user that is deflected off the computer screen or computer monitor and exhaled air that is forward of the computer screen or computer monitor (as well as at least some room air, in aspects) into the exhaled air collector, then into an exhaled air suction intake, and then towards an air purification chamber where the exhaled air is cleaned by one or more of, by way of example only, a HEPA filter, a carbon filter, another form of a filter, a microbicidal UV light, a microbicidal UVC light, a microbicidal Ionization, a microbicidal heat, a microbicidal agent, a microbicidal material, and/or an anti-microbial agent. (FIG. 9, FIG. 30.) In aspects, upon being cleaned by the air purification chamber, the air can be released back into the room where the computer screen is located. In cases, the cleaned air is 99+% free of the presence 0.3 micron and larger particles. In other cases, the cleaned air is 99+% free of the presences of 0.5 micron and larger particles. In still other cases, the cleaned air is 99+% free of the presences of 1 micron and larger particles.

Further, given that the screen exterior front surface is utilized in various embodiments as an exhaled air blocking surface, pathogens that are exhaled along with the exhaled air breath of the user in cases will strike the screen before being diverted to an air suction intake (whether being part of the exhaled air collector, exhaled air purification chamber or a conventional air purifier). In embodiments, the external screen surface can be coated or manufactured with an anti-microbial agent or microbicidal agent. For example, the monitor (screen) surface, the monitor stand, a docking station, and/or any other surface related to the air purification unit can be coated with transparent antimicrobial coating, such as, but not limited to, coatings containing Cu ion, Ag ion, or photocatalytic TiO2, which upon light and moisture is activated and destroys different pathogens. In another embodiment, the monitor (screen) surface, the monitor stand, the docking station, and any other surface of the air purification unit can be coated with transparent biocidal-containing coatings, such as but not limited to: air disinfectants, alcohols, ethanol, 2-Propanol, 2-Proponal and 1-proponal, 2-Proponal and 1-proponal Benzalkonium chloride, Benzalkonium chloride, didecyldimethyl ammonium chloride, didecyldimethyl ammonium chloride Chlorohexidine digluconate, Chlorohexidine digluconate, sodium hypochlorite, hydrogen peroxide, formaldehyde, glutardialdehyde, ortho-phtalaldehyde, aldehydes, povidone iodine, iodine, oxidizing agents, peroxy and Peroxo acids, phenolics, quaternary ammonium compounds, and/or inorganic compounds (e.g., chlorine, hypochlorite, or hypochlorous). In yet another embodiment, the surfaces can be sprayed and/or wiped with an antimicrobial agent before each use or are sprayed/wiped in time intervals (e.g., daily, weekly, or monthly). In some embodiments, the screen surface can be made to be liquid- and/or oil-repellent, i.e. hydrophobic and olephobic, in nature. By way of example only, this can be accomplished using low-surface-energy materials, such as, but not limited to, wax, Teflon®, PDMS, etc., which give rise to large water contact angles of greater than 90°. The liquid and oil droplets on such surfaces do not attach to them, but rather roll-up and slide, especially if the surface is inclined under angle or is a vertical surface. In still other embodiments, the surface can be made of hydrophobic or superhydrophobic structural elements, preferably multi-scaled periodic structures which do not interfere with the transparency but enable water contact angles of greater than 90°. It is known that such surfaces also yield to reduced contact times to bouncing droplets and aerosols. (See, e.g., Ref: L. Wang et al., Compact nanoscale textures reduce contact time of bouncing droplets, Sci. Adv. 2020; 6: eabb2307; F. Yu, et al., Durable Super-repellent Surfaces: From Solid—Liquid Interaction to Applications, Acc. Mater. Res. 2021, 2, 920-932.) In another embodiment, the surface can be made repellent by applying a hydrophobic or super-hydrophobic coating before each use or periodically (e.g., daily, weekly, monthly), like those provided by Surfactis® Technologies (Hydrophobic Coating for Optics—Surfactis®), nano-Care® Company (Durable water repellent» hydrophobic coating(nanoCare® (nano-care.com)), Prosoco® (Masonry Water Repellents|Water Repellent Coatings—PROSOCO®) and others.

In embodiments, the exhaled air collector can comprise an exhaled air blocking surface that is the front surface of the computer screen or display screen. The exhaled air blocking surface can be recessed, such as recessed in the exhaled air collector and/or computer monitor. The exhaled air blocking surface can be of or in a same imaginary plane as that of an outer lip of the exhaled air collector that forms the air suction intake (meaning that, in aspects, the exhaled air blocking surface is not recessed). In embodiments, the recessed exhaled air blocking surface can be that of the front surface of the display screen or computer screen. In embodiments, the non-recessed exhaled air blocking surface can be that of the front surface of the display screen or computer screen. The exhaled air purification chamber can comprise an air suction intake or intakes on the side or sides that are common with the exhaled air collector and cleaned air flow outlets on the side or sides that are common with the venue environment. In other embodiments, an air intake side of the exhaled air purification chamber can fill a portion, or all, of one or more of the top, the side, the bottom, and/or the back of the exhaled air collector.

In aspects, an air purification unit as used herein can be that of the exhaled air collector (which includes an exhaled air blocking surface, an exhaled air suction intake (in aspects, independent of, attached to, connected to, or combined with the exhaled air purification chamber), optional conduit, and/or optional exhaled air catch basin). The manner in which the exhaled air collector, the exhaled air purification chamber, and/or that of the exhaled air purification unit are designed can depend on the venue to which it or they is being utilized.

In aspects, the exhaled air purification unit can be built into or incorporated into/with the computer monitor. In aspects, the air purification unit can be built into or incorporated into/with the computer monitor. In aspects, the air purification unit can be attached to the computer monitor. In aspects, the air purification unit can be releasably attachable to the computer monitor. A computer monitor comprises a computer screen or display screen.

Figure 36:
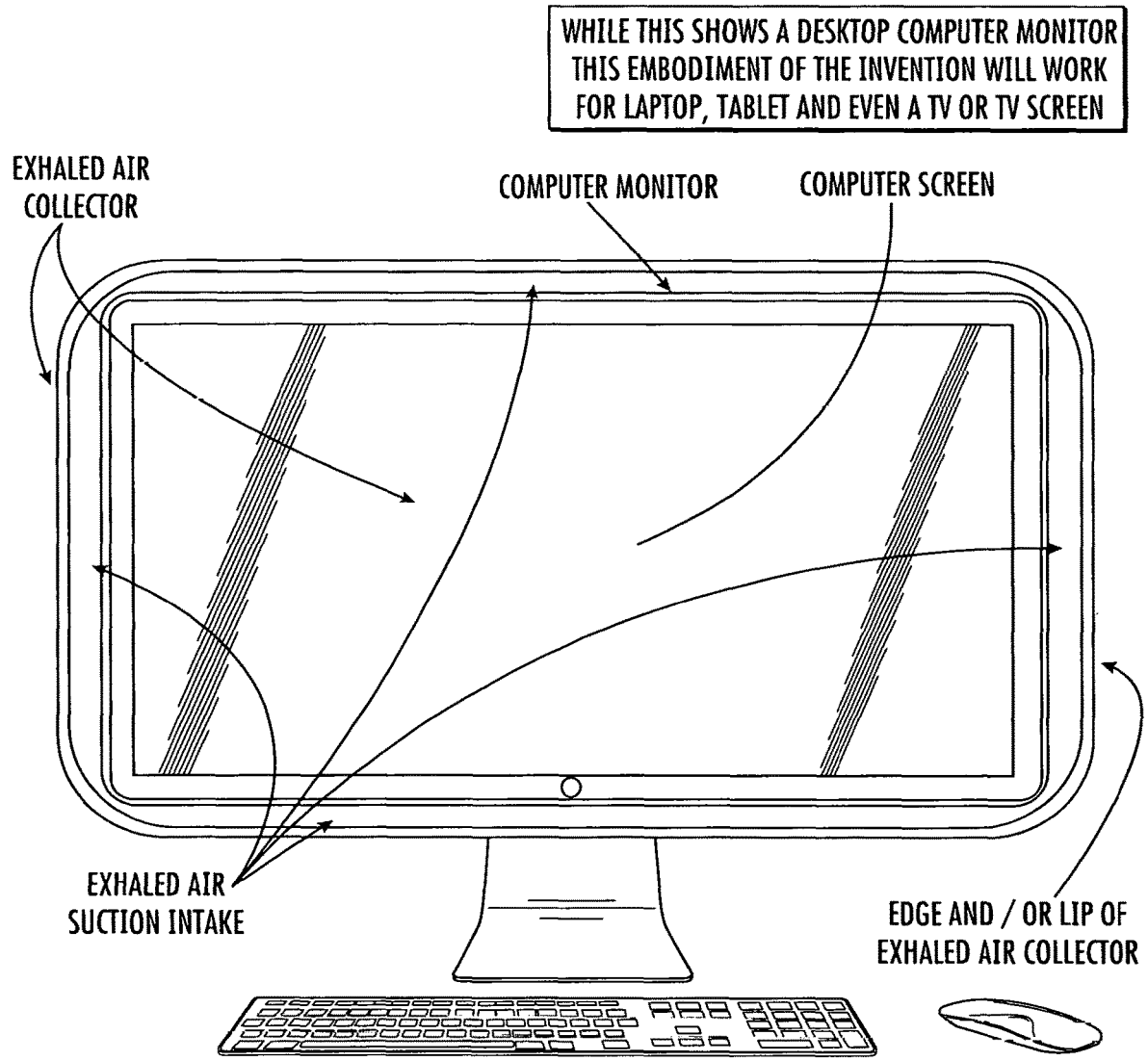
FIG. 36 is a front view depiction of an embodiment of the current invention, showing a monitor that is meant to fit within an exhaled air collector. While this embodiment shows a desktop computer monitor, this embodiment of the invention will work for laptop screens, tablet screens, and/or television screens. In aspects, the exhaled air collector includes the side walls and the computer screen. The air suction intake can surround the computer monitor or screen. The area behind the computer monitor can include the exhaled air purification chamber or the air purifier.

In aspects, an exhaled air purifier can mean the same as an exhaled air purification unit. In aspects, an exhaled air collector according to the present invention comprises a mostly open front that is mostly uncovered permitting a computer monitor, computer monitor screen, or a display screen to fit within a portion or all of the mostly uncovered and mostly open front. (See, e.g., FIG. 36.)

As used herein, a traditional or conventional air purifier is one that is currently (as of 2021) sold on the commercial marketplace, or that has been sold in the past. As used herein, a traditional or conventional air purifier is one that is designed to capture and clean mostly room air as opposed to being designed to capture and clean a higher percentage of exhaled air compared to the volume of room air. By way of example only, upon a cough or a sneeze (which are examples of exhaled air) with an existing traditional or conventional air purifier, a significant amount of the user's cough or sneezed exhaled air would overwhelm a traditional or conventional air purifier and disperse within the room's indoor air, whereas with an exhaled air purification unit according to the current invention, the exhaled air collector's exhaled air blocking surface will deflect and/or redirect most of the cough or sneeze's exhaled air towards an air suction intake that directs air into an air suction conduit or to an exhaled air purification chamber or exhaled air purifier, as described herein. Exhaled air can be that of an individual's normal exhaled air breath, sigh, cough, or sneeze, among other meanings of exhaled air that would be understood by one of ordinary skill in the art.

Figure 45:
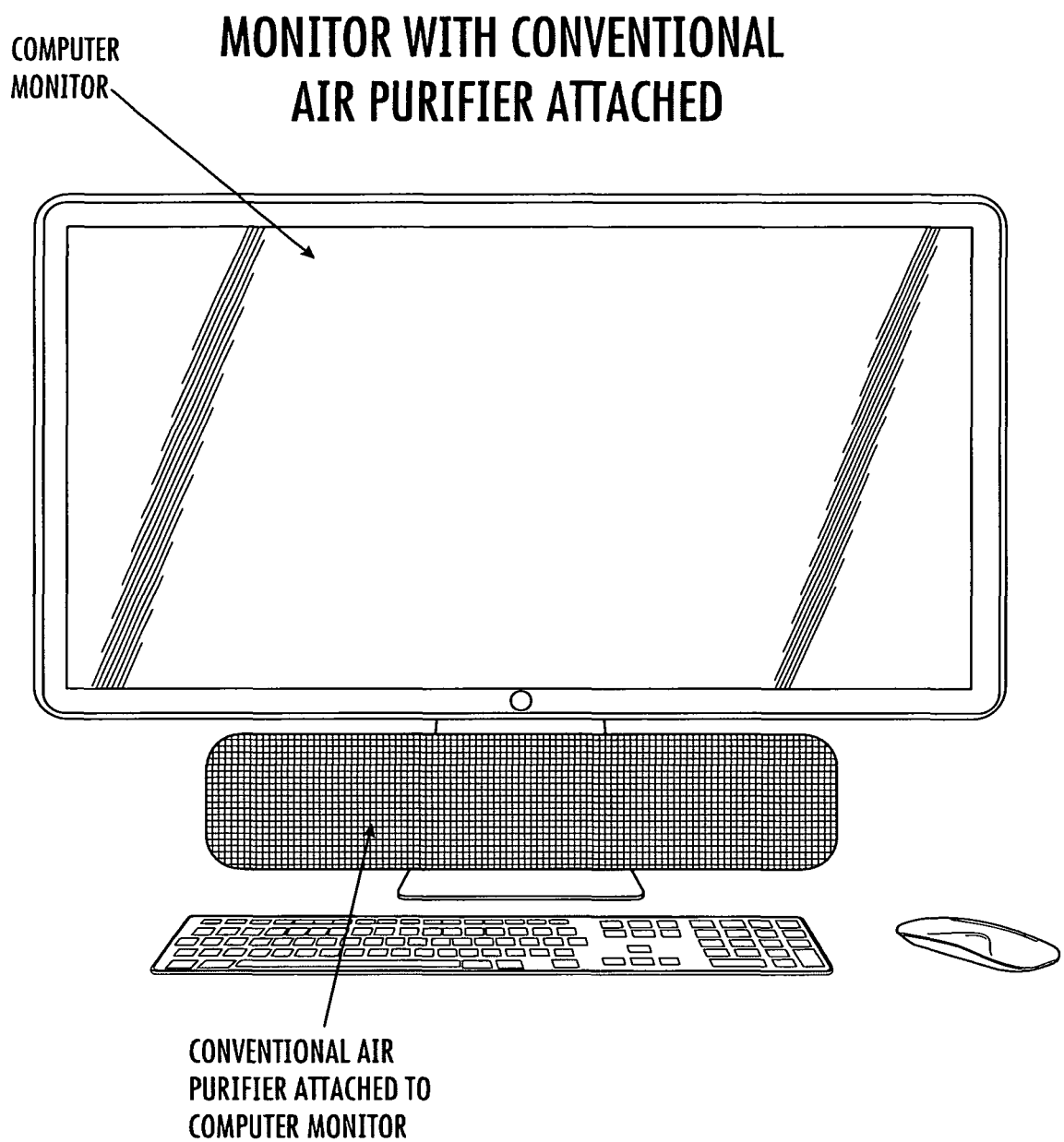
FIG. 45 is a depiction of an embodiment of the current invention, showing a monitor with a conventional air purifier attached.
Figure 46:
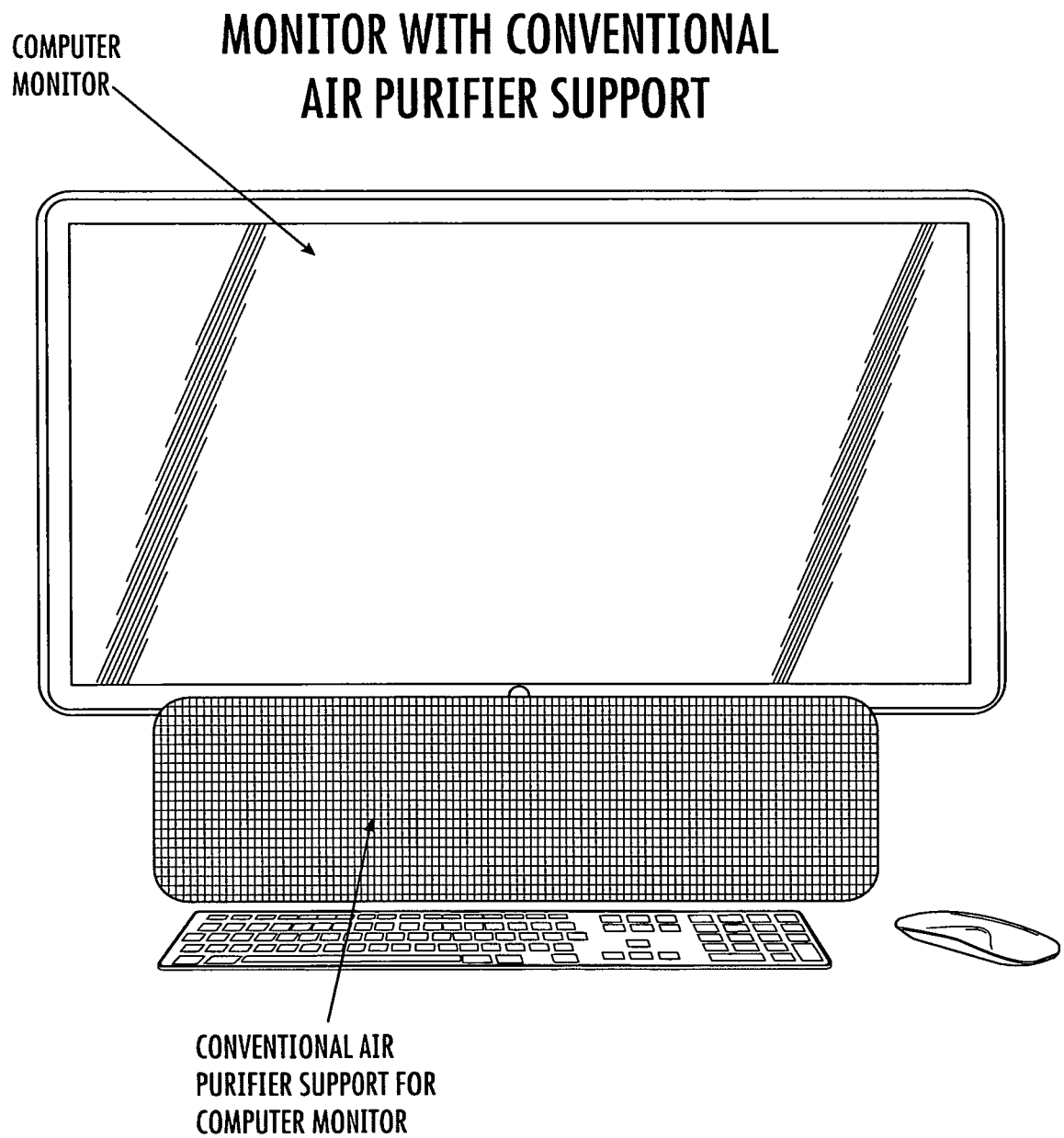
FIG. 46 is a depiction of an embodiment of the current invention, showing a monitor with a conventional air purifier support.
Figure 47:
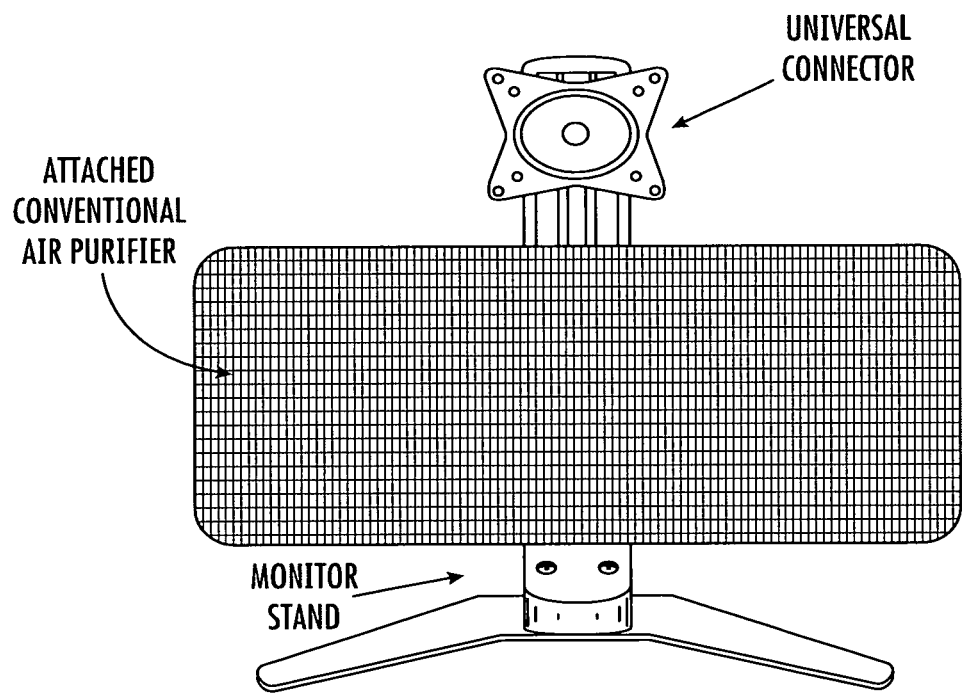
FIG. 47 is a depiction of an embodiment of the current invention, showing a monitor stand with an attached conventional air purifier.

In embodiments, a traditional or conventional air purifier can be attached to a computer monitor. (See, e.g., FIG. 45, FIG. 46.) In embodiments, a traditional or conventional air purifier can be attached to a computer screen. In embodiments, a traditional or conventional air purifier can be attached to a display screen. In embodiments, a traditional or conventional air purifier can be attached to a computer monitor stand. (See, e.g., FIG. 47.) In embodiments, a traditional or conventional air purifier can be releasably attachable to a computer monitor stand. In embodiments, a traditional or conventional air purifier can be built into a computer monitor stand. In embodiments, a traditional air purifier can be releasably attachable to a computer monitor. In embodiments, a traditional or conventional air purifier can be releasably attachable to a computer screen. In embodiments, a traditional or conventional air purifier can be releasably attachable to a display screen. In embodiments, a traditional or conventional air purifier can be incorporated into a computer monitor. In embodiments, a traditional or conventional air purifier can be designed into a computer monitor. In embodiments, a traditional or conventional air purifier can be releasably attached to a computer monitor. In embodiments, a traditional or conventional air purifier can be attached to a computer monitor. In embodiments, a traditional or conventional air purifier can be attached to the bottom of the computer monitor, computer monitor's screen or a display screen. In embodiments, a traditional or conventional air purifier can be attached around all or a portion of the perimeter of the computer monitor, computer monitor's screen, or a display screen.

Figure 37:
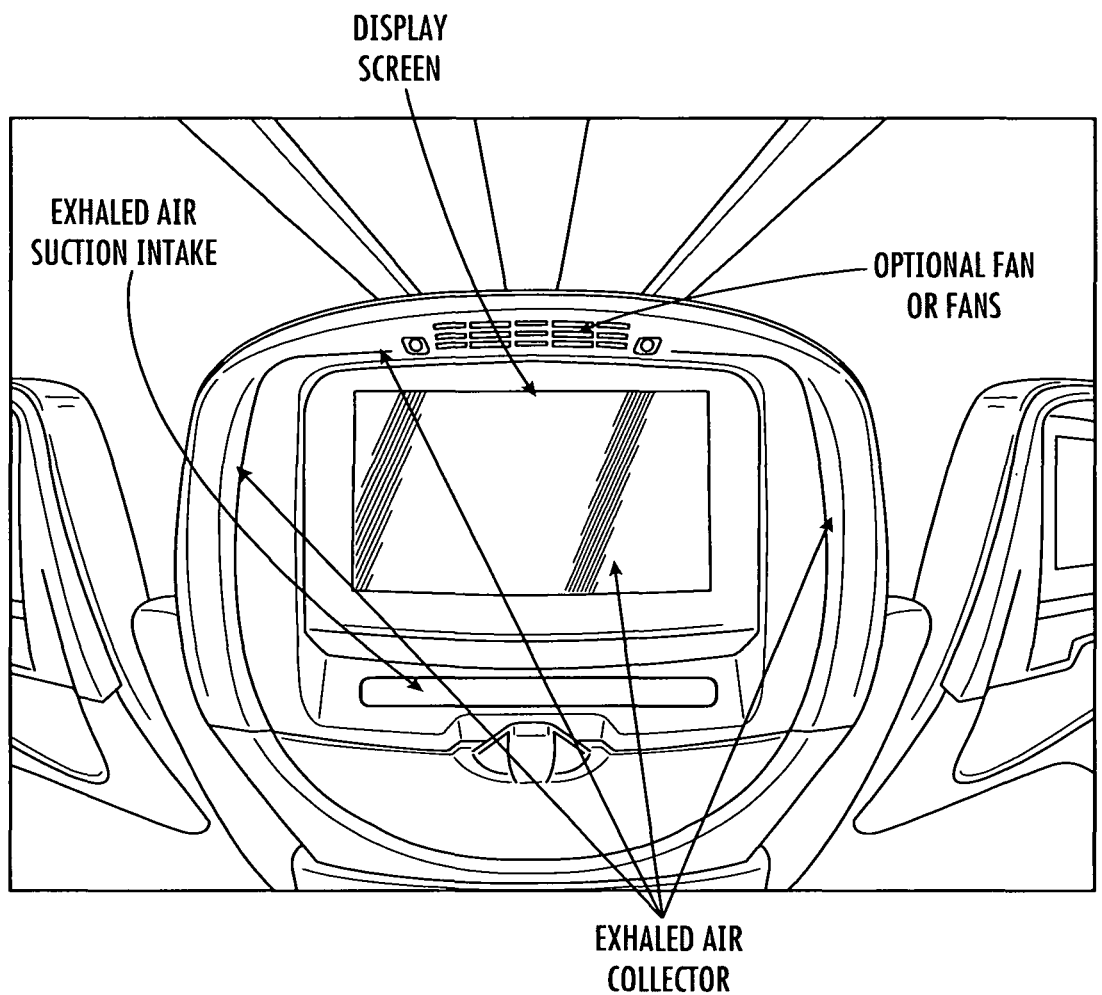
FIG. 37 is a depiction of an embodiment of the current invention, showing a monitor, exhaled air collector, and exhaled air suction intake, on the back of a seat, such as an aircraft seat.
Figure 38:
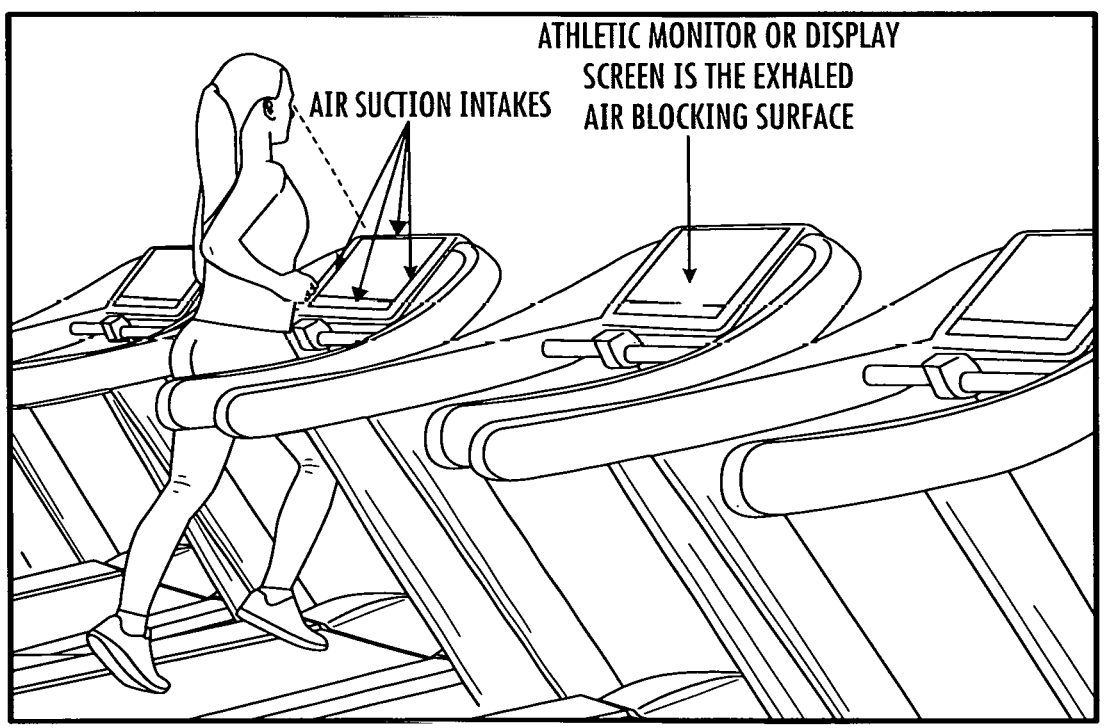
FIG. 38 is a depiction of an embodiment of the current invention, showing a monitor, exhaled air blocking surface (e.g., the athletic monitor or display screen), and exhaled air suction intake, on athletic/workout equipment, such as a treadmill or other cardio or weightlifting machine. The system would include the exhaled air collector and exhaled air purification chamber.
Figure 39:
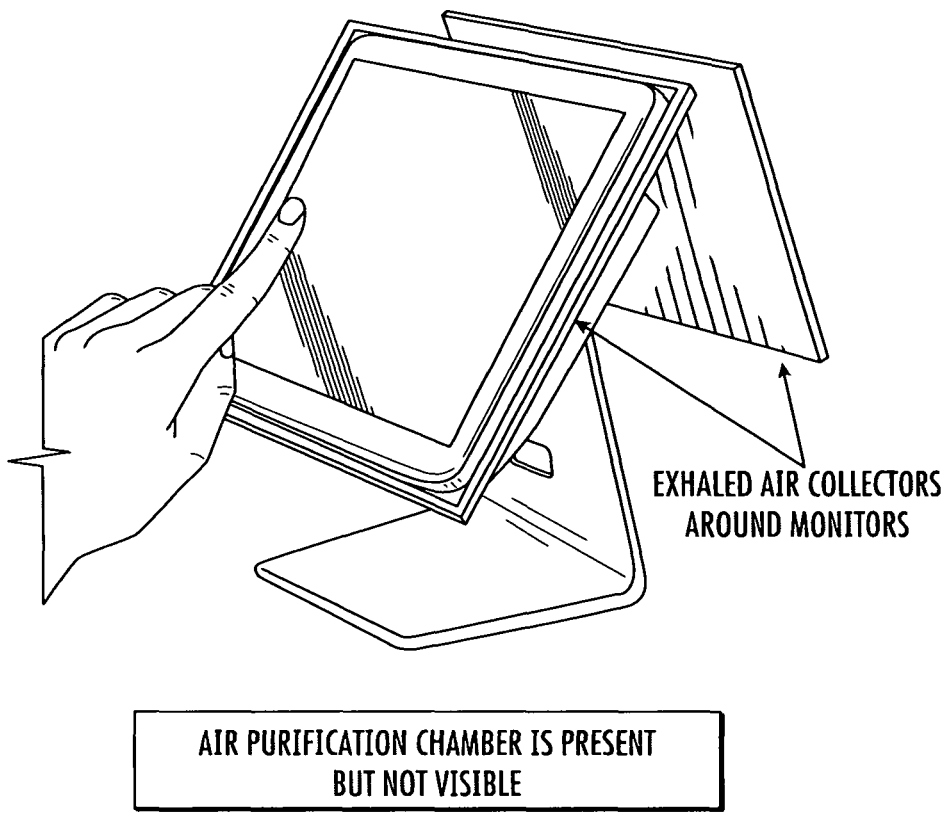
FIG. 39 is a depiction of an embodiment of the current invention, showing a monitor (or double monitor) and exhaled air collector, being used as a cash register monitor improvement.
Figure 40:
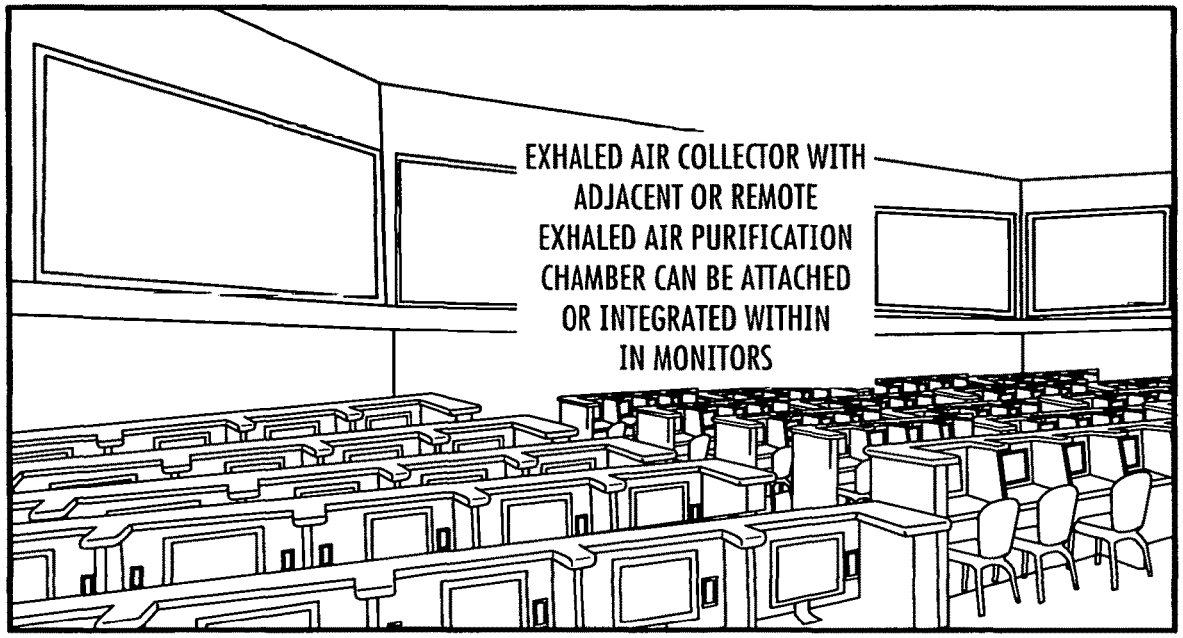
FIG. 40 is a depiction of an embodiment of the current invention, showing implementation in a casino and/or for gambling machines, wherein exhaled air collector is used with a monitor along with an adjacent or remote exhaled air purification chamber. The invention can be attached to or integrated with the monitors.
Figure 41:
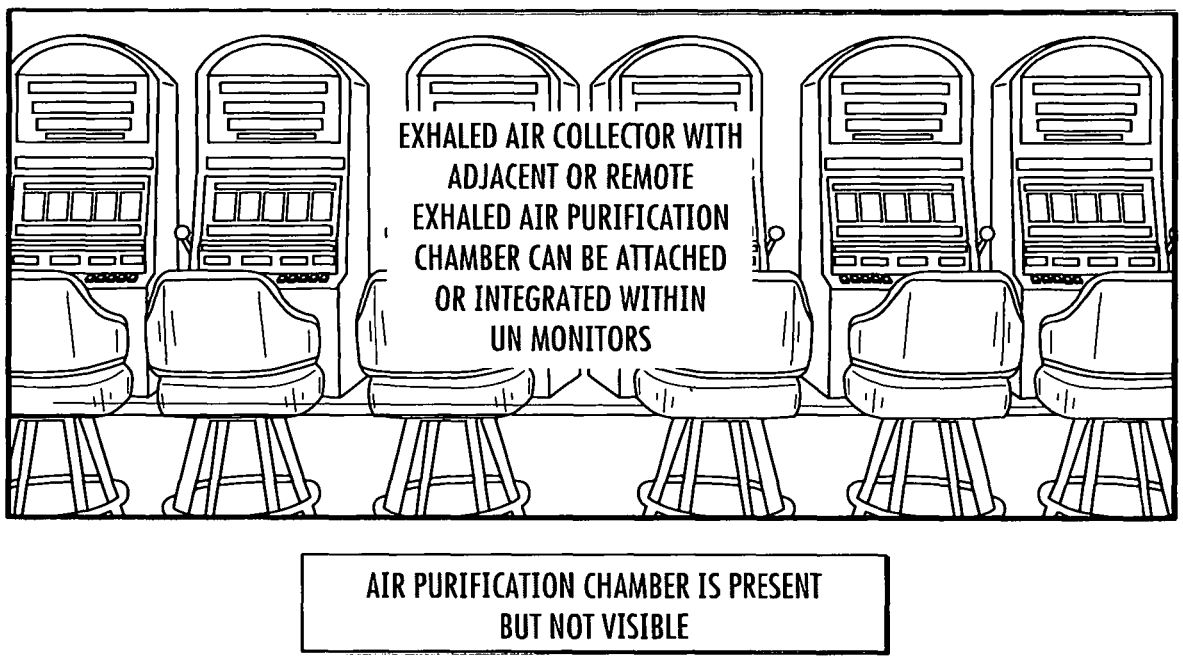
FIG. 41 is a depiction of an embodiment of the current invention, showing implementation in a casino and/or for gambling machines, wherein exhaled air collector is used with a monitor along with an adjacent or remote exhaled air purification chamber. The invention can be attached to or integrated with the monitors.
Figure 48:
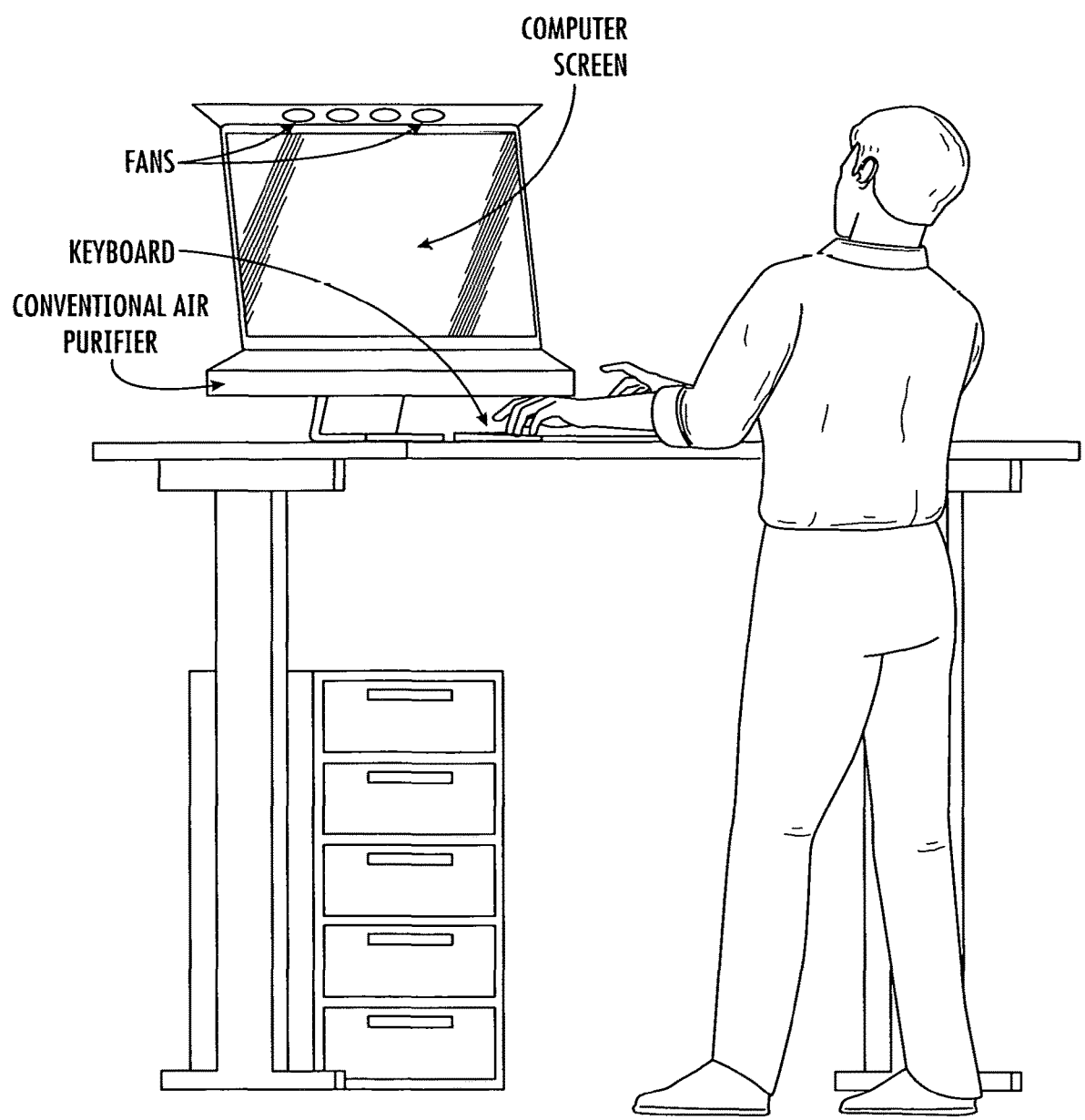
FIG. 48 is a depiction of an embodiment of the current invention, showing the invention being used in a standing desk fashion.

As used herein, a desk and a table can have the same meaning. As used herein, a desktop and tabletop can have the same meaning. As used herein, a desk and table can be that of a chair, a seat, or a bench that comprises a desk-like attachment. As used herein, a desk and table can be that of chair, seat, or bench that comprises a writing ledge attachment. As used herein, a desk and table can be that of chair, seat, or bench that comprises an attached or integrated horizontal work surface. While in embodiments an individual is sitting or standing in front of an air purification unit resting on, attached to, or integrated with a desk or a table, the invention disclosure herein covers that of an individual standing in front of a standing desk or standing table that further supports a computer, monitor or computer monitor, by way of example only, a tablet, a laptop, or a desktop. (See, e.g., FIG. 48.) As used herein, a computer monitor comprises a computer screen. As used herein, a gaming monitor has the same meaning as a computer monitor. A computer monitor can be a computer monitor comprising a display screen, a display monitor, or a display screen that is used, by way of example only, with exercise or physical workout equipment (see, e.g. FIG. 38), cash register, cash register with a double monitors (see, e.g., FIG. 39), gambling monitor screens (by way of example only slot machine monitors and other betting monitors) (see, e.g., FIG. 40, FIG. 41), seat backs of any type of vehicle (by way of example only, aircraft, automobile, truck, ship, bus, train, van, or subway) (see, e.g., FIG. 37), dashboard for any type of vehicle (by way of example only, aircraft, automobile, truck, ship, bus, train, van, or subway). For the purposes of this disclosure, a computer monitor having a video display screen can be that of any electronic display screen that is utilized in conjunction with a computer chip. For the purposes of this disclosure, a computer monitor having a video display screen can be that of any electronic display screen that displays data or an image that is generated by a device comprising a computer chip. As used herein, a display screen can be any electronic display screen. As used herein, a TV or television screen can be that of an electronic display screen. As used herein, an exhaled air purifier means the same as an exhaled air purification unit.

Figure 42:
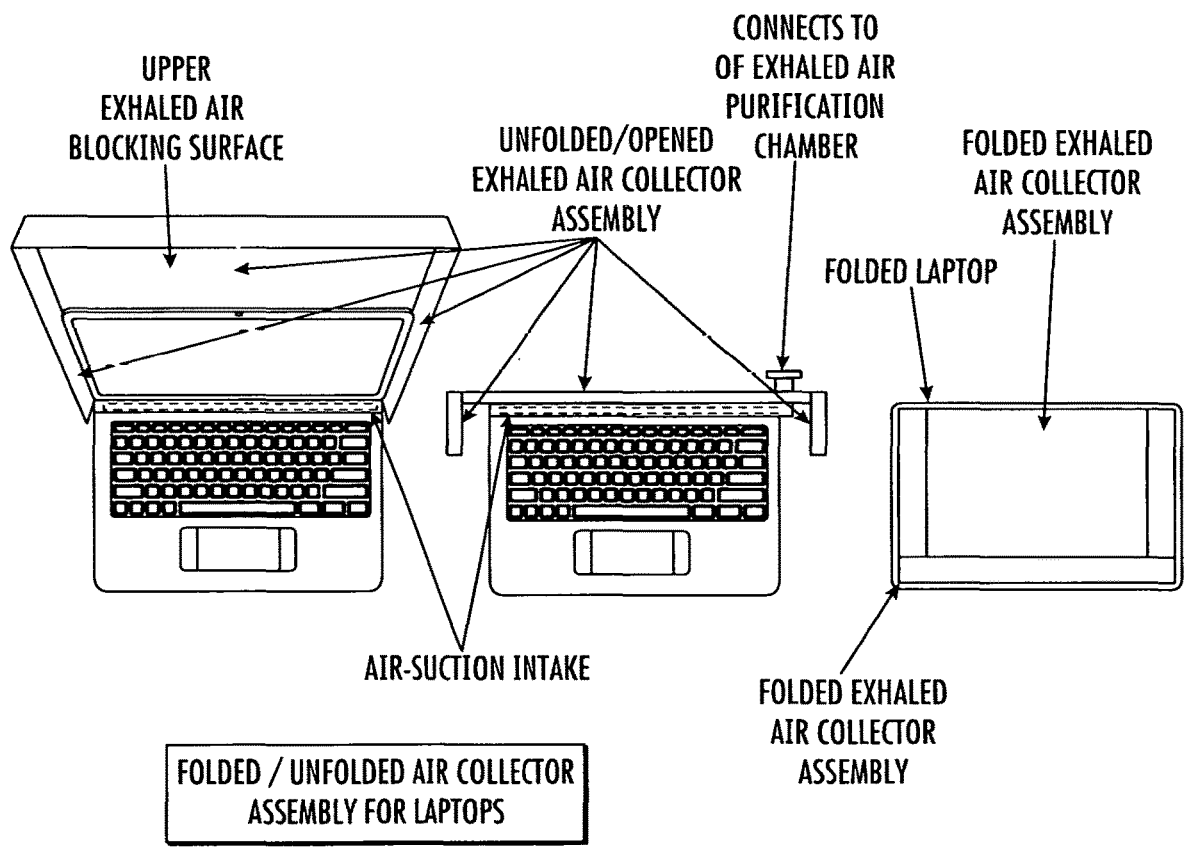
FIG. 42 is a depiction of an embodiment of the current invention, showing folded and unfolded exhaled air collectors for laptop computers. In aspects, the exhaled air collector can have an upper exhaled air blocking surface. The view show the laptop and invention with a screen tilted back, a screen vertical, and a laptop closed. In aspects, the exhaled air collector can connect to an air purification chamber. In aspects, the laptop screen fits within and is partially or completely surrounded on the sides and top by the exhaled air collector.
Figure 43:
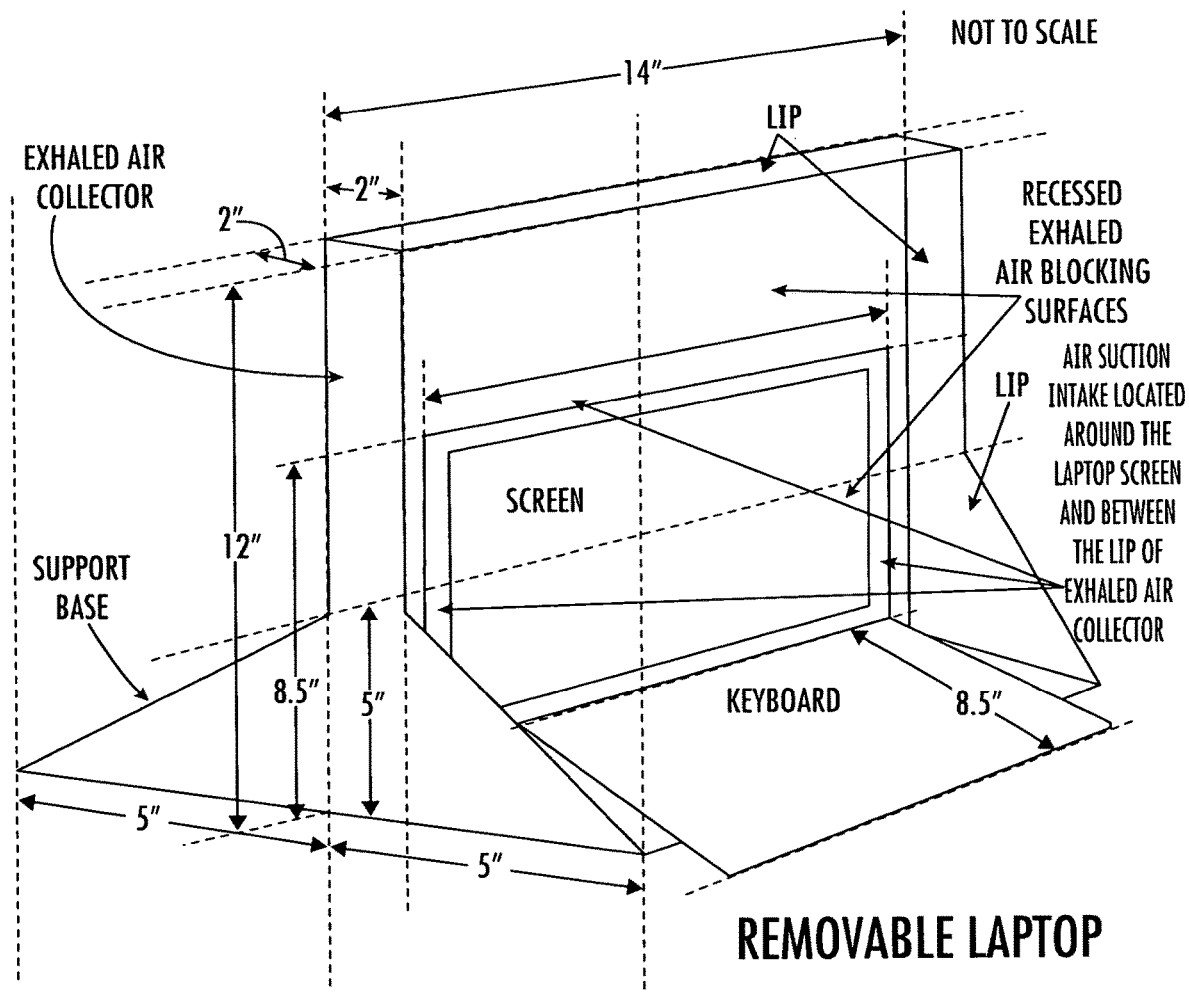
FIG. 43 is a depiction of an embodiment of the current invention, showing an exhaled air collector with exhaled air purification laptop docking station, with a laptop in or attached to the docking station. In aspects, this embodiment includes a recessed exhaled air blocking surface(s). In aspects, this embodiment includes an air suction intake located around the laptop screen and between the lip of the exhaled air collector.
Figure 44:
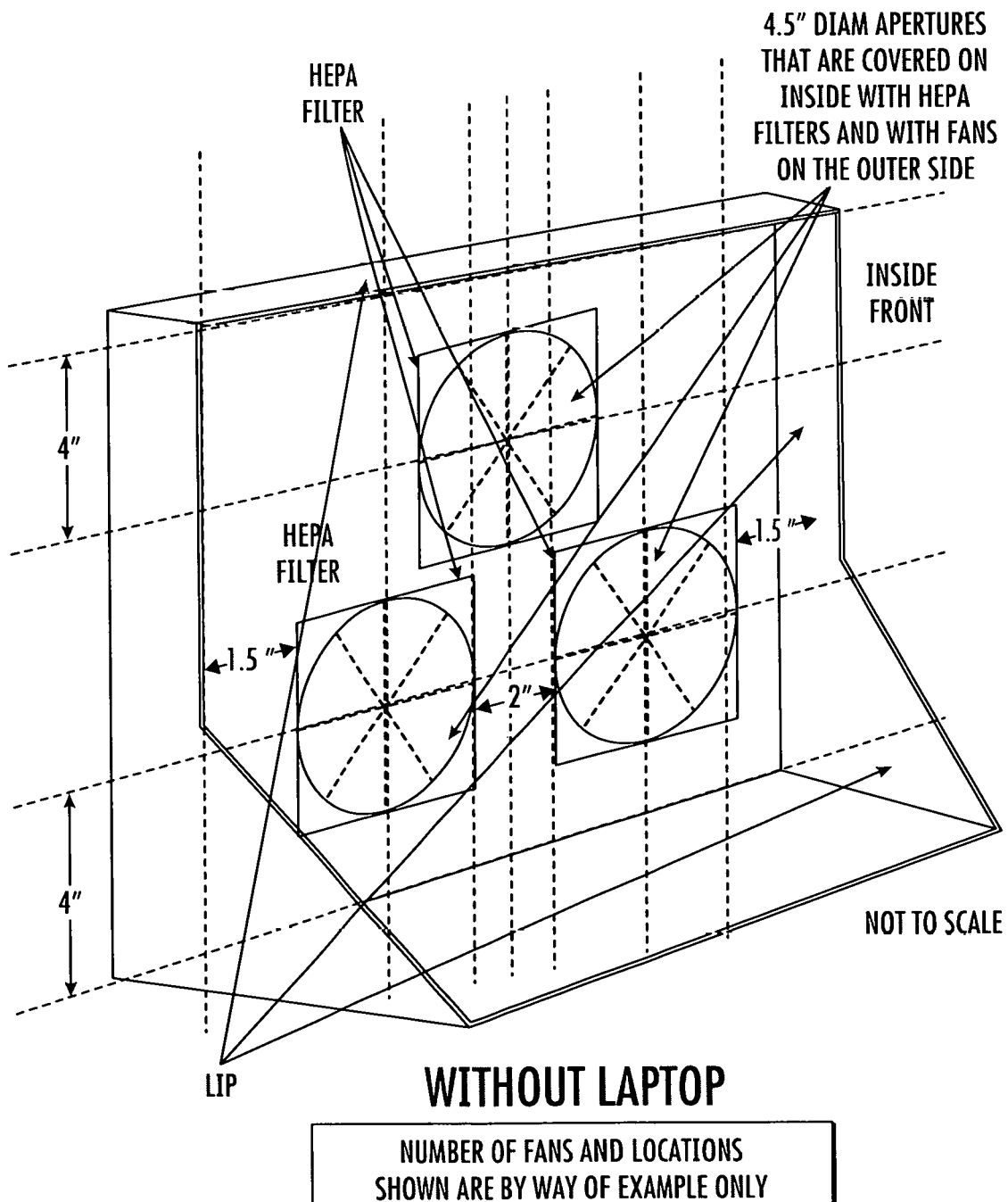
FIG. 44 is a depiction of an embodiment of the current invention, showing an exhaled air collector with exhaled air purification laptop docking station, but the laptop is not in or connected to the docking station. This depiction shows a recessed exhaled air collector into which can be placed the laptop screen, and the back of the station shows fans associated with HEPA filters for cleaning the exhaled air and room air that is captured by the system.

In embodiments, the exhaled air collector can be that of a laptop docking station, whereby the back of the docking station can act as an exhaled air blocking surface deflecting exhaled air towards an air suction intake that leads to a filter, by way of example only, a HEPA filter. (See, e.g., FIG. 42.) When a laptop is positioned within the exhaled air cleaning laptop docking station, the front of the screen of the laptop can also act as an exhaled air blocking surface. (See, e.g., FIG. 43.) There can be a space for air to circulate between the back of the laptop and the inside front surface of the back of the exhaled air cleaning laptop docking station. (See, e.g., FIG. 42, FIG. 43, FIG. 44.) There can be a space for air to circulate between the side walls of the exhaled air cleaning laptop docking station and the sides of the laptop. (See, e.g., FIG. 42, FIG. 43, FIG. 44.) The exhaled air cleaning laptop docking station can comprise an optional back, two or more side walls, optional top, optional exhaled air guide, an optional bottom, and an open front. The exhaled air purification chamber can be located within or on the back of the laptop docking station. (See, e.g., FIG. 44.) One or more fans can be located on the inside surface of the back or can be located on the backside surface of the back. (See, e.g., FIG. 44.) A filter or filters, by way of example only a HEPA filter(s), can be located forward of the fan or fans. (See, e.g., FIG. 44.) A CO2 reducer can be located forward of the filter or filters. The exhaled air cleaning laptop docking station can comprise a switch and/or sensor(s) so that when the laptop is placed within the laptop docking station the exhaled air collector and exhaled air purification chamber become operable, and when the laptop is taken out of the laptop docking station it turns itself off. The exhaled air cleaning laptop docking station can comprise a CO2 sensor. The exhaled air cleaning laptop docking station can comprise an IR sensor, photosensor, motion sensor, or any combination thereof. In embodiments, the top of the laptop docking station can have an adjustable exhaled air guide. The laptop docking station can be transparent, semi-transparent, or any color desired. While the above refers to an exhaled air cleaning laptop docking station for a laptop, the same configuration can be used for a computer tablet or a mobile communication device. Thus, in this case, the exhaled air cleaning laptop docking station would be that of an exhaled air cleaning computer tablet docking station or a mobile communication device docking station.

As used herein, an airborne particulate can be that of, but is not limited to, a virus, a bacteria, a fungus, a pathogen, a pollutant, or a contaminant. As used herein, a pathogen can include a bacteria, a fungi, a protozoa, worms, viruses, and/or infectious proteins called prions. As used herein, "seat," "chair," "bench," and "sitting apparatus," have the same meaning and can be used interchangeably. As used herein, the word "clean" or variations thereof can have the same meaning as purify. Clean air can mean the same as cleaned air. Cleaned air can be that of filtered air. Cleaned air can be that of purified air. Cleaned air can be that of sterilized or sanitized air. The words purify and/or clean can imply that of partially cleaned, partially purified, or fully cleaned and fully purified. As used herein, an exhaled air purifier can mean the same thing as an exhaled air purification chamber. As used here in an air purification chamber can include an air purifier. Such exhaled air cleaning/purification can occur by way of one or more of filtration, chemical microbicidal purification, light microbicidal purification (such as, by way of example only, UVC light), mechanical microbicidal purification, thermal microbicidal purification, microbicidal agents, or microbicidal materials. Filtration can be by way of any filtration device or member such as by way of example only a HEPA filter. A HEPA filter can be that of any series or grades of HEPA filters. A filter can employ a microbicidal or anti-microbial agent, material, or coating. It is understood and implied herein that when exhaled air is collected and cleaned or purified, air from the room and/or venue can also be mixed with the collected exhaled air. An air purification unit comprises both an exhaled air collector and an exhaled air purification chamber. An air purification system comprises a plurality of air purification units. Thus, when using the terms exhaled air collector, exhaled air purification chamber, or exhaled air purification unit, it is understood that the collector, chamber, and purification unit can be handling and processing both exhaled air and that of the venue's room air. As used herein, an exhaled purification system or air purification system can mean the same thing as an exhaled air purification system. As used herein, an air purification unit can mean the same as an air purification device. As used herein, a CO2 reducer is that of any means of reducing CO2 from the air of the room and/or from exhaled air. Such a means can be, by way of example only, living plant or plants, CO2 absorbing materials, CO2 being absorbed and reclaimed with Nitrogen, passing air through a stack of charged electrochemical plates, or a CO2 filter.

An electronic display screen, computer screen, video display screen, television ("TV") screen, display screen, or computer monitor comprising an electronic display screen can all have the same meaning. As used herein, someone that is sitting or standing "in front" of an exhaled air purification unit can be exemplified by someone sitting or standing at a table as depicted in the figures included with this invention disclosure. As used herein, someone sitting behind a chair, seat, or bench is sitting in the chair, seat, or bench behind that of the chair, seat, or bench that is in front thereof. As used herein, the back of a chair, seat, or bench is the backrest and/or headrest of the chair, seat, or bench. And as used herein, a computer screen can be the screen used, by way of example only, one of or more of a desktop computer, a laptop computer, a tablet computer, a cellphone, a mobile phone, a TV screen, and/or exercise equipment. As used herein, a computer monitor can include the frame and any additional members that surround or house a computer screen of the computer monitor. However, in the general sense, as used herein, a computer monitor can mean the same thing as a computer screen and a computer screen can mean the same as a computer monitor. In embodiments, the computer screen or display screen can be supported by a support member that is attached to the computer screen, display screen, or computer monitor. An air suction conduit that connects the exhaled air collector to an air purification chamber can bifurcate into two or more conduits that travel across a right side and/or a left side of the support member. In embodiments, a computer monitor, computer screen, or display screen can be supported by one or more air purification chambers that is/are attached to the computer screen. In embodiments, a computer monitor, computer screen, or display screen can be integrated with an exhaled air collector, an exhaled air purification chamber, and/or an exhaled air purifier. In embodiments, a computer monitor, computer screen, or display screen can be integrated with a traditional or conventional air purifier. In embodiments, a computer monitor, computer screen, or display screen can be attached to a traditional or conventional air purifier. In embodiments, a computer monitor, computer screen, or display screen can be releasably attachable to a traditional or conventional air purifier. As used herein, an air purifier can utilize a filtration and/or other microbicidal means to destroy and/or clean the air of particulates. As used herein, an exhaled air purification chamber can be that of an exhaled air purifier. And an exhaled air purifier can that of an exhaled air purification chamber.

As used herein, the abbreviation "CADR" is basically a reflection of the air flow (CFM—cubic feet per minute) times the efficiency of the air filter. So, if an air filter has 200 CFM and 100% efficiency, the CADR would be 200. If the air filter has 200 CFM and 75% efficiency, the CADR would be 150. As used herein, "CFM" means cubic feet per minute of air flow.

In another embodiment, a traditional or conventional air purifier known in the art can be attached to, combined with, or have integrated by engineering design a CO2 reducer such as, by way of example only, a living plant or plant. Such an integration can be by way of a retrofittable kit that attaches or combines in any manner a CO2 reducer with an air purifier. In cases, the CO2 reducer is placed in front of the traditional or conventional air purifier's filter, or, said another way, before air flow strikes or otherwise enters the traditional or conventional air purifier's filter (such as, by way of example only, a HEPA filter). In embodiments, a container that supports, holds, or houses a living plant or plant (or other type of CO2 reducer) can be attached to the outside surface air suction portion of the air purifier. In embodiments, a container that supports, holds, or houses a living plant or plant (or other type of CO2 reducer) can be attached to a surface of the traditional or conventional air purifier. The container can comprise a florescent light or grow light. The container can hold moisture or water. In embodiments, the traditional or conventional air purifier can comprise a florescent, light or grow light. In embodiments, a CO2 reducer can be incorporated within the traditional or conventional air purifier.

In an embodiment, a traditional or conventional air purifier comprises a filter and a CO2 reducer. The filter can be that of any filter including that of a HEPA filter, and the CO2 reducer can be that of any CO2 reducer, such as, by way of example only, a living plant or plants, CO2 absorbing materials, CO2 being absorbed and reclaimed with Nitrogen, and/or passing air through a stack of charged electrochemical plates.

Figure 15:
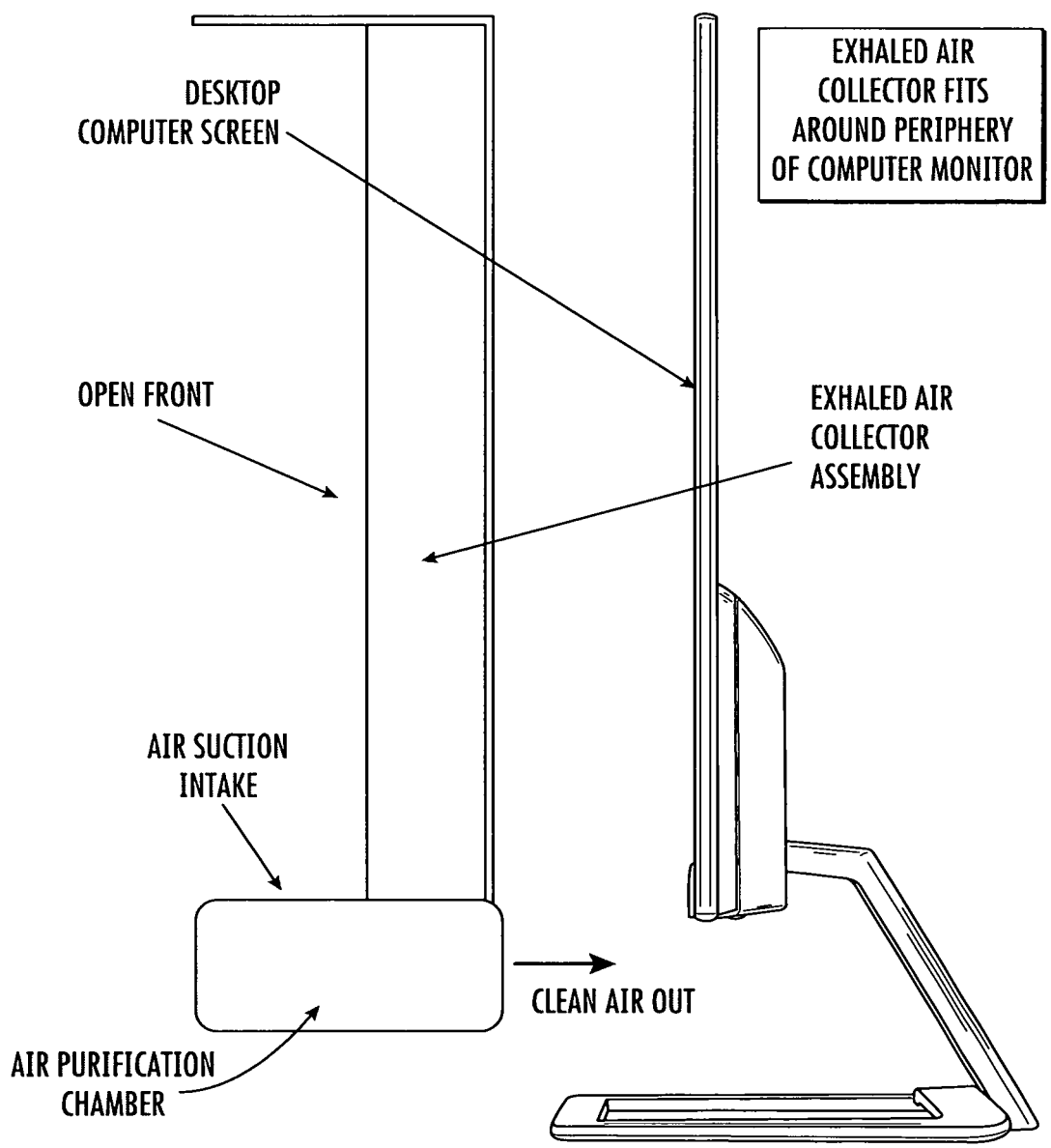
FIG. 15 is a depiction of an embodiment of the current invention, showing a monitor with an exhaled air collector assembly for retrofitting a monitor with the current invention. In aspects, the exhaled air collector can fit around a periphery of a computer monitor or screen.
Figure 16:
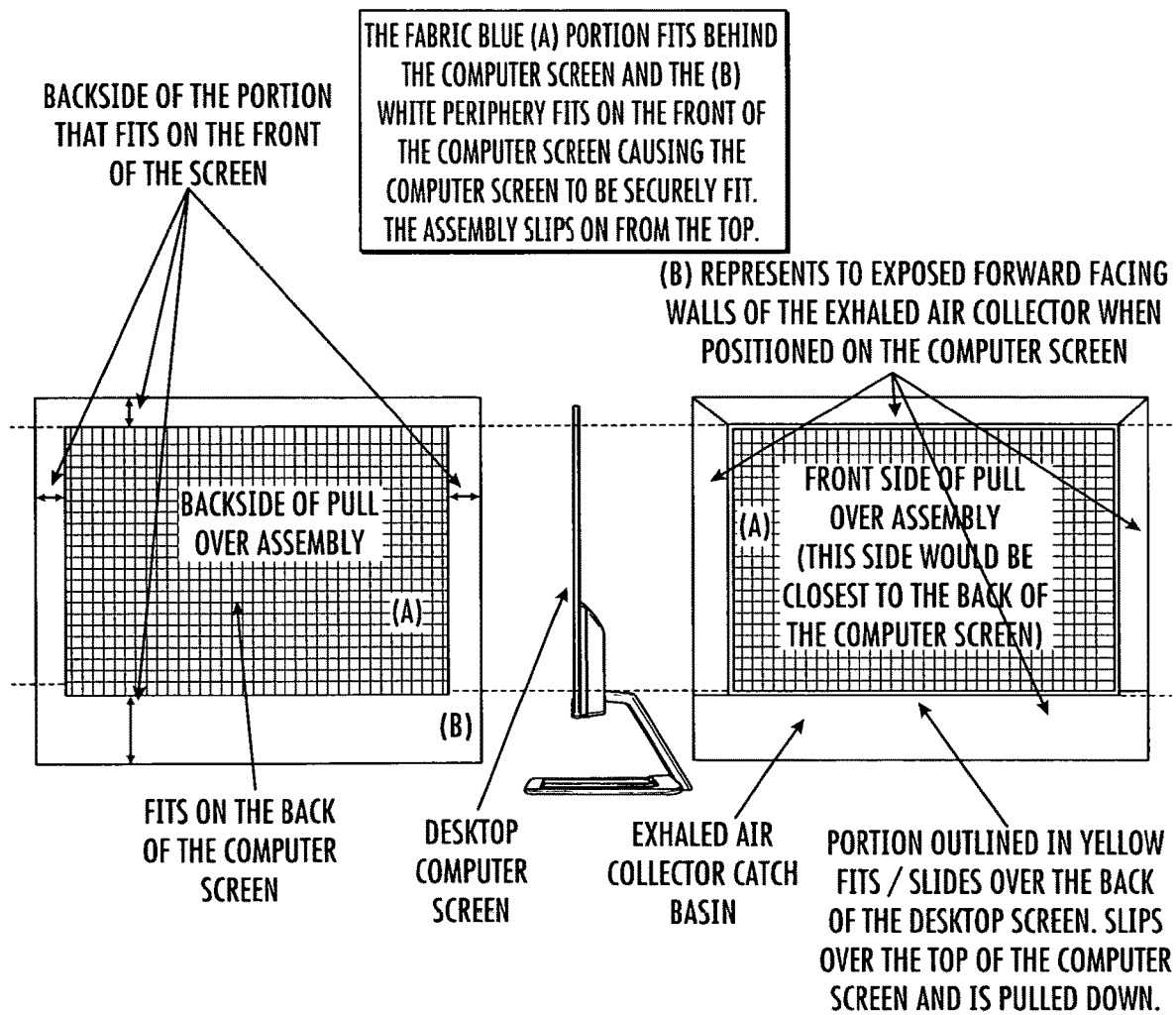
FIG. 16 is a depiction of an embodiment of the current invention, showing a monitor with an exhaled air collector assembly for retrofitting a monitor with the current invention. In this case, the fabric blue (A) portion fits behind the computer screen and the (B) white periphery fits on the front of the computer screen causing the computer screen to be securely fit. In aspects, the assembly slips on from the top.

In another embodiment, an exhaled air collector and exhaled air purification chamber and/or exhaled air collector are formed as that of an open-front box that is larger in outer dimensions than that of the computer monitor, computer monitor's screen, or a display screen. In embodiments, the outer dimensions are 0.12 inches or greater for that of the exhaled air collector and/or exhaled air purification chamber as compared to that of the dimensions of the computer monitor, computer monitor's screen, or display screen. The open-front box can follow the topography of the back of the computer monitor, computer monitor's screen, or display screen. The open-front box can be that of any shape and dimension that provides a horizontal, vertical, and depth dimension such that the computer monitor, computer monitor's screen, or display screen can fit within the open-front box. The back of the computer monitor can fit within the portion of the exhaled air collector that includes exhaled air purification components, such as, by way of example only, a HEPA filter. In other embodiments, the back of the computer monitor can fit within the exhaled air purification chamber. In cases, a portion of the back of the computer monitor can touch the inside back of the exhaled air purification chamber. In other cases, there is some separation. The exhaled air collector portion of this embodiment can be the sides of the open-front box combined with the display screen's exhaled air blocking surface. The back of this open-front box can be that of the exhaled air purification chamber. The open space around the periphery of the computer monitor between that of the computer monitor or display and that of the walls of the exhaled air collector can be an exhaled air suction intake. The exhaled air purification chamber or air purifier can comprise one or a plurality of fans along with one or a plurality of filters, by way of example only, HEPA filters. The exhaled air purification chamber or air purifier can comprise any filtration and/or microbicidal material, agent, or means for cleaning the air. The exhaled air purification chamber or air purifier can provide for a CADR of 10 CADR or greater. The exhaled air purification chamber or air purifier can provide for a CADR of 50 CADR or greater. The exhaled air purification chamber or air purifier can provide for a CADR of 100 CADR or greater. The exhaled air collector/exhaled air purification chamber can be supported and attached to the computer monitor or display screen stand. The exhaled air collector/exhaled air purification chamber can be attached to the computer monitor or display screen. The exhaled air collector/exhaled air purification chamber can be free standing and supported by its own tabletop, desktop, or wall support. The exhaled air collector/exhaled air purification chamber can be that of an attachable kit or assembly for attaching to a computer monitor or display screen. (See, e.g., FIG. 11, FIG. 15, FIG. 16.) The exhaled air collector/exhaled air purification chamber can be fabricated in such a way that it is integrated with or incorporated to a computer monitor or display screen.

In other embodiments, a traditional or conventionally-known air purifier can be designed in such a way that all or a portion thereof can be one of placed under, attached to, releasably attachable to, incorporated into, or integrated into the lower front edge of a computer screen or computer monitor. In this case the traditional or conventional air purifier can comprise an outer shape and size such that its horizontal length is 12 inches or longer and its vertical height is 8 inches or shorter. Thus, its horizontal length in cases can be 2 times or more than its vertical height. In addition, the traditional or conventional air purifier can comprise a horizontal air suction intake that is located over a portion or all its horizontal length that is parallel and aligned with the horizontal lower edge of the computer screen or computer monitor when placed under the lower edge of the computer screen or computer monitor. In cases, the traditional or conventional air purifier can be used in association with downward air from that of a fan, fans, or fan strip that is attached to the sides or top of the computer screen. In other cases, the traditional or conventional air purifier is used to capture some or all the exhaled air of a user of the computer screen or computer monitor. In other cases the traditional or conventional air purifier is used in association with an exhaled air collector. In still other cases the traditional or conventional air purifier can be used as part of an exhaled air collector. In still other cases the traditional or conventional air purifier is incorporated within the computer monitor. And in still other cases a computer monitor can comprise a traditional or conventional air purifier.

Figure 2:
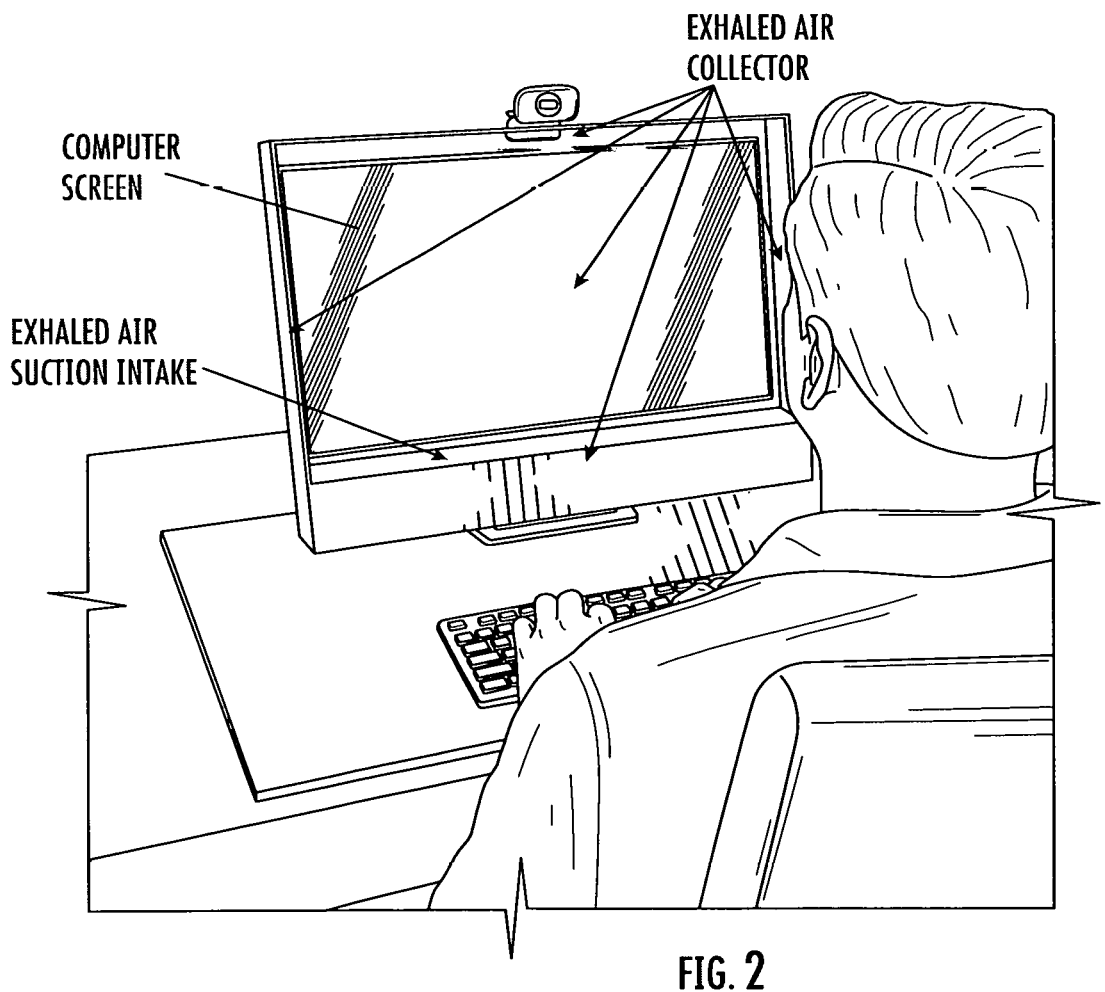
FIG. 2 is a depiction of an embodiment of the current invention, such as a computer monitor with exhaled air collector and air purification chamber (not visible in this depiction).
Figure 3:
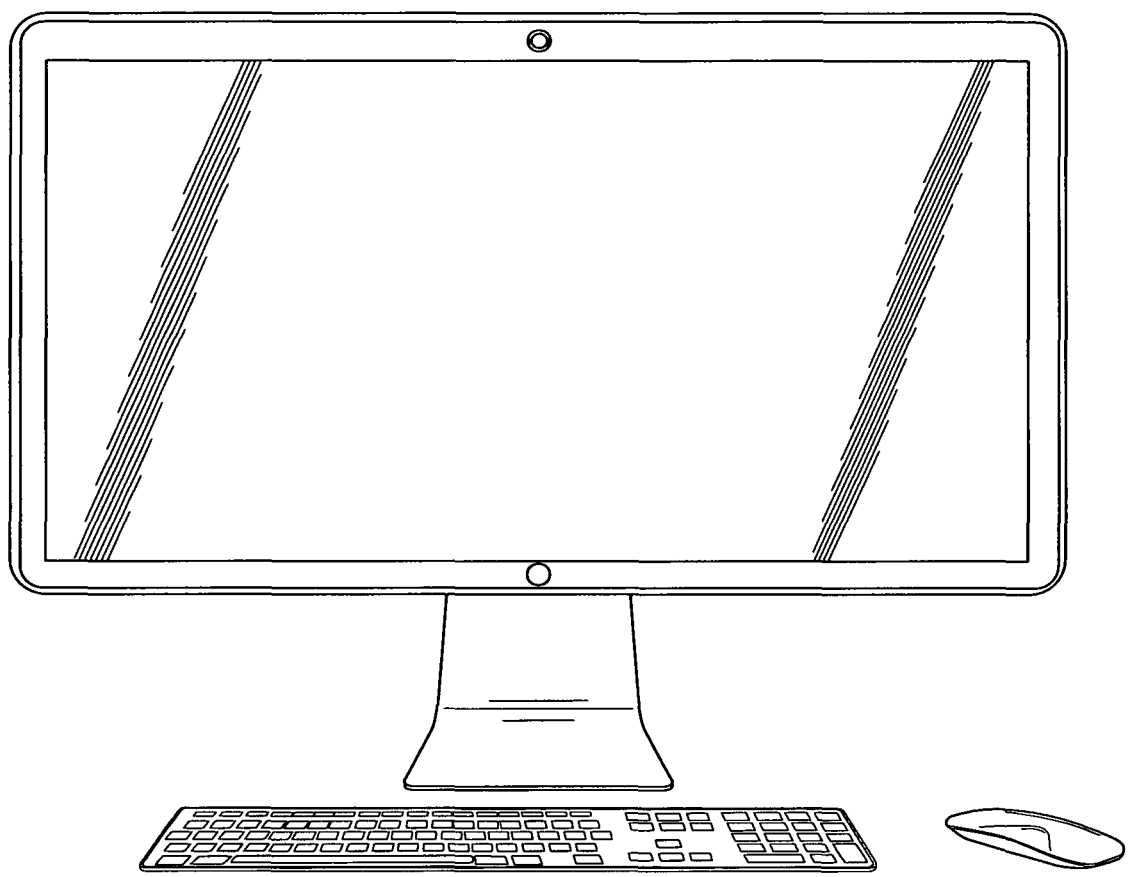
FIG. 3 shows a desktop computer monitor having a computer monitor display screen/electronic display screen.
Figure 4:
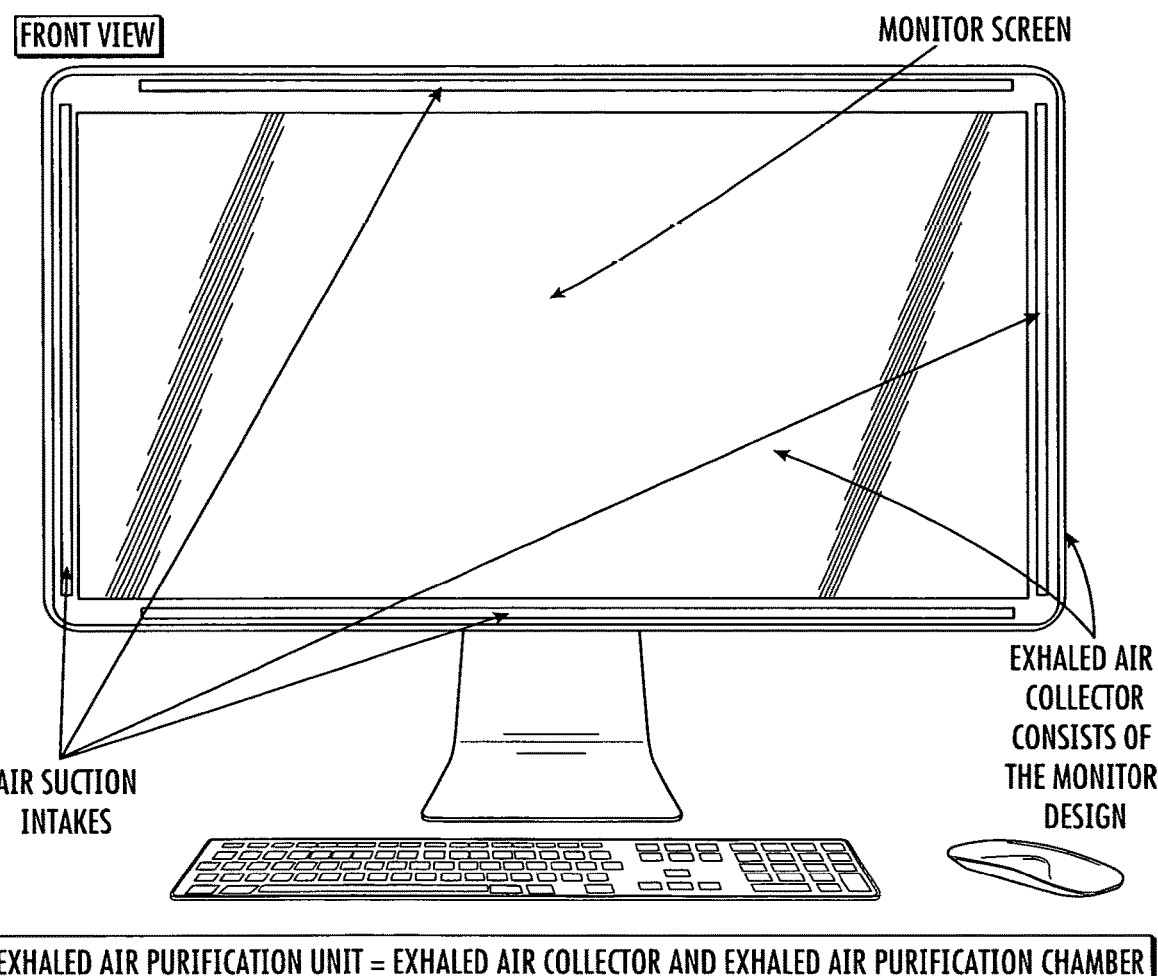
FIG. 4 is a depiction of an embodiment of the current invention, showing a monitor with a built in exhaled air purification unit.
Figure 5:
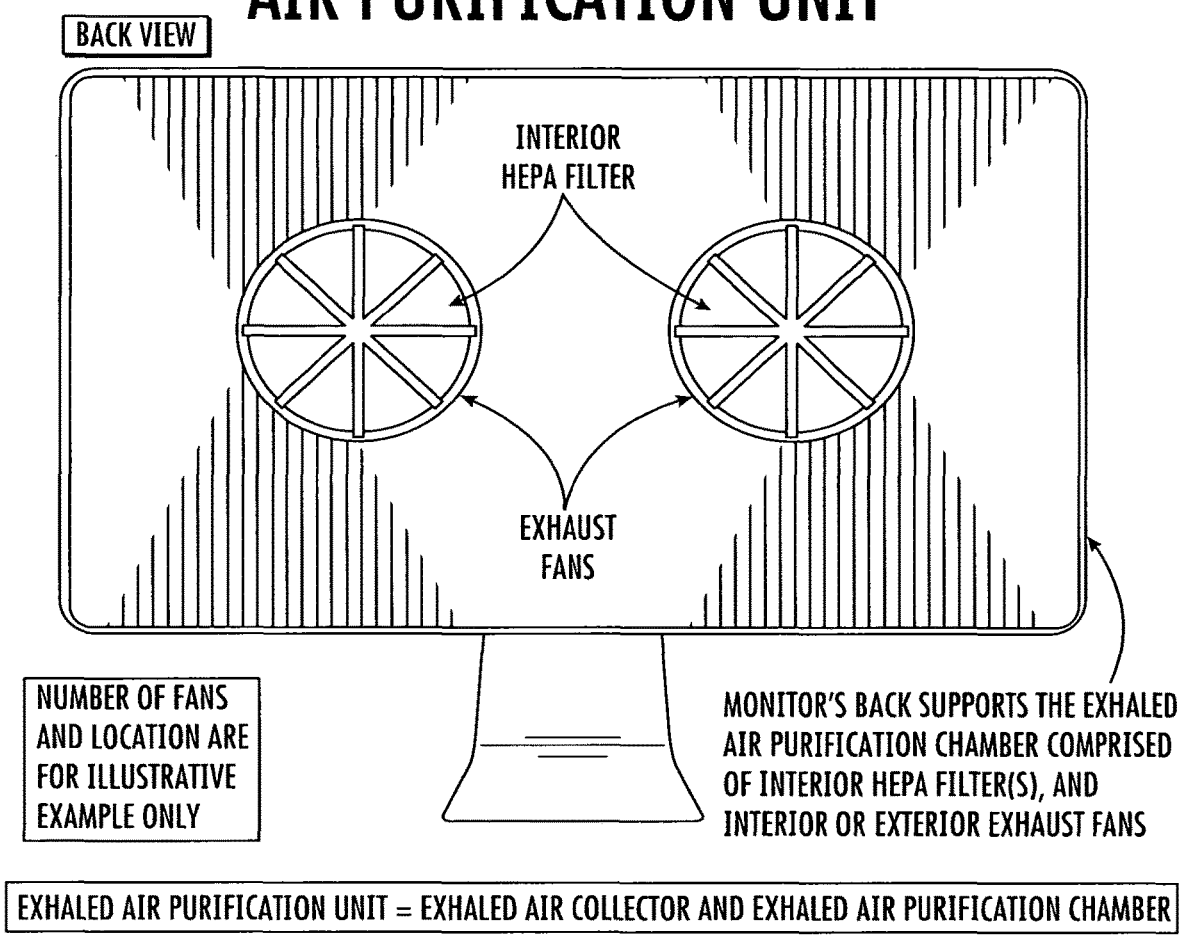
FIG. 5 is a depiction of an embodiment of the current invention, showing a monitor with a built in exhaled air purification unit.
Figure 6:
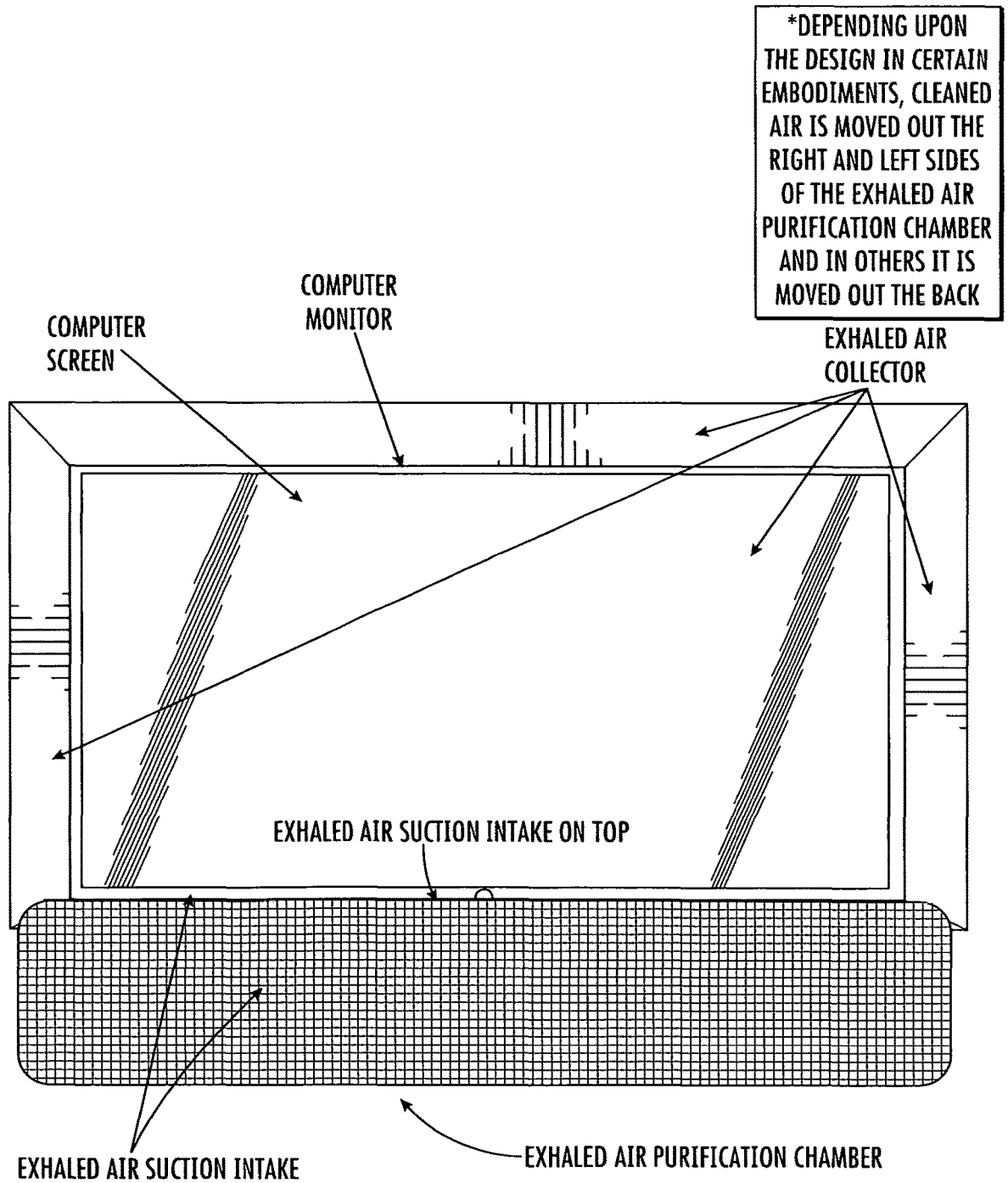
FIG. 6 is a depiction of an embodiment of the current invention, showing a monitor with an integrated exhaled air purification unit.

An embodiment of the present invention is that of a computer monitor, computer monitor's screen, or electronic display screen, wherein the computer monitor, the computer monitor's screen, or the electronic display screen houses, supports, incorporates, integrates, partially or fully surrounds, connects to, attaches to, or releasably attaches to an exhaled air collector, becomes part of the exhaled air collector, wherein a front surface of the computer monitor's screen or the electronic display screen provides an exhaled air blocking surface. (See, e.g., FIG. 1.) In aspects, when the exhaled air collector is separated from a display screen or monitor the exhaled air collector can resemble a shell or open front box. When the exhaled air collector is attached or built into the monitor or display screen the front of the display screen becomes part of the exhaled air collector. (See, e.g., FIG. 2.) In embodiments, the exhaled air collector collects exhaled air and room air and the exhaled air blocking surface deflects and/or directs exhaled air towards an exhaled air suction intake. In aspects, the exhaled air suction intake directs exhaled air and room air towards an exhaled air suction conduit and/or an exhaled air purification chamber. The exhaled air collector and/or exhaled air purification chamber can be attached to, releasably attached to, incorporated into, or integrated with a computer monitor stand.

The exhaled air suction intake can be formed around a portion of, or all the periphery of, a computer monitor, a computer monitor's screen, or a display screen. The air suction intake can be connected to an air suction conduit or an exhaled air purification chamber. The air suction intake can be located adjacent to or within the front or a side of an exhaled air purification chamber. The exhaled air purification chamber can be integrated with, incorporated into, attached to, or releasably attached to the computer monitor. The exhaled air collector and/or the exhaled air purification chamber can be an assembly that is attachable to a computer monitor, computer monitor's screen, display screen, or computer monitor stand. The exhaled air collector and/or exhaled air purification chamber can be supported by a desktop, a tabletop, or a wall support member of the computer monitor, computer monitor's screen, or display screen. The exhaled air collector can be supported by an air purification chamber. The exhaled air collector can be larger in outer dimensions than one or more dimensions of the computer monitor, computer monitor's screen, or display screen. The computer monitor, computer monitor's screen, or display screen can fit within a portion of or all of the exhaled air collector.

The exhaled air collector can comprise one or more fans that move air across the front of one of the computer monitor, computer monitor's screen, or display screen. The exhaled air collector can comprise one or more fans that move air towards an air suction intake.

The exhaled air collector, computer monitor, or display screen can comprise a sensor (by way of example only, a thermal sensor or a motion sensor), wherein the sensor is capable of sensing when an individual is sitting or standing in front of the computer monitor or display screen. The exhaled air collector, computer monitor, or display screen can comprise a CO2 sensor, wherein upon meeting, exceeding, or satisfying a certain threshold of sensed CO2, the sensor can trigger an increase of the CADR of a connected, attached, or integrated exhaled air purification chamber. The exhaled air collector, computer monitor, or display screen can comprise an acoustic sensor, wherein upon meeting, exceeding, or satisfying a certain threshold of a sound (for example, a minimum or maximum amount of decibels)

made by the user of the exhaled air collector, the computer monitor, or display screen, the acoustic sensor can trigger an increase of the CADR of a connected, attached, or integrated exhaled air purification chamber. The sound being sensed can be, for example, an exhaled breath, a cough, or a sneeze.

The exhaled air collector or air suction intake can comprise, house, support, incorporate, integrate with, be attached to, or be releasably attached to a CO2 reducer. The CO2 reducer can be a living plant. The computer monitor or display screen or an attachment thereto, can assist in the cleaning of exhaled air and room air by reducing the level of pathogens, CO2, contaminants, and/or pollutants.

Figure 27:
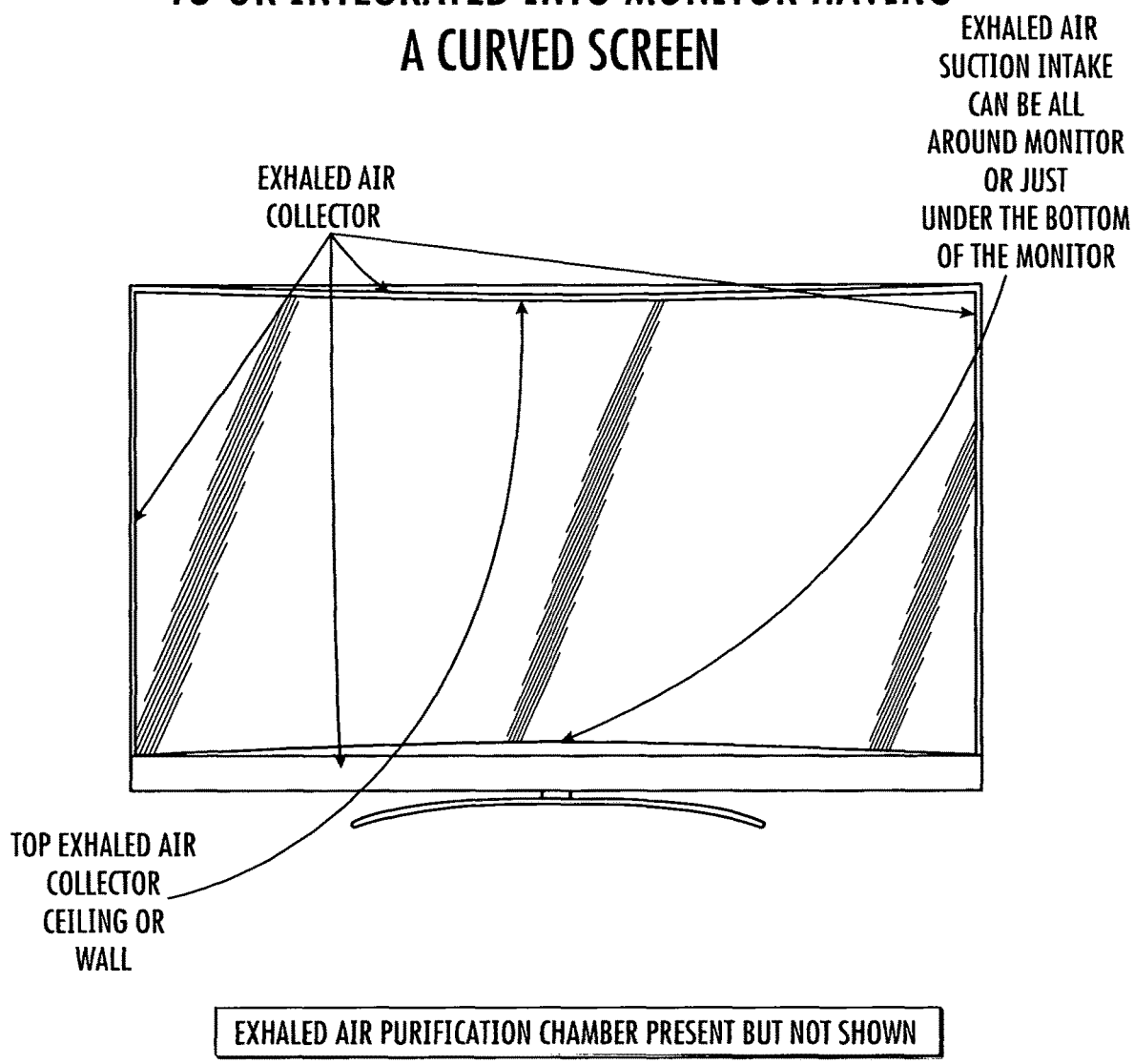
FIG. 27 is a depiction of an embodiment of the current invention, showing a curved monitor with an integrated or attached exhaled air collector or exhaled air purification unit.
Figure 28:
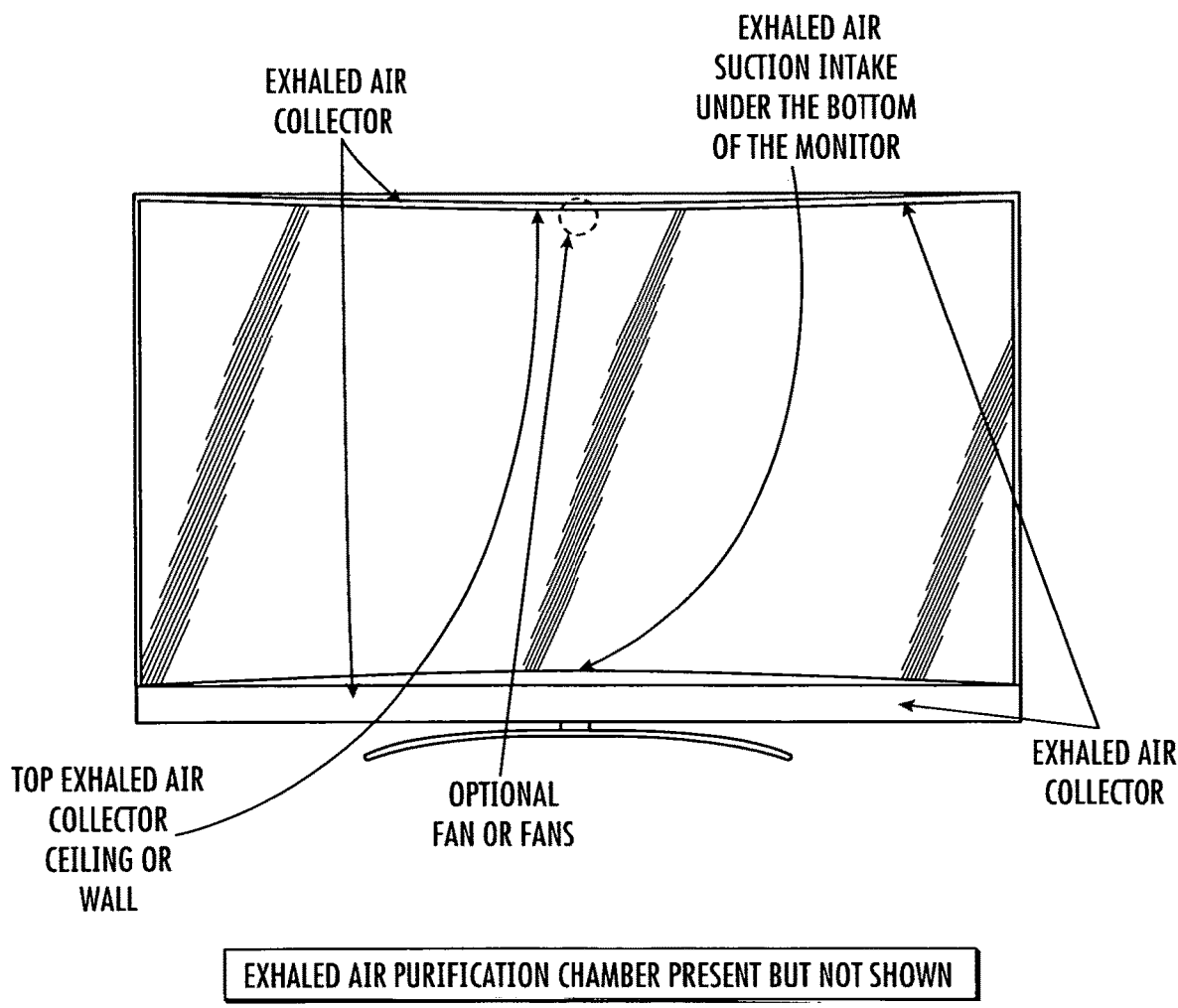
FIG. 28 is a depiction of an embodiment of the current invention, showing a curved monitor with an integrated or attached exhaled air collector or exhaled air purification unit.
Figure 29:
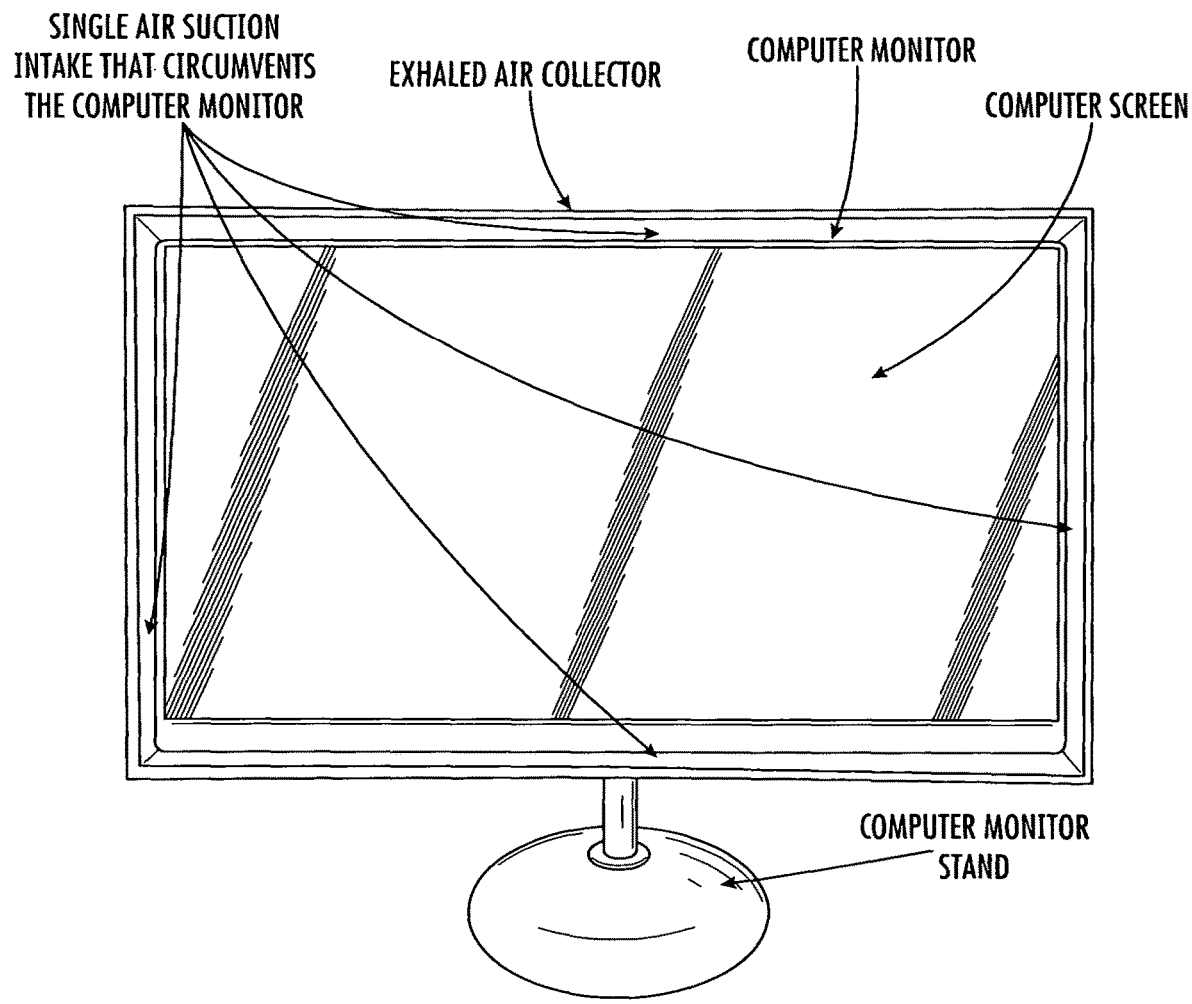
FIG. 29 is a depiction of an embodiment of the current invention, showing a monitor with an integrated or attached exhaled air purification unit.

The computer monitor, computer monitor's screen, or display screen can comprise or be that of a curved display screen. (See, e.g., FIG. 27, FIG. 28.) The exhaled air purification chamber can comprise one or more of a filter, a HEPA filter, a microbicidal agent, a microbicidal light, a microbicidal material, a microbicidal chemical, a microbicidal agent, or a microbicidal heat.

The exhaled air collector and/or air suction intake can comprise one or more fans. The exhaled air purification chamber and/or exhaled air suction conduit can comprise one or more fans.

The exhaled air collector can comprise, one or more of, in aspects, a fully/completely or mostly open front, a fixed open front, an uncovered open front, an exhaled air catch basin, and exhaled air suction intake(s), an exhaled air guide, a fan or fans, and/or an outer lip. The exhaled air collector and air purification chamber can be that of an attachable kit. The computer monitor, computer monitor's screen, or display screen can be a cash register screen or monitor, a gambling screen or monitor, an exercise equipment/workout equipment screen or monitor, a vehicle seat screen or monitor, a theater seat screen or monitor, a classroom screen or monitor, an aircraft seat screen or monitor, a laptop screen or monitor, a desktop computer screen or monitor, or a tablet screen or monitor. The computer monitor or display screen can be that of any computer monitor or display screen that comprises a micro-chip or computer chip.

Another embodiment can be that of a computer monitor stand that comprises, integrates, houses, supports, is attached to, or is releasably attached to an exhaled air collector, exhaled air purification chamber, or both. A computer monitor can comprise, integrate, house, support, be attached to, or be releasably attached to an exhaled air collector, an exhaled air purification chamber, or both. The computer monitor can comprise, house, or support a filter and/or a HEPA filter.

Another embodiment is that of a computer monitor, computer monitor's screen, or display screen, wherein the computer monitor, the computer monitor's screen, or the display screen houses, supports, incorporates, integrates, partially or fully surrounds, is connected to, is attached to, or is releasably attached to, a traditional or conventional air purifier. The traditional or conventional air purifier can be attached to, releasably attached to, incorporated with, and/or integrated with, a computer monitor stand. The traditional or conventional air purifier can be formed around a portion of, or all the periphery of, a computer monitor, a computer monitor's screen, or a display screen. The traditional or conventional air purifier can be connected to an air suction conduit or an exhaled air purification chamber. The traditional or conventional air purifier can be located adjacent to or within the front or a side of an exhaled air purification chamber. The traditional or conventional air purifier can be integrated with, incorporated into, attached to, or releasably attached to the computer monitor. The traditional or conventional air purifier can be an assembly that is attachable to a computer monitor, a computer monitor's screen, a display screen, or a computer monitor stand. The traditional or conventional air purifier can be supported by a desktop, a tabletop, or a wall support member of the computer monitor, computer monitor's screen, or display screen. The traditional or conventional air purifier can be supported by an air purification chamber. The computer monitor, computer monitor's screen or display screen can be supported by the traditional or conventional air purifier. The traditional or conventional air purifier can be larger in outer dimensions than one or more dimensions of the computer monitor, computer monitor's screen, or display screen. The traditional or conventional air purifier can comprise one or more fans that move air towards an air suction intake. The traditional or conventional air purifier can comprise a sensor (by way of example only, a thermal sensor or a motion sensor), wherein the sensor is capable of sensing when an individual is sitting or standing in front of the computer monitor or display screen. The traditional or conventional air purifier can comprise a CO2 sensor, wherein upon meeting, exceeding, or satisfying a certain threshold of sensed CO2, the sensor can trigger an increase of the CADR of a connected, attached, or integrated exhaled air purification chamber. The computer monitor or display screen can comprise an acoustic sensor, wherein upon meeting, exceeding, or satisfying a certain threshold of a sound made by the user of the computer monitor or display screen, the acoustic sensor can trigger an increase of the CADR of a incorporated, integral, connected, attached, or releasably attachable traditional or conventional air purifier. The sound being sensed can be, for example, an exhaled breath, a cough, or a sneeze. The traditional or conventional air purifier can comprise, house, support, incorporate, be attached to, or be releasably attached to, a CO2 reducer. The CO2 reducer can be a living plant. The traditional or conventional air purifier can assist in the cleaning of exhaled air and room air by reducing the level of pathogens, CO2, contaminants, and/or pollutants. The computer monitor, computer monitor's screen, or display screen can comprise or be that of a curved display screen. The traditional or conventional air purifier can comprise one or more of a filter, a HEPA filter, a microbicidal agent, a microbicidal light, a microbicidal material, a microbicidal chemical, a microbicidal agent, or a microbicidal heat. The traditional or conventional air purifier can comprise one or more fans. The traditional or conventional air purifier can be that of an attachable kit. The computer monitor, computer monitor's screen, or display screen to which a traditional or conventional air purifier is attached, incorporated within, integral with, or releasably attachable to can be a cash register screen or monitor, a gambling screen or monitor, an exercise equipment/workout equipment screen or monitor, a vehicle seat screen or monitor, a theater seat screen or monitor, a classroom screen or monitor, an aircraft seat screen or monitor, a laptop screen or monitor, a desktop computer screen or monitor, or a tablet screen or monitor. The computer monitor or display screen can be that of any computer monitor or display screen that comprises a micro-chip or computer chip. Another embodiment is that of a computer monitor stand, that comprises, integrates, houses, supports, is attached to, or is releasably attached to a traditional or conventional air purifier. The computer monitor can comprises, house, or support a filter, by way of example only, a HEPA filter.

The present invention can be described in terms of Aspects:

Aspect 1: An air cleaning system comprising the following components:
- a) a monitor, a computer monitor, a computer monitor screen, or an electronic display screen having a front surface comprising, providing, or acting as an exhaled air blocking surface for deflecting and/or directing exhaled air of a user towards an exhaled air suction intake;
- b) an exhaled air collector housed by, supported by, incorporated into, integrated with, partially or fully surrounding, connected to, attached to, or releasably attached to the monitor, the computer monitor, the computer monitor screen, or the electronic display screen, said exhaled air collector providing for capturing or collecting exhaled air of the user and room air;
- c) said exhaled air suction intake providing for suctioning of the exhaled air of the user and the room air towards, into, or through a filler, an exhaled air suction conduit, an exhaled air purification chamber, or any combination thereof.

Aspect 2: The air cleaning system of Aspect 1, wherein the exhaled air collector, the exhaled air purification chamber, or both, are attached to, releasably attached to, incorporated into, or integrated with, a computer monitor stand.

Aspect 3: The air cleaning system of Aspect 1, wherein the exhaled air suction intake is formed around a portion of or all of a periphery of the computer monitor, the computer monitor screen, or the electronic display screen.

Aspect 4: The air cleaning system of Aspect 1, wherein the exhaled air suction intake and/or a second exhaled air suction intake is connected to the air suction conduit or the exhaled air purification chamber.

Aspect 5: The air cleaning system of Aspect 1, wherein the exhaled air suction intake and/or a second exhaled air suction intake is located adjacent to or within a front or a side of the exhaled air purification chamber.

Aspect 6: The air cleaning system of Aspect 1, wherein the exhaled air purification chamber is integrated with, incorporated into, attached to, or releasably attached to the computer monitor.

Aspect 7: The air cleaning system of Aspect 1, wherein the exhaled air collector, the exhaled air purification chamber, or both, are an assembly capable of being attached to the computer monitor, the computer monitor screen, the electronic display screen, or a computer monitor stand.

Aspect 8: The air cleaning system of Aspect 1, wherein the exhaled air collector, the exhaled air purification chamber, or both, are supported by a desktop, a tabletop, or a wall support member of the computer monitor, the computer monitor screen, or the electronic display screen.

Aspect 9: The air cleaning system of Aspect 1, wherein the exhaled air collector is supported by the air purification chamber and/or a second air purification chamber.

Aspect 10: The air cleaning system of Aspect 1, wherein the exhaled air collector is larger in outer dimensions than the computer monitor, the computer monitor screen, or the electronic display screen.

Aspect 11: The air cleaning system of Aspect 1, wherein the computer monitor, the computer monitor screen, or the electronic display screen fit within a portion of or all of the exhaled air collector.

Aspect 12: The air cleaning system of Aspect 1, wherein the exhaled air collector comprises one or more fans for moving the exhaled air of the user air across a front surface of the computer monitor, the computer monitor screen, or the electronic display screen.

Aspect 13: The air cleaning system of Aspect 1, wherein the exhaled air collector comprises one or more fans that blow or move air towards the air suction intake.

Aspect 14: The air cleaning system of Aspect 1, wherein the exhaled air collector, the computer monitor, the computer monitor screen, the electronic display screen, or combinations thereof, comprise one or more sensors, wherein the sensor is capable of sensing when an individual is sitting or standing in front of the computer monitor, the computer monitor screen, or the electronic display screen.

Aspect 15: The air cleaning system of Aspect 1, wherein the exhaled air collector, the computer monitor, the computer monitor screen, or the electronic display screen comprise a carbon dioxide sensor, wherein if a predetermined amount of carbon dioxide is met or exceeded, the air cleaning system causes an increase of the clean air delivery rate ("CADR") of the exhaled air purification chamber.

Aspect 16: The air cleaning system of Aspect 1, wherein the exhaled air collector, the computer monitor, the computer monitor screen, or the electronic display screen comprise an acoustic sensor, wherein if predetermined noise level is met or exceeded, the air cleaning system causes an increase of the clean air delivery rate ("CADR") of the exhaled air purification chamber.

Aspect 17: The air cleaning system of Aspect 16, wherein the noise being sensed is an exhaled breath, a cough, a sneeze, or combinations thereof.

Aspect 18: The air cleaning system of Aspect 1, wherein the exhaled air collector, the air suction intake, or both, comprise, house, support, incorporate, are attached to, or are releasably attached to a carbon dioxide reducer.

Aspect 19: The air cleaning system of Aspect 18, wherein the carbon dioxide reducer is a living plant.

Aspect 20: The air cleaning system of Aspect 1, wherein the computer monitor, the computer monitor screen, or the electronic display screen, and/or an attachment to the computer monitor, the computer monitor screen, or the electronic display screen, assists in cleaning the exhaled air of the user and the room air by causing a reduction of a level of pathogens, carbon dioxide, contaminants, pollutants, particulates, or combinations thereof.

Aspect 21: The air cleaning system of Aspect 1, wherein the computer monitor, the computer monitor screen, or the electronic display screen comprise a curved display screen.

Aspect 22: The air cleaning system of Aspect 1, wherein the exhaled air purification chamber comprises a filter, a HEPA filter, a microbicidal agent, a microbicidal light, a microbicidal material, a microbicidal chemical, a microbicidal agent, microbicidal heat, or combinations thereof.

Aspect 23: The air cleaning system of Aspect 1, wherein the exhaled air exhaled air collector, the air suction intake, or both, comprise one or more fans.

Aspect 24: The air cleaning system of Aspect 1, wherein the exhaled air purification chamber, the exhaled air suction conduit, or both, comprise one or more fans.

Aspect 25: The air cleaning system of Aspect 1, wherein the exhaled air collector comprises one or more of a fixed open front, a mostly open front, a completely open front, an exhaled air catch basin, an outer lip, or combinations thereof.

Aspect 26: The air cleaning system of Aspect 1, wherein the exhaled air collector, the exhaled air purification chamber, or both, are an attachable kit.

Aspect 27: The air cleaning system of Aspect 1, wherein the computer monitor, the computer monitor screen, or the electronic display screen are one of a cash register screen or monitor, a gambling screen or monitor, an exercise/workout equipment screen or monitor, a vehicle seat screen or monitor, a theater seat screen or monitor, a classroom screen or monitor, an aircraft seat screen or monitor, a laptop screen or monitor, a desktop computer screen or monitor, a monitor associated with a communication device, or a tablet computer screen or monitor.

Aspect 28: A computer monitor stand comprising, integrated with, housing, supporting, attached to, or releasably attached to an exhaled air collector, an exhaled air purification chamber, or both.

Aspect 29: A computer monitor comprising, integrated with, housing, supporting, attached to, or releasably attached to an exhaled air collector and an exhaled air purification chamber.

Aspect 30: The computer monitor of Aspect 29, wherein the computer monitor comprises, houses, or supports a HEPA filter.

One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. An air cleaning system comprising:
   a) a monitor, a computer monitor, a computer monitor screen, or an electronic display screen having a front surface comprising, providing, or acting as an exhaled air blocking surface for deflecting and/or directing exhaled air of a user downwards and towards an exhaled air suction intake located at a bottom of, beneath and distance separated from the bottom of, or below the monitor, the computer monitor, the computer monitor screen, or the electronic display screen, wherein the exhaled air of the user is suctioned downwards into the exhaled air suction intake;
   b) wherein a horizontal length of the exhaled air suction intake is greater than its vertical height;
   c) wherein said exhaled air suction intake suctions the exhaled air of the user at least one of towards, into, or through, an exhaled air purification chamber or an exhaled air suction conduit leading to the exhaled air purification chamber;
   d) wherein the exhaled air purification chamber is located under and below the front surface of the monitor, the computer monitor, the computer monitor screen, or the electronic display screen; and
   e) wherein the exhaled air purification chamber cleans the exhaled air.

2. The air cleaning system of claim 1, wherein the exhaled air suction intake, the exhaled air purification chamber, or both, are attached to, releasably attached to, incorporated into, or integrated with, a computer monitor stand.

3. The air cleaning system of claim 1, wherein the exhaled air suction intake and/or a second exhaled air suction intake is connected to the at least one of the exhaled air purification chamber or the exhaled air suction conduit leading to the exhaled air purification chamber.

4. The air cleaning system of claim 1, wherein the exhaled air suction intake and/or a second exhaled air suction intake is located adjacent to or within a front or a side of the exhaled air purification chamber.

5. The air cleaning system of claim 1, wherein the exhaled air purification chamber is attached to or releasably attached to the monitor, the computer monitor, the computer monitor screen, or the electronic display screen.

6. The air cleaning system of claim 1, wherein the exhaled air suction intake comprises one or more fans for moving the exhaled air of the user air across the front surface of the monitor, the computer monitor, the computer monitor screen, or the electronic display screen.

7. The air cleaning system of claim 1, wherein the monitor, the computer monitor, the computer monitor screen, the electronic display screen, or combinations thereof, comprise one or more sensors, wherein at least one of the one or more sensors is capable of sensing when an individual is sitting or standing in front of the monitor, the computer monitor, the computer monitor screen, or the electronic display screen.

8. The air cleaning system of claim 1, wherein the monitor, the computer monitor, the computer monitor screen, or the electronic display screen comprise a carbon dioxide sensor, wherein if a predetermined amount of carbon dioxide is met or exceeded, the air cleaning system causes an increase of a clean air delivery rate ("CADR") of the exhaled air purification chamber.

9. The air cleaning system of claim 1, wherein the monitor, the computer monitor, the computer monitor screen, or the electronic display screen comprise an acoustic sensor, wherein if predetermined noise level is met or exceeded, the air cleaning system causes an increase of a clean air delivery rate ("CADR") of the exhaled air purification chamber.

10. The air cleaning system of claim 9, wherein the noise being sensed is an exhaled breath, a cough, a sneeze, or combinations thereof.

11. The air cleaning system of claim 1, wherein at least one of the exhaled air suction intake or the exhaled air purification chamber comprise, house, support, incorporate, are attached to, or are releasably attached to a carbon dioxide reducer.

12. The air cleaning system of claim 11, wherein the carbon dioxide reducer is a living plant.

13. The air cleaning system of claim 1, wherein the monitor, the computer monitor, the computer monitor screen, or the electronic display screen comprise a curved display screen.

14. The air cleaning system of claim 1, wherein the exhaled air purification chamber comprises at least one of a filter, a HEPA filter, a microbicidal light, a microbicidal material, a microbicidal chemical, a microbicidal agent, or microbicidal heat.

15. The air cleaning system of claim 1, wherein the exhaled air suction intake comprises one or more fans.

16. The air cleaning system of claim 1, wherein the exhaled air purification chamber, the exhaled air suction conduit leading to the exhaled air purification chamber, or both, comprise one or more fans.

17. The air cleaning system of claim 1, wherein the monitor, the computer monitor, the computer monitor screen, or the electronic display screen are one of a cash register display screen or monitor, a gambling display screen or monitor, an exercise/workout equipment display screen or monitor, a vehicle seat display screen or monitor, a theater seat display screen or monitor, a classroom display screen or monitor, an aircraft seat display screen or monitor, a laptop display screen or monitor, a desktop computer display screen or monitor, a monitor associated with a communication device, or a tablet computer display screen or monitor.

* * * * *